United States Patent
Gruber

(10) Patent No.: US 9,301,770 B2
(45) Date of Patent: Apr. 5, 2016

(54) SYSTEMS, METHODS AND DEVICES FOR PERFORMING GYNECOLOGICAL PROCEDURES

(71) Applicant: HOLOGIC, INC., Bedford, MA (US)

(72) Inventor: William Harwick Gruber, Southborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 266 days.

(21) Appl. No.: 14/013,775

(22) Filed: Aug. 29, 2013

(65) Prior Publication Data
US 2014/0107404 A1   Apr. 17, 2014

Related U.S. Application Data

(63) Continuation of application No. 12/098,224, filed on Apr. 4, 2008, now Pat. No. 8,528,563.

(60) Provisional application No. 60/910,625, filed on Apr. 6, 2007, provisional application No. 60/910,618, filed on Apr. 6, 2007.

(51) Int. Cl.
*A61B 17/30* (2006.01)
*A61B 1/303* (2006.01)
(Continued)

(52) U.S. Cl.
CPC ............... *A61B 17/30* (2013.01); *A61B 1/0615* (2013.01); *A61B 1/0661* (2013.01); *A61B 1/303* (2013.01);
(Continued)

(58) Field of Classification Search
CPC .... A61B 17/30; A61B 17/4241; A61B 17/22; A61B 5/6875; A61B 1/0661; A61B 1/0615; A61B 17/12045; A61N 5/062; A61N 5/0603; A61N 7/022; A61M 31/002; A61M 25/09; A61M 29/02; A61F 6/225; A61F 6/20
USPC .......... 128/831–840, 842; 606/119, 193, 194, 606/198, 200, 139; 600/104, 29, 32, 33–35, 600/565; 604/106, 107, 108
See application file for complete search history.

(56) References Cited

U.S. PATENT DOCUMENTS 2,849,002 A   8/1958   Oddo et al.
3,561,429 A   2/1971   Jewett
(Continued)

FOREIGN PATENT DOCUMENTS

EP   0010650   5/1980
EP   0044877   2/1982
(Continued)

OTHER PUBLICATIONS

Extended European search report for EP Application No. 07864060.4, mailed Jul. 7, 2010 (9 pages).
(Continued)

*Primary Examiner* — Victoria J Hicks
*Assistant Examiner* — Tarla Patel
(74) *Attorney, Agent, or Firm* — Vista IP Law Group LLP

(57) ABSTRACT

Systems, methods, apparatus and devices for performing improved gynecologic and urologic procedures are disclosed. The system and devices provide simplified use and reduced risk of adverse events. Patient benefit is achieved through improved outcomes, reduced pain, especially peri-procedural pain, and reduced recovery times. The various embodiments enable procedures to be performed outside the hospital setting, such as in a doctor's office or clinic.

12 Claims, 40 Drawing Sheets

(51) Int. Cl.

| | | |
|---|---|---|
| *A61B 17/02* | (2006.01) | |
| *A61B 17/32* | (2006.01) | |
| *A61B 17/42* | (2006.01) | |
| *A61F 6/20* | (2006.01) | |
| *A61M 25/10* | (2013.01) | |
| *A61M 37/00* | (2006.01) | |
| *A61B 1/06* | (2006.01) | |
| *A61B 5/00* | (2006.01) | |
| *A61F 6/22* | (2006.01) | |
| *A61M 25/09* | (2006.01) | |
| *A61M 29/02* | (2006.01) | |
| *A61M 31/00* | (2006.01) | |
| *A61N 5/06* | (2006.01) | |
| *A61N 7/02* | (2006.01) | |
| *A61B 17/12* | (2006.01) | |
| *A61B 17/3207* | (2006.01) | |
| *A61B 17/00* | (2006.01) | |
| *A61B 17/22* | (2006.01) | |
| *A61B 19/00* | (2006.01) | |
| *A61M 25/00* | (2006.01) | |

(52) U.S. Cl.
CPC ........... *A61B 5/6875* (2013.01); *A61B 17/0218* (2013.01); *A61B 17/12045* (2013.01); *A61B 17/12099* (2013.01); *A61B 17/12136* (2013.01); *A61B 17/22* (2013.01); *A61B 17/32002* (2013.01); *A61B 17/42* (2013.01); *A61B 17/4241* (2013.01); *A61F 6/20* (2013.01); *A61F 6/225* (2013.01); *A61M 25/09* (2013.01); *A61M 25/1002* (2013.01); *A61M 25/1011* (2013.01); *A61M 29/02* (2013.01); *A61M 31/002* (2013.01); *A61M 37/0092* (2013.01); *A61N 5/062* (2013.01); *A61N 5/0603* (2013.01); *A61N 7/022* (2013.01); *A61B 17/12013* (2013.01); *A61B 17/320068* (2013.01); *A61B 17/320783* (2013.01); *A61B 2017/00084* (2013.01); *A61B 2017/00278* (2013.01); *A61B 2017/00557* (2013.01); *A61B 2017/00862* (2013.01); *A61B 2017/00876* (2013.01); *A61B 2017/00893* (2013.01); *A61B 2017/12018* (2013.01); *A61B 2017/12127* (2013.01); *A61B 2017/22038* (2013.01); *A61B 2017/306* (2013.01); *A61B 2019/464* (2013.01); *A61B 2019/5206* (2013.01); *A61M 25/0026* (2013.01); *A61M 2025/105* (2013.01); *A61M 2025/1047* (2013.01)

(56) References Cited

U.S. PATENT DOCUMENTS

| | | |
|---|---|---|
| 4,188,952 A | 2/1980 | Loschilov et al. |
| 4,198,981 A | 4/1980 | Sinnreich |
| 4,203,444 A | 5/1980 | Bonnell et al. |
| 4,246,902 A | 1/1981 | Martinez |
| 4,261,360 A | 4/1981 | Perez |
| 4,598,698 A | 7/1986 | Siegmund |
| 4,598,710 A | 7/1986 | Kleinberg et al. |
| 4,650,462 A | 3/1987 | DeSatnick et al. |
| 4,673,393 A | 6/1987 | Suzuki et al. |
| 4,700,694 A | 10/1987 | Shishido |
| 4,729,763 A | 3/1988 | Henrie |
| 4,848,323 A | 7/1989 | Marijnissen et al. |
| 4,895,565 A | 1/1990 | Hillstead |
| 4,949,718 A | 8/1990 | Neuwirth et al. |
| 4,998,527 A | 3/1991 | Meyer |
| 5,078,725 A | 1/1992 | Enderle et al. |
| 5,104,377 A | 4/1992 | Levine |
| 5,108,414 A | 4/1992 | Enderle et al. |
| 5,125,903 A | 6/1992 | McLaughlin et al. |
| 5,163,433 A | 11/1992 | Kagawa et al. |
| 5,163,949 A | 11/1992 | Bonutti |
| 5,183,031 A | 2/1993 | Rossoff |
| 5,195,541 A | 3/1993 | Obenchain |
| 5,201,756 A | 4/1993 | Horzewski et al. |
| 5,222,971 A | 6/1993 | Willard et al. |
| 5,242,462 A | 9/1993 | El-Nounou et al. |
| 5,246,016 A | 9/1993 | Lieber et al. |
| 5,259,836 A | 11/1993 | Thurmond et al. |
| 5,269,798 A | 12/1993 | Winkler |
| 5,275,609 A | 1/1994 | Pingleton et al. |
| 5,304,115 A | 4/1994 | Pflueger et al. |
| 5,320,091 A | 6/1994 | Grossi et al. |
| 5,334,183 A | 8/1994 | Wuchinich |
| 5,361,752 A | 11/1994 | Moll et al. |
| 5,377,668 A | 1/1995 | Ehmsen et al. |
| 5,392,765 A | 2/1995 | Muller |
| 5,402,772 A | 4/1995 | Moll et al. |
| 5,423,844 A | 6/1995 | Miller |
| 5,443,470 A | 8/1995 | Stern et al. |
| 5,450,843 A | 9/1995 | Moll et al. |
| 5,458,112 A | 10/1995 | Weaver |
| 5,484,401 A | 1/1996 | Rodriguez et al. |
| 5,503,626 A | 4/1996 | Goldrath |
| 5,505,730 A | 4/1996 | Edwards |
| 5,514,091 A | 5/1996 | Yoon |
| 5,522,790 A | 6/1996 | Moll et al. |
| 5,540,658 A | 7/1996 | Evans et al. |
| 5,575,788 A | 11/1996 | Baker et al. |
| 5,601,583 A | 2/1997 | Donahue et al. |
| 5,602,449 A | 2/1997 | Krause et al. |
| 5,618,296 A | 4/1997 | Sorensen et al. |
| 5,624,395 A | 4/1997 | Mikhail et al. |
| 5,624,399 A | 4/1997 | Ackerman |
| 5,656,013 A | 8/1997 | Yoon |
| 5,695,511 A | 12/1997 | Cano et al. |
| 5,697,940 A | 12/1997 | Chu et al. |
| 5,709,664 A | 1/1998 | Vandenbroek et al. |
| 5,725,525 A | 3/1998 | Kordis |
| 5,730,725 A | 3/1998 | Yoon |
| 5,738,629 A | 4/1998 | Moll et al. |
| 5,741,287 A | 4/1998 | Alden et al. |
| 5,743,850 A | 4/1998 | Moll et al. |
| 5,743,851 A | 4/1998 | Moll et al. |
| 5,749,845 A | 5/1998 | Hildebrand et al. |
| 5,749,889 A | 5/1998 | Bacich et al. |
| 5,755,731 A | 5/1998 | Grinberg |
| 5,782,800 A | 7/1998 | Yoon |
| 5,800,493 A | 9/1998 | Stevens et al. |
| 5,807,401 A | 9/1998 | Grieshaber et al. |
| 5,823,945 A | 10/1998 | Moll et al. |
| 5,843,046 A | 12/1998 | Motisi et al. |
| 5,855,549 A | 1/1999 | Newman |
| 5,857,585 A | 1/1999 | Tolkoff et al. |
| 5,865,728 A | 2/1999 | Moll et al. |
| 5,873,815 A | 2/1999 | Kerin et al. |
| 5,891,134 A | 4/1999 | Goble et al. |
| 5,899,915 A | 5/1999 | Saadat |
| 5,902,251 A | 5/1999 | vanHooydonk |
| 5,904,649 A | 5/1999 | Andrese |
| 5,904,680 A | 5/1999 | Kordis et al. |
| 5,911,739 A | 6/1999 | Kordis et al. |
| 5,916,198 A | 6/1999 | Dillow |
| 5,954,714 A | 9/1999 | Saadat et al. |
| 5,954,715 A | 9/1999 | Harrington et al. |
| 5,961,444 A | 10/1999 | Thompson |
| 5,961,532 A | 10/1999 | Finley et al. |
| 5,964,755 A | 10/1999 | Edwards |
| 5,964,777 A | 10/1999 | Drucker |
| 5,972,000 A | 10/1999 | Beyar et al. |
| 6,002,968 A | 12/1999 | Edwards |
| 6,032,673 A | 3/2000 | Savage et al. |
| 6,039,748 A | 3/2000 | Savage et al. |
| 6,042,590 A | 3/2000 | Sporri et al. |
| 6,068,626 A | 5/2000 | Harrington et al. |
| 6,080,129 A | 6/2000 | Blaisdell |
| 6,086,544 A | 7/2000 | Hibner et al. |
| 6,117,070 A | 9/2000 | Akiba |

(56) References Cited

U.S. PATENT DOCUMENTS

| | | | |
|---|---|---|---|
| 6,126,635 A | 10/2000 | Simpson et al. |
| 6,139,570 A | 10/2000 | Saadat et al. |
| 6,149,632 A | 11/2000 | Landuyt |
| 6,159,209 A | 12/2000 | Hakky |
| 6,190,357 B1 | 2/2001 | Ferrarl et al. |
| 6,216,043 B1 | 4/2001 | Swanson et al. |
| 6,216,044 B1 | 4/2001 | Kordis |
| 6,221,007 B1 | 4/2001 | Green |
| 6,293,952 B1 | 9/2001 | Brosens et al. |
| 6,319,272 B1 | 11/2001 | Brenneman et al. |
| 6,328,686 B1 | 12/2001 | Kovac |
| 6,378,524 B1 | 4/2002 | Jones |
| 6,387,110 B1 | 5/2002 | Drucker et al. |
| 6,395,012 B1 | 5/2002 | Yoon et al. |
| 6,428,498 B2 | 8/2002 | Uflacker |
| 6,428,539 B1 | 8/2002 | Baxter et al. |
| 6,432,116 B1 | 8/2002 | Callister et al. |
| 6,440,061 B1 | 8/2002 | Wenner et al. |
| 6,458,076 B1 | 10/2002 | Pruitt |
| 6,471,644 B1 | 10/2002 | Sidor, Jr. |
| 6,494,909 B2 | 12/2002 | Greenhalgh |
| 6,537,207 B1 | 3/2003 | Rice et al. |
| 6,547,784 B1 | 4/2003 | Thompson et al. |
| 6,565,557 B1 | 5/2003 | Sporri et al. |
| 6,605,037 B1 | 8/2003 | Moll et al. |
| 6,607,545 B2 | 8/2003 | Kammerer et al. |
| 6,612,977 B2 | 9/2003 | Staskin et al. |
| 6,626,940 B2 | 9/2003 | Crowley |
| 6,638,235 B2 | 10/2003 | Miller et al. |
| 6,673,101 B1 | 1/2004 | Fitzgerald et al. |
| 6,682,477 B2 | 1/2004 | Boebel et al. |
| 6,709,667 B1 | 3/2004 | Lowe et al. |
| 6,736,822 B2 | 5/2004 | McClellan et al. |
| 6,742,236 B1 | 6/2004 | Dion et al. |
| 6,763,833 B1 | 7/2004 | Khera et al. |
| 6,802,825 B2 | 10/2004 | Ackerman et al. |
| 6,805,131 B2 | 10/2004 | Kordis |
| 6,812,204 B1 | 11/2004 | McHale et al. |
| 6,821,274 B2 | 11/2004 | McHale et al. |
| 6,827,703 B1 | 12/2004 | Ackerman |
| 6,858,024 B1 | 2/2005 | Berg et al. |
| 6,896,682 B1 * | 5/2005 | McClellan | A61B 17/12013 606/140 |
| 6,951,569 B2 | 10/2005 | Nohilly et al. |
| 6,960,203 B2 | 11/2005 | Xiao et al. |
| 6,979,332 B2 | 12/2005 | Adams |
| 6,997,925 B2 | 2/2006 | Maguire et al. |
| 7,037,321 B2 | 5/2006 | Sachdeva et al. |
| 7,070,559 B2 | 7/2006 | Adams et al. |
| 7,105,003 B2 | 9/2006 | Hiltebrandt |
| 7,150,713 B2 | 12/2006 | Shener et al. |
| 7,189,206 B2 | 3/2007 | Quick et al. |
| 7,226,459 B2 | 6/2007 | Cesarini et al. |
| 7,226,460 B2 | 6/2007 | Gibson et al. |
| 7,249,602 B1 | 7/2007 | Emanuel |
| 7,458,940 B2 | 12/2008 | Miller |
| 7,462,187 B2 | 12/2008 | Johnston et al. |
| 7,468,060 B2 | 12/2008 | Utley et al. |
| 7,481,817 B2 | 1/2009 | Sauer |
| 7,491,212 B2 | 2/2009 | Sikora et al. |
| 7,497,833 B2 | 3/2009 | Miller |
| 7,510,563 B2 | 3/2009 | Cesarini et al. |
| 7,588,545 B2 | 9/2009 | Cohen et al. |
| 7,611,474 B2 | 11/2009 | Hibner et al. |
| 7,625,392 B2 | 12/2009 | Coleman et al. |
| 7,666,200 B2 | 2/2010 | Heisler |
| 7,749,254 B2 | 7/2010 | Sobelman et al. |
| 7,753,857 B2 | 7/2010 | Hibner |
| 7,763,033 B2 | 7/2010 | Gruber et al. |
| 7,785,250 B2 | 8/2010 | Nakao |
| 7,806,835 B2 | 10/2010 | Hibner et al. |
| 7,938,804 B2 | 5/2011 | Fischvogt |
| 8,025,656 B2 | 9/2011 | Gruber et al. |
| 2001/0008575 A1 | 7/2001 | Rho et al. |
| 2001/0029371 A1 | 10/2001 | Kordis |
| 2001/0041900 A1 | 11/2001 | Callister et al. |
| 2001/0047183 A1 | 11/2001 | Privitera et al. |
| 2001/0056222 A1 | 12/2001 | Rudischhauser et al. |
| 2002/0010457 A1 | 1/2002 | Duchon et al. |
| 2002/0013601 A1 | 1/2002 | Nobles et al. |
| 2002/0020417 A1 | 2/2002 | Nikolchev |
| 2002/0068934 A1 | 6/2002 | Edwards et al. |
| 2002/0082634 A1 | 6/2002 | Kammerer et al. |
| 2003/0050639 A1 | 3/2003 | Yachia et al. |
| 2003/0083684 A1 | 5/2003 | Cesarini et al. |
| 2003/0114875 A1 | 6/2003 | Sjostrom |
| 2003/0153940 A1 | 8/2003 | Nohilly et al. |
| 2003/0158563 A1 * | 8/2003 | McClellan | A61B 17/12009 606/151 |
| 2003/0176888 A1 | 9/2003 | O'Connell |
| 2004/0002702 A1 | 1/2004 | Xiao et al. |
| 2004/0002703 A1 | 1/2004 | Xiao et al. |
| 2004/0049211 A1 | 3/2004 | Tremulis et al. |
| 2004/0116955 A1 | 6/2004 | Foltz et al. |
| 2004/0127932 A1 | 7/2004 | Shah |
| 2004/0204682 A1 | 10/2004 | Smith |
| 2004/0225187 A1 | 11/2004 | Kamrava et al. |
| 2004/0255957 A1 | 12/2004 | Cafferata |
| 2004/0267157 A1 | 12/2004 | Miller et al. |
| 2005/0027245 A1 | 2/2005 | Sachdeva et al. |
| 2005/0045183 A1 | 3/2005 | Callister et al. |
| 2005/0074844 A1 | 4/2005 | Yaver et al. |
| 2005/0080318 A1 | 4/2005 | Squicciarini |
| 2005/0090849 A1 | 4/2005 | Adams |
| 2005/0107663 A1 | 5/2005 | Saadat et al. |
| 2005/0113715 A1 | 5/2005 | Schwindt et al. |
| 2005/0113836 A1 | 5/2005 | Lozier et al. |
| 2005/0113857 A1 | 5/2005 | Nohilly et al. |
| 2005/0177168 A1 | 8/2005 | Brunnett et al. |
| 2005/0182397 A1 | 8/2005 | Ryan |
| 2005/0222598 A1 | 10/2005 | Ho et al. |
| 2005/0234437 A1 | 10/2005 | Baxter et al. |
| 2005/0240206 A1 | 10/2005 | Sjostrom |
| 2005/0245960 A1 | 11/2005 | Grundeman |
| 2005/0250933 A1 | 11/2005 | Binz et al. |
| 2005/0250993 A1 | 11/2005 | Jaeger |
| 2005/0267408 A1 | 12/2005 | Grandt et al. |
| 2005/0277970 A1 | 12/2005 | Norman et al. |
| 2005/0277975 A1 | 12/2005 | Saadat et al. |
| 2005/0288551 A1 | 12/2005 | Callister et al. |
| 2006/0004436 A1 | 1/2006 | Amarant et al. |
| 2006/0009798 A1 | 1/2006 | Callister et al. |
| 2006/0036138 A1 | 2/2006 | Heller et al. |
| 2006/0047185 A1 | 3/2006 | Sherner et al. |
| 2006/0064074 A1 | 3/2006 | Mallaby |
| 2006/0089658 A1 | 4/2006 | Harrington |
| 2006/0189972 A1 | 8/2006 | Grossman |
| 2006/0200042 A1 | 9/2006 | Weikel, Jr. et al. |
| 2006/0206136 A1 | 9/2006 | Sachdeva et al. |
| 2006/0212055 A1 | 9/2006 | Karabey et al. |
| 2006/0229647 A1 | 10/2006 | Spitz et al. |
| 2006/0241344 A1 | 10/2006 | Wilk |
| 2006/0241586 A1 | 10/2006 | Wilk |
| 2006/0241630 A1 | 10/2006 | Brunnett et al. |
| 2006/0293560 A1 | 12/2006 | Nguyen et al. |
| 2007/0010845 A1 | 1/2007 | Gong et al. |
| 2007/0161957 A1 | 7/2007 | Guenther et al. |
| 2007/0198050 A1 | 8/2007 | Ravenscroft et al. |
| 2007/0225744 A1 | 9/2007 | Nobles et al. |
| 2007/0227544 A1 | 10/2007 | Swann et al. |
| 2007/0232859 A1 | 10/2007 | Secrest et al. |
| 2008/0015621 A1 | 1/2008 | Emanuel |
| 2008/0051758 A1 | 2/2008 | Rioux et al. |
| 2008/0058588 A1 | 3/2008 | Emanuel |
| 2008/0058595 A1 | 3/2008 | Snoke et al. |
| 2008/0065125 A1 | 3/2008 | Olson |
| 2008/0097467 A1 | 4/2008 | Gruber et al. |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146873 A1 | 6/2008 | Adams et al. |
| 2008/0147012 A1 | 6/2008 | Rome |

(56) References Cited

U.S. PATENT DOCUMENTS

| | | |
|---|---|---|
| 2008/0178890 A1 | 7/2008 | Townsend et al. |
| 2008/0183192 A1 | 7/2008 | Saal et al. |
| 2008/0234715 A1 | 9/2008 | Pesce et al. |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262302 A1 | 10/2008 | Azarbarzin et al. |
| 2008/0281224 A1 | 11/2008 | Johnson |
| 2008/0319342 A1 | 12/2008 | Shabaz et al. |
| 2009/0005739 A1 | 1/2009 | Hart et al. |
| 2009/0048485 A1 | 2/2009 | Heisler |
| 2009/0054728 A1 | 2/2009 | Trusty |
| 2009/0084386 A1 | 4/2009 | McClellan et al. |
| 2009/0118699 A1 | 5/2009 | Utley et al. |
| 2009/0137927 A1 | 5/2009 | Miller |
| 2009/0177217 A1 | 7/2009 | Keller |
| 2009/0198149 A1 | 8/2009 | Privitera et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2009/0306703 A1 | 12/2009 | Kashkarov et al. |
| 2010/0063360 A1 | 3/2010 | Harrington et al. |
| 2010/0152533 A1 | 6/2010 | Mark |
| 2010/0152758 A1 | 6/2010 | Mark et al. |
| 2010/0152761 A1 | 6/2010 | Mark |
| 2010/0160818 A1 | 6/2010 | Haberstich et al. |
| 2010/0163054 A1 | 7/2010 | Breznel et al. |
| 2010/0179480 A1 | 7/2010 | Sugiki et al. |
| 2010/0185153 A1 | 7/2010 | Sugiki et al. |
| 2010/0198242 A1 | 8/2010 | Heisler |
| 2010/0274194 A1 | 10/2010 | Sobelman et al. |
| 2010/0312053 A1 | 12/2010 | Larsen |
| 2011/0034943 A1 | 2/2011 | Churchill et al. |
| 2011/0077674 A1 | 3/2011 | Sullivan et al. |
| 2012/0067352 A1 | 3/2012 | Gruber et al. |

FOREIGN PATENT DOCUMENTS

| | | |
|---|---|---|
| EP | 0141589 | 5/1985 |
| EP | 0366292 | 5/1990 |
| EP | 0449663 | 10/1991 |
| EP | 0531710 | 10/1991 |
| EP | 0539125 | 4/1993 |
| EP | 782427 | 2/1996 |
| EP | 853468 | 5/1996 |
| EP | 0812573 | 12/1997 |
| EP | 1259180 | 11/2002 |
| EP | 1635695 | 1/2005 |
| FR | 2701401 | 8/1994 |
| WO | WO 9407445 | 4/1994 |
| WO | WO 94/11052 | 5/1994 |
| WO | WO 9510326 | 4/1995 |
| WO | WO 95/32011 | 11/1995 |
| WO | WO 96/15741 | 5/1996 |
| WO | WO 98/18520 | 5/1998 |
| WO | WO 9829068 | 7/1998 |
| WO | WO 98/51244 | 11/1998 |
| WO | WO 9960960 | 12/1999 |
| WO | WO 0000100 | 1/2000 |
| WO | WO 00/12832 | 3/2000 |
| WO | WO 00/66031 | 11/2000 |
| WO | WO 01/08575 | 2/2001 |
| WO | WO 03/037194 | 5/2003 |
| WO | WO 2005009504 | 2/2005 |
| WO | WO 2005048862 | 6/2005 |
| WO | WO 2005/074844 | 8/2005 |
| WO | WO 2005/104966 | 11/2005 |
| WO | 2008/058212 A3 | 5/2008 |
| WO | WO 2009/111717 | 9/2009 |
| WO | WO 2010/127171 | 11/2010 |
| WO | WO 2010/127174 | 11/2010 |

OTHER PUBLICATIONS

International Search report and Written Opinion for PCT/US2007/083982, mailed May 20, 2008 (6 pages).
U.S. Appl. No. 12/917,351, including its prosecution history, and the Office Actions, Feb. 10, 2011, Churchill, et al.
U.S. Appl. No. 12/956,974, including its prosecution history, and the Office Actions, May 19, 2011, Adams, et al.
U.S. Appl. No. 12/972,233, including its prosecution history, and the Office Actions, Mar. 31, 2011, Sullivan, et al.
U.S. Appl. No. 12/565,620, including its prosecution history, and the Office Actions, Apr. 8, 2010, Adams, et al.
U.S. Appl. No. 12/842,775, including its prosecution history, and the Office Actions, Mar. 3, 2011, Gruber, et al.
U.S. Publication No. 2009-0270897 A1, including its prosectuion history, and the Office Actions, Oct. 29, 2009, Adams, et al.
U.S. Publication No. 2009-0270896 A1, including its prosecution history, and the Office Actions, Oct. 29, 2009, Sullivan, et al.
U.S. Publication No. 2009-0270898 A1, including its prosectuion history, and the Office Actions, Oct. 29, 2009, Chin, et al.
International Search Report and Written Opinion Received in PCT/US10/56416 Dated Jan. 11, 2011.
International Search Report and Written Opinion Received in PCT/US2010/033047 Dated Jul. 6, 2010.
International Search Report and Written Opinion Received in PCT/US2010/033050 Dated Jun. 29, 2010.
"When mechanical dilation is necessary, a few prerequisites can make a difference", OBG Management, Apr. 2009, vol. 21, No. 4, p. 29-33.
Mark H. Emanuel, "The Intra Uterine Morcellator: A New Hysteroscopic Operating Technique to Remove Intrauterine Polyps and Myomas," Journal of Minimally Invasive Gynecology, vol. 12, p. 62-66 (2005).
Supplementary European Search Report for EP Application No. 08 74 5173, mailed on Feb. 16, 2011 (1 page).
Supplementary European Search Report for EP Application No. 07 86 4060, mailed Jun. 28, 2010 (1 page).
Communication pursuant to Article 94(3) EPC dated Nov. 2, 2011 in European Patent Application No. 08745173.8, Applicant: Hologic, Inc. (5 pages).
Response to European Extended European Search Report dated Sep. 28, 2011 in European Patent Application No. 08745173.8, Applicant: Hologic, Inc. (5 pages).
International Search Report and Written Opinion Received in PCT/US07/79449 Dated Jan. 28, 2008.
International Search Report and Written Opinion Received in PCT/US07/83982 May 20, 2008.
International Search Report and Written Opinion Received in PCT/US08/59493 Dated Apr. 4, 2008.
International Search Report and Written Opinion Received in PCT/US07/83833 Dated Jun. 5 2008.
International Search Report and Written Opinion Received in PCT/US059503 Dated Sep. 5, 2008.
International Search Report and Written Opinion Received in PCT/US08/59504 Dated Sep. 4, 2008.
European Supplementary Search Report, dated Mar. 1, 2011 for European Application No. 08745173.

* cited by examiner

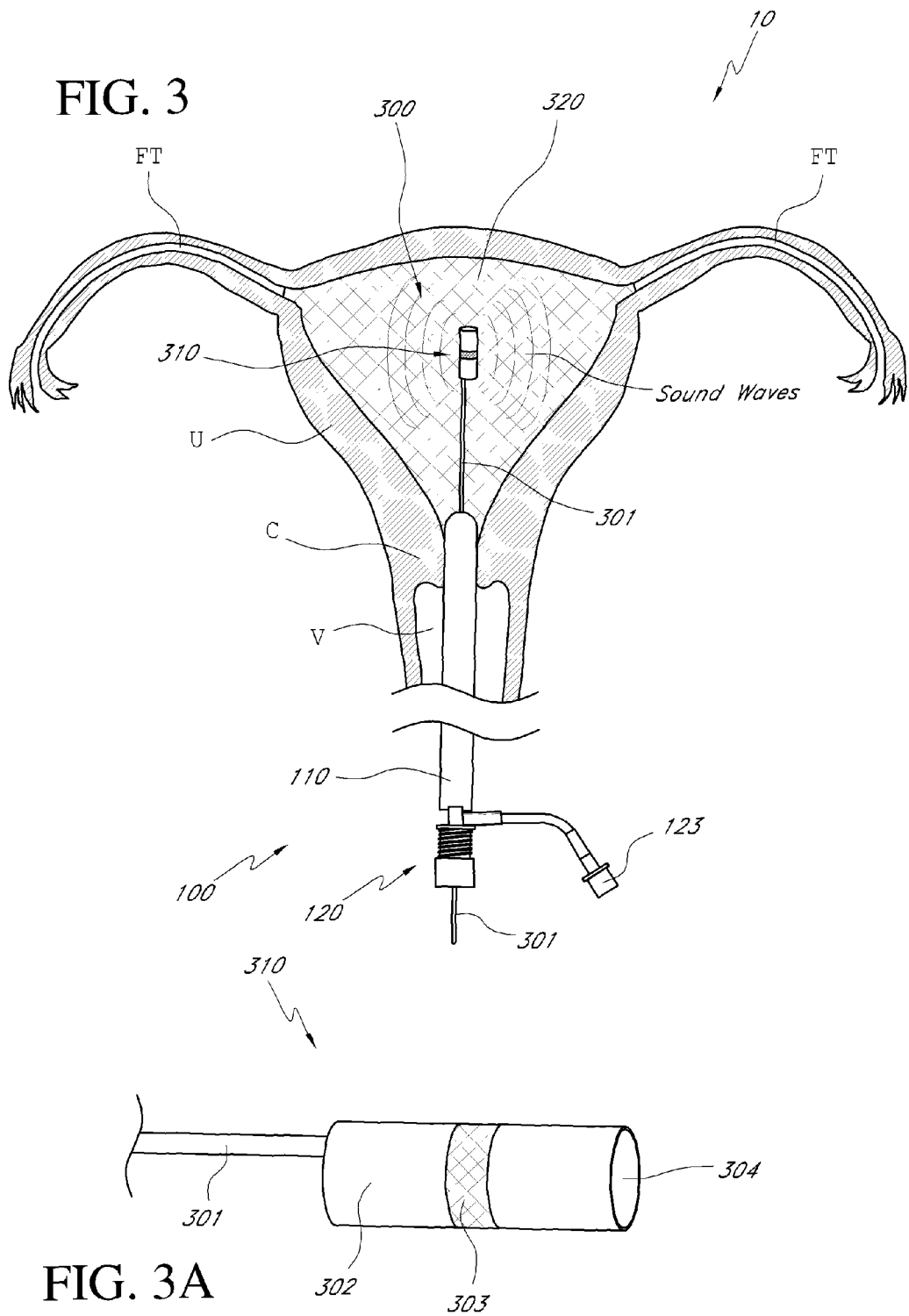

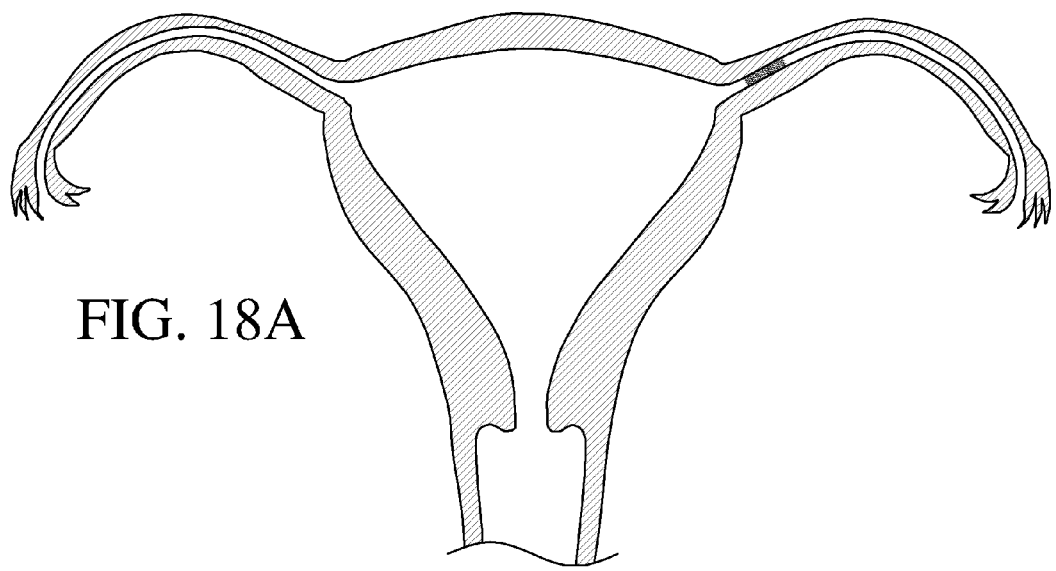
FIG. 18A
FIG. 18B
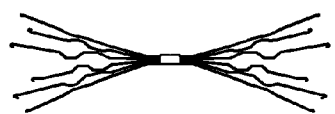
FIG. 18C
FIG. 18E
FIG. 18F
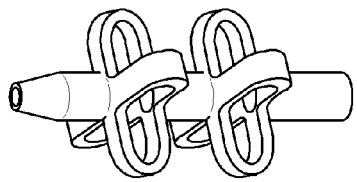
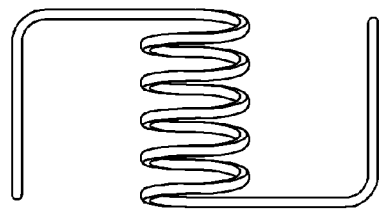

SYSTEMS, METHODS AND DEVICES FOR PERFORMING GYNECOLOGICAL PROCEDURES

CROSS-REFERENCE TO RELATED APPLICATIONS

This application is a continuation of pending U.S. patent application Ser. No. 12/098,224, filed Apr. 4, 2008, which claims the benefit of U.S. Provisional Application Nos. 60/910,625, filed Apr. 6, 2007, and 60/910,618, filed Apr. 6, 2007. The foregoing patent applications are hereby incorporated by reference in their entirety, in particular the lab notebook pages set forth in each application.

BACKGROUND OF THE INVENTION

1. Field of the Invention

The present invention relates to systems, methods, apparatus and devices for performing one or more gynecologic, urologic, and laparoscopic procedures. More particularly, devices and combinations of devices provide simplified use and enhanced safety to support performance various diagnostic and therapeutic procedures in the doctor's office setting.

2. Description of the Related Art

Currently available gynecologic products are difficult to use and often have limited use and functionality. Treatment of gynecologic disorders and ailments is most often performed in a hospital and bears a large cost due to the setting and the support personnel required. Treatment options and modalities are also limited, such that the patient may not be offered the best option for her particular condition.

There is therefore a need for improved gynecologic systems, methods and devices that simplify use, offer improved functionality and enhanced safety.

SUMMARY

According to a first aspect of the invention a hysteroscopic morcellator for performing a gynecologic procedure is disclosed. Hysteroscopic morcellator system (FIG. 1, 100) can include without limitation a slidably receivable visualization means preferably <1.5 mm (for example, a fiber optic scope); an independent aspiration and/or irrigation means; and a tissue removal means such that the combined outer diameters of the multiuse device or separate devices can be placed through body cavity or sheath that has an outer diameter (OD) preferably less than 9 mm, and preferably less than 8 mm, and preferably less than 7 mm, and preferably less than 6 mm, and preferably less than 5 mm, such as to prevent painful and potentially destructive dilation of the cervix is disclosed.

According to another aspect of the invention, the morcellator system can comprise two independent subassemblies such that they that operate together as a single tool that combines one or more functions of cervical distention, uterine distention, visualization, and therapy is disclosed. The first subassembly provides the power means for the morcellation means. The second subassembly contains the aspiration and irrigation ports and the morcellation means. The second subassembly contains all of the body fluid and tissue contacting elements and reduces the interface for the two subassemblies to a single rotating shaft. By separating these two elements, sterilization will only be required for the second subassembly allowing it to be manufactured as a single use disposable device. The power subassembly, which will be battery operated, can be cleaned and reused. The tool or tools combined OD is to be less than 9 mm but preferably less than 8 mm, and preferably less than 7 mm, and preferably less than 6 mm, and preferably less than 5 mm such as to prevent painful and potentially destructive dilation of the cervix. In a preferred embodiment, second subassembly includes a sterile bag which can surround power subassembly such as when second subassembly is attached to power subassembly. In another preferred embodiment, the second subassembly includes an elongate shaft with one or more lumens. These one or more lumens may include a mechanical key such as to orient one or more inserted devices, such as visualization means.

According to another aspect of the invention, the morcellator configuration for the aforementioned system is composed of two or more members with cutting edges and each of these members connected together on a shaft such that they that rotate together as a single tool but one that permits two or more cuts to be made with each rotation of the assembly. By creating multiple cutting elements the speed of the tissue resection will be improved reducing the procedure time. By reducing the procedure time, the risks for anesthesia, fluid intravasation, injury, perforation and distention will be reduced. The morcellator outer diameter is to be less than 7 mm but preferably less than 6 mm, and preferably less than 5 mm, and preferably less than 4 mm, and preferably less than 3 mm, and in some instances less than 2 mm in size, such as to prevent painful and potentially destructive dilation of the cervix.

According to another aspect of the invention, an introducer or morcellator system for performing a gynecologic procedure is disclosed. The introducer or hysteroscopic morcellator system includes a working sheath having an inner diameter (ID) greater than the combined OD of the tool or tools used through it, and this OD can generally be less than 9 mm, preferably less than 8 mm, preferably less than 7 mm, and preferably less than 6 mm, and preferably less than 5 mm, and preferably less than 4 mm, and preferably less than 3 mm such as to prevent painful and potentially destructive dilation of the cervix.

In certain embodiments, the morcellator system is powered by a linear actuation means 121 such that the cutting motion will reflect a guillotine type of action. By utilizing a guillotine type of cutting motion, the morcellation means will allow for a distal cutting block to be used whereby the cut is terminated in a definitive manner. By cutting the tissue with a definitive edge the ability to cut tougher tissues will be enhanced. The morcellator outer diameter can be less than 7 mm, and preferably less than 6 mm, and preferably less than 5 mm, and preferably less than 4 mm, and preferably less than 3 mm, such as to prevent painful and potentially destructive dilation of the cervix.

According to another aspect of the invention, a wireless hysteroscope for viewing the female reproductive tract is disclosed that includes a fiber optic bundle or wires for LED's, camera, integral light source, image capture card and viewing means whose construction includes a rechargeable battery pack to power the system. The advantage of providing a wireless and unconstrained hysteroscope is the freedom to move and rotate the scope without wires or cables impeding the motion. The wireless hysteroscope system having an OD typically less than 6 mm, and preferably less than 5 mm, and preferably less than 4 mm, and preferably less than 3 mm, and preferably less than 2 mm such as to prevent painful insertion and movement through the cervix.

According to another aspect of the invention, an operative sheath for a hysteroscopic system is disclosed that includes a distal lens assembly, integral irrigation/working channel, and retaining means to attach the sheath to the hysteroscope. The use of an operative sheath will enable the sheath to be a single use disposable device that is sterilized while the hysteroscope can be cleaned and reused. The irrigation/working channel ID is preferably 5 Fr. and preferably less than 4 Fr. to enable easy insertion through the cervix. The operative sheath system having an OD typically less than 6 mm, and preferably less than 5 mm, and preferably less than 4 mm, and preferably less than 3 mm, and preferably less than 2 mm such as to prevent painful insertion and movement through the cervix.

According to another aspect of the invention, a scaffolding device or combined system that distends the uterine cavity to a volume equivalent to that of which could be accomplished via a liquid distention media at a pressure of at least 40 mm of HG but not greater than 100 mm HG preferably equivalent to 70 mm Hg, is disclosed.

According to another aspect of the invention, a dilation device such as an inflatable balloon with a fully distended size to be less than 9 mm, and preferably less than 8 mm, and preferably less than 7 mm, and but preferably less than 6 mm, and preferably less than 5 mm, and preferably less than 4 mm, and preferably less than 3 mm, preferably less than 2 mm in size, such as to prevent painful and potentially destructive dilation of the cervix.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The accompanying drawings, which are incorporated in and constitute a part of this specification, illustrate various embodiments of the present invention, and, together with the description, serve to illustrate and not to limit the principles of the invention. In the drawings:

FIG. 3 illustrates a side sectional view of another exemplary embodiment of a system consistent with the present invention, wherein an introducer is shown deployed in the cervix of a patient, and a subsonic treatment device has been advanced through the introducer and into the uterus;

FIG. 3A illustrates a side view of the distal end of the subsonic treatment device of FIG. 3;

FIGS. 18A-18F illustrate an embodiment of a tubal sterilization device for occluding fallopian tubes.

DESCRIPTION OF THE EMBODIMENTS

Figure 1:
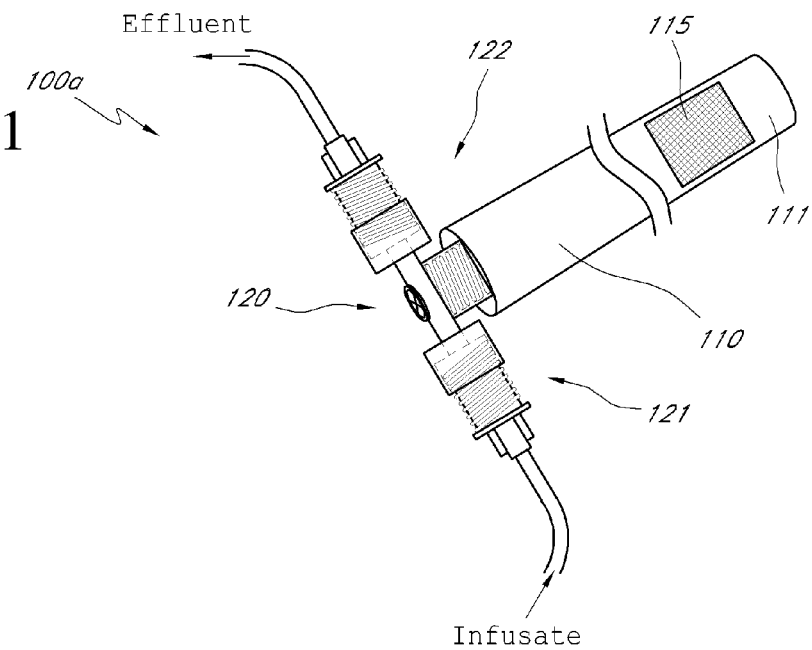
FIG. 1 illustrates a perspective view of an exemplary embodiment of an introducer consistent with the present invention.

To facilitate an understanding of the invention, a number of terms are defined immediately herebelow.
Definitions As used herein, the term "trans-vaginal-wall" refers to devices or procedures which enter the vaginal opening, travel down the vaginal canal, and exit through the vaginal wall proximal to the cervix.

As used herein, the term "trans-cervical" refers to devices or procedures which enter the vaginal opening, travel down the vaginal canal, pass through the cervical canal and enter the uterus.

As used herein, the term "trans-uteral" refers to devices or procedures which pass through the wall of the uterus.

As used herein, the term "drug" refers to all drugs and other agents that may be included in the systems, methods apparatus and devices of the present invention; either by including the drug into a coating or an integral reservoir of a component; or by provided to the patient through other means such as via a lumen and exit port which is in fluid communication with a supply of the drug such as an infusion pump or syringe. Drugs shall include not only pharmaceutical compounds such as anesthetics, anti-thrombotics, thrombotics, anti-bacterial drugs and chemotherapeutics, but also other agents such as ionic solutions, hormones, genes, vitamins, clotting agents, naturally occurring substances such as extracts from plants, and any other compound or agent applicable to the procedures contained herein.

As used herein, "patient" refers to any animal, such as a mammal and preferably a human. Specific examples of "patients" include but are not limited to: individuals requiring medical assistance and healthy individuals.

Systems, methods, apparatus and devices consistent with the invention provide improved diagnostic and therapeutic gynecologic and urologic procedures and outcomes. The simplified, safer use provided allows these procedures to be performed in locations such as a doctor's office or health clinic, eliminating the high costs associated with a hospital setting. Specific devices of the present invention reduce the pain encountered by the patient during and after the associated diagnostic or therapeutic procedure. The devices and apparatus provide to the clinician operator precision in both manipulation and device actions, and often allow reversibility of one or more steps of the procedure without undesirable consequence. Inadvertent tissue trauma is avoided with blunting of tips and other tissue-contacting surfaces. Simplified mechanisms, miniaturized geometries and improved methods reduce procedure times and trauma, and also the associated infection risk and blood loss. Intravasation, the entry of foreign matter in a blood vessel, is also reduced.

A hysteroscopic morcellator (or an introducer) is provided which can be placed into the patient to provide a stabile, working platform to support simplified introduction of one or more diagnostic, treatment or other devices. The hysteroscopic morcellator can comprise an elongate shaft with one or more internal lumens. The proximal end of the shaft may include one or more access ports, such as fluid access ports and device entry ports, as well as one or more controls such as buttons, knobs or levers used to manipulate the hysteroscopic morcellator or activate a mechanical or electronic module of the hysteroscopic morcellator. The hysteroscopic morcellator preferably accepts devices comprising elongate shafts, sequentially or simultaneously. The hysteroscopic morcellator system also permits the administration and or removals of fluid from the patient, such as fluid administered to the uterus, while also providing fluid stasis or maintaining stasis to a maximum pressure at which fluid can be automatically evacuated. The hysteroscopic morcellator system also permits the administration of one or more drugs, such as anesthetic drugs or clotting agents. The hysteroscopic morcellator system may be introduced through the cervix and into the uterus, through the vaginal wall to a location outside the uterus (trans-vaginal-wall), or through another entry path to a specific anatomical location within the patient.

Systems are provided that enable and/or perform diagnostic, therapeutic or combined diagnostic and therapeutic gynecologic and urologic procedures. The systems preferably include one or more of the hysteroscopic morcellator, a treatment device, a tissue removal device, a subsonic treatment device, a drug delivery device, a dilating device, a vaginal-wall-crossing device, a distension device, a volume occupying device, a stabilizing device, a visualization apparatus and a navigation apparatus, all of the present invention, and other devices applicable to gynecological procedures. The systems of the present invention are simple to use, and provide reduced risks while enhancing outcomes.

Treatment Devices are provided which allow a clinician to perform, individually or in combination with additional devices, one or more gynecologic and urologic procedures. The treatment devices provided include but are not limited to: devices which remove, denature or otherwise treat undesired tissue; devices which modify the structure of a vessel such as a fallopian tube or blood vessel occlusion device; drug delivery devices; and other therapeutic or diagnostic devices. The treatment devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. The treatment devices of the present invention may additionally or alternatively perform a diagnostic function. These treatment devices may provide multiple functions, such as diagnostic or treatment functions including applying a tamponade force to bleeding tissue or distending tissue such as uteral wall tissue.

Treatment devices include tissue removal devices which can be inserted through the hysteroscopic morcellator of the present invention and be subsequently operated to remove tissue. Tissue removal device are often arranged with vacuum assemblies which provide a vacuum proximate a tissue removal element and evacuate the tissue to be removed to a site outside of the patient's body.

Treatment devices include subsonic treatment devices which also can be inserted through the hysteroscopic morcellator of the present invention and subsequently deliver subsonic energy to disrupt or otherwise modify tissue such as a fibroid.

Treatment devices include drug delivery devices which can be placed into the patient and controllably deliver a drug to a specific area of tissue or space, such as the vaginal wall, cervix, uterus, uteral wall or fallopian tube as well as a specific fibroid, polyp, tumor or other tissue mass. These drug delivery devices may provide additional functions, such as diagnostic or treatment functions including applying a tamponade force to bleeding tissue or distending tissue such as uteral wall tissue.

Dilating devices are provided which can be used to dilate the cervix, a penetration tract in the vaginal wall, or other tissue. The dilating devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. Specific embodiments include "smart" dilation systems and methods which measure one or more parameters (e.g. device parameters such as strain or pressure or patient parameters such as EKG, EEG, blood pressure or respiration). One or more algorithms are applied to the measured parameters and used to control one or more dilation parameters such as rate, force and magnitude. These dilation devices may be integrated into another device, such as an hysteroscopic morcellator, a treatment device, or other device of the present invention. These dilation devices may provide additional or alternative functions, such as diagnostic or treatment functions including applying a tamponade force to bleeding tissue, distending tissue such as uteral wall tissue, or delivering a drug to tissue. The dilating devices of the present invention are typically configured to dilate to a diameter less than 9 mm, preferably between 5 and 8 mm, and more preferably between 2 and 5 mm. The dilating devices of the present invention are typically dilated to a pressure not to exceed 300 psi (e.g. balloon dilation pressure), and preferably less than 150 psi.

Vaginal-wall-crossing devices are provided that permit safe introduction of one or more devices, such as the hysteroscopic morcellator of the present invention, from inside the vaginal canal, through the vaginal wall to various anatomical locations including but not limited to: the outer wall of the uterus; the outer wall of the fallopian tubes; the ovaries; intra-abdominal locations; other locations and combinations thereof. The crossing devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. In a preferred embodiment, a guidewire is first placed through the vaginal wall, and one or more devices are placed over-the-wire. These crossing devices may provide additional or alternative functions, such as diagnostic or treatment functions including delivering a drug to tissue.

Distension devices are provided which can be introduced into a space, such as the uterus, and apply a force to tissue. The distension devices include without limitation, for example, scaffolding devices or the like. The distension devices are preferably inserted through the hysteroscopic morcellator of the present invention. The distension devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These distension devices may provide additional or alternative functions, such as diagnostic or treatment functions including applying a tamponade force to bleeding tissue or delivering a drug to tissue. These distension devices are preferably inserted into the uterus of a patient such that the distension assembly preferably distends the uteral cavity to a volume equivalent to that which would be attained via a liquid distention media at a pressure of at least 40 mm of HG but not greater than 100 mm HG and preferably approximating 70 mm Hg.

Volume Occupying devices are provided which can be introduced into a space, such as the uterus, and occupy space within the uterus. The volume occupying devices are preferably inserted through the hysteroscopic morcellator of the present invention. The volume occupying devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These volume occupying devices provide the function of taking up space in a cavity, such as taking up space in the uterus to reduce the amount of fluid delivered to the uterus in a diagnostic or therapeutic procedure. These volume occupying devices may provide additional or alternative functions, such as diagnostic or treatment functions including applying a tamponade force to bleeding tissue, distending tissue such as uteral wall tissue, or delivering a drug to tissue.

Stabilizing devices are provided which are used to stabilize one or more separate devices, such as a treatment device of the present invention. Stabilizing devices may include magnets which attract a corresponding magnet integral to the separate device such as to position a treatment device proximate to tissue to be treated. The stabilizing devices preferably include an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device such as an electromagnet located in the distal portion of the shaft. These stabilizing devices may provide additional or alternative functions, such as diagnostic or treatment functions including applying a tamponade force to bleeding tissue, distending tissue such as uteral wall tissue, or delivering a drug to tissue.

Visualization apparatus are provided which provide enhanced imaging of target anatomical locations within the patient. The apparatus include one or more of: miniaturized cameras; infrared cameras; deployable light sources; stabilizing mechanisms; image stabilizing modules and processing; and improved and cost-reduced displays (e.g. a laptop screen display). The visualization apparatus preferably include one or more devices comprising an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These visualization apparatus may provide additional or alternative functions, such as diagnostic or treatment functions including applying a tamponade force to bleeding tissue, distending tissue such as uteral wall tissue, or delivering a drug to tissue.

Navigating apparatus are provided which enable a clinician to navigate one or more diagnostic or therapeutic devices to perform a gynecologic procedure. The navigation apparatus preferably include one or more of: an electro-magnetic (EM) beacon and/or receiver; a light emitter and/or detector; and a magnetic source and/or a detector. The navigation apparatus preferably include one or more devices comprising an elongate shaft, and the shaft may include one or more internal lumens. The proximal end of the shaft may include one or more access ports, such as fluid access ports and device entry ports. A handle may be included on the proximal end, the handle including one or more controls such as buttons, knobs or levers used to manipulate the elongate shaft or activate a mechanical or electronic module of the device. These navigation apparatus may provide additional or alternative functions, such as diagnostic or treatment functions including applying a tamponade force to bleeding tissue, distending tissue such as uteral wall tissue, or delivering a drug to tissue.

Shape-modifying wires are provided which are slidingly received by one or more lumens of a device of the present invention, such as a morcellating or other treatment device used to access and treat a fibroid. Shapes on the one or more shaping wires can bias the elongate shaft of the device, such as at a distal portion, to a pre-determined shape. In a preferred embodiment, multiple shaping wires with varied shapes are provided to accommodate different procedures and/or access to different anatomical locations.

Numerous devices of the present invention include an elongate shaft, similar in construction to shafts used in laparoscopic and percutaneous devices. The shafts may be manufactured in a "lay up" process including multiple layers of similar or dissimilar materials, such as layers of flexible biocompatible material separated by a braided material such as metal wire or plastic filament. The construction is chosen to provide adequate column strength and torqueability to access the desired anatomical locations and perform the desired actions. Each shaft preferably has a blunt or otherwise atraumatic distal tip. The shafts may include one or more lumens, such as a lumen configured to slidingly receive an elongate device such as a treatment catheter or guidewire, a lumen configured to allow fluid delivery and/or fluid sampling or removal; an inflation lumen configured to allow inflation of a balloon; a mechanical linkage lumen configured to slidingly receive a cable such as to transmit force through the shaft (e.g. from a lever on a handle on the proximal end of the shaft); a lumen configured to slidingly receive a shaping wire of the present invention; other lumens and combinations thereof. Each lumen may include one or more mechanical keys, such as to orient an inserted device such as to orient a tissue treatment element or camera device toward a window. Alternatively or additionally, each lumen may be a blind lumen which has an entry port near the proximal end of the shaft, but terminates within the shaft without exiting the distal tip or an exit hole along the shaft. A blind lumen may be incorporated which includes a "window" through which a camera element may be positioned to view outside the elongate shaft. Alternatively or additionally, each lumen may include a mechanical stop, such as to limit the travel of an inserted device.

The elongate shafts of the present invention may include a reinforced section such as a section located at the portion of the shaft that, when inserted into the body, is in proximity to the cervix. The reinforced section can provide the function of preventing collapse of an internal lumen of the shaft (enhanced radial strength) as well as prevent undesired perforation out of the shaft and into tissue such as cervical tissue. The reinforced section may comprise the braiding process described hereabove, and may be provided along a majority of length of the shaft, or a small portion. The shaft may include variable stiffness along its length, and may allow the stiffness to be adjusted, such as through the insertion of a stiffening wire, or by pressurizing an internal (blind) lumen of the shaft. The shaft may include along its length one or more clinician inflatable balloons, such as compliant or non-compliant nylon or PET balloons configured to dilate, deflect the device or neighboring tissue; deliver a drug; or perform another function. The elongate shafts of the present invention are typically less than 9 mm in diameter, and preferably between 5 to 8 mm in diameter, and more preferably between 2 and 5 mm in diameter.

The elongate shafts of the present invention may include clinician controlled deflection means, preferably one or more pull wires attached at their proximal end to a control in a handle on the proximal end of the shaft, and attached on their distal end to a portion of the shaft, such as a distal portion of the shaft. Advancement and retraction of the pull wire causes a portion of the shaft to deflect, such as to bring a treatment element of the present invention in proximity to tissue to be treated. The shafts may further include one or more internal conduits, such as wires or optical fibers which do not need to be advanced or retracted. These conduits may be embedded in the wall of the shaft, fixed to an internal lumen, or sandwiched between to layers present in a layered construction. Wires can be used to transmit electrical signals or energy, in either direction in the shaft. Fiber optic cables can be used to transmit light energy (e.g. laser energy) or signals (e.g. images from a lens), in either direction in the shaft. In the preferred embodiment, the shafts of the present invention include a handle on their proximal end, and the handle includes on or more controls to activate one or more portions of the device. In another preferred embodiment, a "kill-switch" control is included to allow the clinician to quickly stop an ongoing action.

The shafts and other components of the devices of the present invention are constructed of biocompatible materials. The devices may be configured for one-time use or be resterilizable. The materials include medical grade metals, plastics and other materials. Shaped memory metals such as Nitinol and shaped memory polymers may be used to provide controllable material properties or meet specific elasticity and/or resiliency requirements. The shafts and other components may include one or more coatings, such as coatings selected from the group consisting of: anti-infective drugs, anti-thrombogenic drugs; clotting agents; chemotherapeutics; anesthetics such as lidocaine; other drugs; and combinations thereof. Alternatively, the shafts and other components may include drug delivery means, such as drug reservoirs (e.g. connected to a supply of drug internal or external to the device) or drug depots (e.g. containing a supply of drug) One or more markers may be integral to a component of the device, such as a marker selected from the group consisting of: visible and non-visible markers; radiopaque markers; magnetic markers; ultrasonically reflective markers; and combinations thereof.

A functional element may be mounted to the shafts or other components of the devices of the present invention. These functional elements may include a sensor or transducer and/or another functional element such as a camera or marker as described hereabove. Applicable sensors include but are not limited to: electrodes such as electrical mapping electrodes; temperature sensors; pressure sensors; strain gauges; accelerometers; force sensing resistors; position sensors such as linear or rotary encoders; magnetic sensors such as hall effect transistors; optical sensors such as phototransistors; physiologic sensors such as EKG; EEG; respiration; blood sensors such as a blood gas sensors such as an O2 saturation sensors; glucose sensors; blood pressure sensors; pH sensors; other physiologic sensors; and combinations thereof. Applicable transducers include but are not limited to: magnets; electrodes such as radiofrequency electrodes; heat generators; cryogenic generators; force or space-occupying generators such as an expandable balloon or solenoid; drug delivery elements such as iontophoretic elements; sound transducers such as acoustic transducers, ultrasound transducers and subsonic transducers; radiation sources; light sources such as visible or infrared light sources configured to provide a beacon for navigation and ultraviolet light sources configured to treat infection or kill bacteria; visualization elements such as cameras, lenses, fiber optics and ultrasound crystals; other functional elements; and combinations thereof. Functional elements may further include elements to cause dissection of tissue, such as blunt dissection projections and fluid jets.

The systems, methods, apparatus and devices of the present invention are applicable to patients with one or more of the following conditions:
  presence of fibroids, polyps, tumors, blood clots or other undesired tissue (e.g. fibroids attached to the wall of the uterus, in the uteral wall or on the outside of the uterus);
  endometriosis and other abnormal bleeding;
  uteral prolapse;
  ectopic pregnancy;
  fertility issues (e.g. inability to conceive or desire to avoid pregnancy);
  cancer such as carcinoma of the cervix or uterus;
  infection;
  pain;
  and other disorders.

The systems, methods, apparatus and devices of the present invention are applicable to performing one or more therapeutic or diagnostic gynecologic and urologic procedures. These procedures may be performed inside or outside the uterus. Applicable primary procedures include but are not limited to:
  fibroid, poly, tumor, blood clot, biopsy and other tissue removal, treatment or denaturing (e.g. removal, treatment or denaturing via mechanical means such as cutting, morcellating, lysing, excising or scraping; ablation such as radiofrequency, laser or cryogenic ablation; and/or removal of blood supply such as via associated vascular occlusion);
  fertility procedures (e.g. in-vivo fertilization; tubal opening; egg harvesting and sperm delivery);
  sterilization procedures (e.g. fallopian tube occlusion such as internal or external occlusion of the fallopian tube; procedures which detect and/or confirm fallopian tube occlusion; and fallopian tube removal or partial removal);
  endometrial ablation or resection (e.g. providing a tamponade force; delivering a clotting or other agent; delivering a fluid such as a fluid at an elevated temperature; providing ablation energy such as radiofrequency; ultrasonic, laser or cryogenic energy);
  vascular modification (e.g. procedures that change blood flow such as flow reducing or increasing procedures including vascular stenting and occlusion) intra-abdominal procedures (e.g. oophorectomy; tubal ligation; tubal resection; endometrial ablation; subserosal fibroid removal and ovarian cyst removal) drug delivery (e.g. delivery of anesthetics; clotting agents; chemotherapeutics; occlusive agents, bulking agents and other agents In the performance of one or more gynecologic and urologic procedures, such as one or more of the procedures listed above, the systems, methods, apparatus and devices of the present invention may be used to perform one or more additional procedures, including but not limited to:
  mechanical or gel distension of organs (e.g. bladder, lung, stomach, bowel, esophagus, oral cavity, rectum, nasal sinus, Eustachian tubes, heart, gall bladder, artery, vein, ducts)
  administering of anesthetics (e.g. lidocaine injections proximate the cervix, vaginal wall or other tissue; and injections to otherwise reduce pain associated with cervical dilation; fallopian tube manipulation and vaginal wall penetration)
  administering of a muscle relaxant, cervical pre-dilation and softening (e.g. a procedure performed a day or more in advance of a subsequent gynecological procedure)

dilation (e.g. cervical dilation and dilation of a penetration tract through the vaginal wall)

tissue dissection (e.g. blunt dissection; liquid-jet (e.g. saline) dissection; and energy assisted dissection; and dissection utilizing Tumescent solution comprising an anesthetic such as lidocaine and a vasoconstrictor such as epinephrine in order to dissect along normal facial planes and reduce nerve damage)

vaginal wall and other conduit or organ penetration (e.g. penetration comprising an penetrating needle and guidewire passed through the needle)

vessel occlusion or constriction (e.g. occlusion or constriction of a blood vessel such as the uteral artery; a fallopian tube; or the urethra)

implant delivery (e.g. an occlusive device such as occlusive intra-luminal material or a vessel clip; a drug delivery implant such as a drug-loaded gel or foam; a radioactive seed; or suture)

radiation treatment (e.g. temporary or permanent implantation of a radioactive seed or other source of radiation such as a liquid radionucleotide)

delivery of energy (e.g. electromagnetic energy such as radiofrequency energy; chemical energy; heat or cooling energy; mechanical energy such as vibrational energy; sound energy such as subsonic, acoustic and ultrasound energies; radiation; and combinations thereof)

visualization of internal anatomy (e.g. via an endoscope or a camera or lens integral to a device shaft)

guidance of one or more devices (e.g. via a visible beacon such as a light emitted from the uterus, fallopian tubes or other anatomical location or via an electromagnetic beacon such as an antenna receiving a high frequency signal)

The systems, methods, apparatus and devices of the present invention may provide and/or utilize various means and routes of access to an internal location within the patient. Routes of access include but are not limited to:

trans-cervical (defined above);
trans-vaginal-wall (defined above);
trans-uteral (defined above);
trans-vesicle;
trans-urethral;
laparoscopic, and other routes.

The devices and apparatus of the present invention may comprise an elongate shaft that includes one or more lumens such as to slidingly receive one or more separate devices also comprising an elongate shaft. The device lumens may be configured to support over-the-wire insertion over a standard guidewire, or alternatively a side-car mounted near the distal end of the shaft may be provided to support monorail (also known as rapid exchange) insertion. The device lumens, such as the hysteroscopic morcellator of the present invention, may be sized and be otherwise configured to slidingly receive one or more devices including but not limited to:

treatment device, tissue removal device, subsonic treatment device, drug delivery device, distension device, volume occupying device, stabilizing device, visualization apparatus and navigation apparatus, a shape-modifying wire; all of the present invention;
ablation device;
ligating, lysing and/or excising device;
tissue removing device (e.g. a morcellator; scraper; cutter; or grabber);
tissue cutting device (e.g. an advancable blade cutting device);
tissue dissector (e.g. a blunt dissector; a fluid-jet dissector; or an energy delivery dissector);
suture and knot tying device;
snaring device (e.g. a device used to snare a guidewire or blood clot);
visualization device (e.g. a hysteroscope or other endoscope);
navigation device;
drug delivery device (e.g. a iontophoresis catheter);
vaginal crossing device (e.g. a needle based device which places a guidewire from
inside the vaginal canal and through the vaginal wall).

The device lumens may be sized and include access elements such as luer fittings to attach to drug delivery devices such as syringes and infusion pumps. The device elongate shaft may be sized and otherwise configured to be passed through one or more devices including but not limited to:

dilators (e.g. sequential dilators or balloon dilators)
sheaths and introducers

Reference will now be made in detail to the present embodiments of the invention, examples of which are illustrated in the accompanying drawings. Wherever possible, the same reference numbers will be used throughout the drawings to refer to the same or like parts.

Referring now to FIG. 1, a preferred embodiment of a hysteroscopic morcellator consistent with an embodiment of the present invention is illustrated. As shown in FIG. 1, hysteroscopic morcellator 100a includes an elongate, hollow shaft, sheath 110, which is configured to have distal end 111 (preferably with an atraumatic leading edge) be inserted into the body of a patient, such as through the cervix and into the uterus, to provide a working channel to introduce tools through a lumen of sheath 110 and into the uterus. In an alternative embodiment, distal end 111 of sheath 110 is placed into the vaginal opening of a patient, and manipulated to penetrate through the vaginal wall (such as by advancing over a pre-existing guidewire penetrating the vaginal wall), such as to provide a working channel to introduce tools through a lumen of sheath 110 to a location outside the uterus. Sheath 110 may be configured to slidingly receive two or more devices, independently or simultaneously. In an alternative embodiment, sheath 110 includes multiple lumens along its length, each lumen configured to slidingly receive a separate device. Sheath 110 may remain in place throughout the subsequent procedure, or for a portion of the procedural steps. Sheath 110 may be repositioned during the procedure, such as to advance or withdraw sheath 110.

Sheath 110 is manufactured from medical-grade plastics, metals and other biocompatible material such as a sheath including a Teflon outer layer. One or more portions of sheath 110 may be radiopaque, such as by inclusion of a barium sulfate in plastic material or inclusion of one or more metal portions which provide sufficient radiopacity. In a preferred embodiment, distal end 111 includes a radiopaque marker. Sheath 110 is preferably of a braided construction as has been described hereabove, and includes a reinforced portion, reinforcement 115 (e.g. consisting of a metal or plastic braided patch or embedded tube as has been described hereabove) near its distal end, configured to maintain the patency of one or more lumens within sheath 110 when external pressure is exerted (e.g. cervical or vaginal wall pressure) on that portion of sheath 110. Alternatively or additionally, reinforcement 115 may be configured to prevent a device inserted into sheath 110 from inadvertently puncturing out the side of sheath 110, such as to prevent a puncture that would damage cervical or other patient tissue unexpectedly. On the proximal end of sheath 110 is device insertion port 120, which provides access to an internal lumen of sheath 110 and has been configured to maintain fluid stasis with or without a device inserted through it. Port 120 preferably has an "X" cut opening through one or more diaphragms that maintain that fluid seal. The thicknesses of the diaphragms and the materials chosen preferably maintain pressure up to a predetermined level (e.g. 50 mm Hg) after which fluid is automatically evacuated to prevent damage to the patient's internal tissue.

Mechanically attached and in fluid communication with device insertion port 120 are input valve 121 and output valve 122, each of which includes a standard luer connector for attachment to standard fluid infusion lines. Input valve 121 and output valve 122 may include simple one-way valves or more sophisticated valves that open (in either direction or both) at pre-determined pressures. In combination with port 120, fluid infusion and fluid evacuation means (not shown but preferably gravity driven or pump driven fluid movement means), can be attached to port 121 and port 122 and control the level of fluid introduced into the patient via hysteroscopic morcellator 100a. In a preferred embodiment, sheath 110 is a single lumen and the fluid is introduced through that lumen. In an alternative embodiment, sheath 110 includes multiple lumens and fluid can be delivered or evacuated through one or more lumens, simultaneously or independently. In the various gynecological procedures described herein, a volume of liquid and level of liquid pressure are used to visualize the internal space and/or provide space to manipulate one or more devices. In an alternative embodiment, a gel or gas is delivered into the patient.

Hysteroscopic morcellator 100a may include a handle, not shown, on its proximal end. The handle may include one or more controls, as has been described hereabove. Sheath 110 may include one or more valves within one or more lumens of sheath 110, such as a valve near the distal end 111. hysteroscopic morcellator 100a may include a balloon along sheath 110, such as a balloon configured to dilate tissue such as the cervix or the vaginal wall. In an alternative embodiment, multiple balloons are employed, such as a balloon on a balloon configuration. Each balloon integrated into sheath 110 may have an integrally mounted functional element, as has been described hereabove but preferably a pressure or force sensor used to provide information to the clinician or a system component regarding dilation conditions (reference FIG. 13 herebelow). Sheath 110 may include one or more functional elements along its length, such as a vibrational transducer configured to assist in dilation. Sheath 110 may include a lumen for insertion of a shaped wire, such as a wire configured to resiliently bias sheath 110 and/or a wire configured to place a "straightening" bias on the cervical canal during hysteroscopic morcellator insertion, once inserted or both. In another alternative embodiment, sheath 110 includes an expandable cage structure, not shown but protruding from distal end 111. The expandable cage structure may have a fluted geometry such as a geometry configured to follow the contour of the uterus when hysteroscopic morcellator 100a is inserted through the cervix.

Hysteroscopic morcellator 100 of FIG. 1 and the numerous embodiments of the hysteroscopic morcellators described throughout this application, are sized to accommodate the one or more devices placed through sheath 110, while remaining as small as possible to reduce tissue trauma and pain to the patient, especially when sheath 110 is placed through the cervix of a patient. In a first embodiment, sheath 110 of hysteroscopic morcellator 100 is typically less than 9 mm in diameter and preferably less than 8 mm diameter. In another embodiment, sheath 110 is less than 7 mm in diameter. In another embodiment, sheath 110 is less than 6 mm in diameter. In another embodiment, sheath 110 is less than 5 mm in diameter. In another embodiment, sheath 110 is less than 4 mm in diameter. In another embodiment, sheath 110 is less than 3 mm in diameter. In another embodiment, sheath 110 is less than 2 mm in diameter. Sheath 110 is configured in size and rigidity to prevent painful and potentially destructive dilation of the cervix.

Figure 1A:
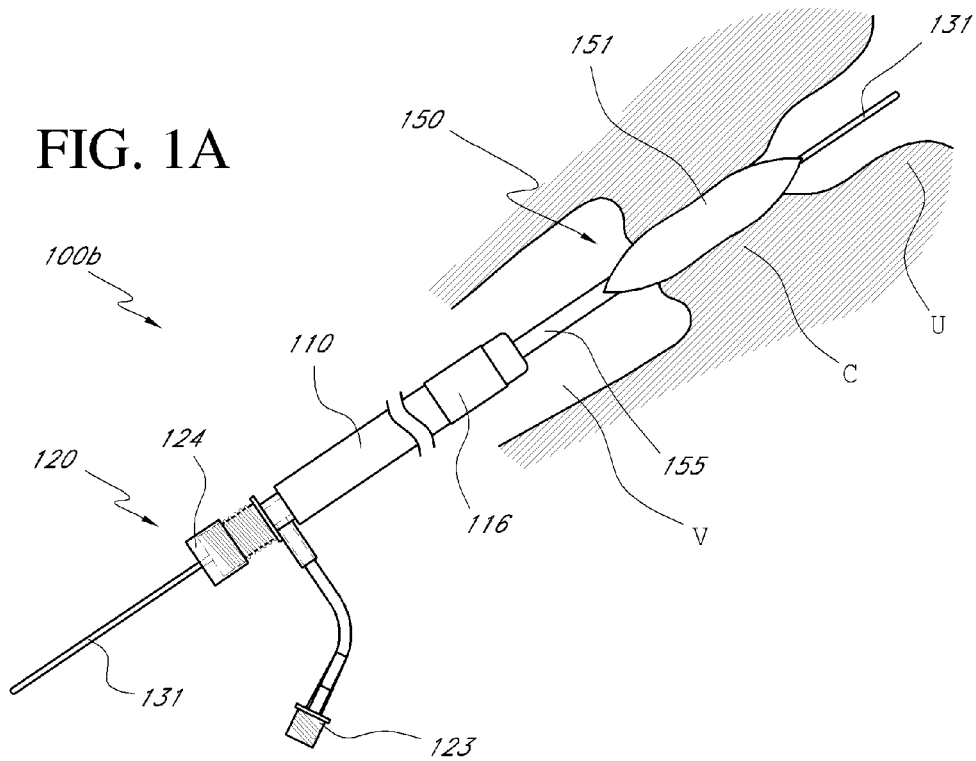
FIG. 1A illustrates a side sectional view of another exemplary embodiment of an introducer consistent with the present invention, wherein the introducer includes a pre-dilating balloon and is shown being deployed in the cervix of a patient.

Referring now to FIG. 1A, another preferred embodiment of a hysteroscopic morcellator consistent with the present invention is illustrated. Hysteroscopic morcellator 100b has a dual balloon construction and includes sheath 110, of similar construction to sheath 110 of FIG. 1. Hysteroscopic morcellator 100b is shown over a guidewire 131, such as an 0.038" standard interventional guidewire, which has been advanced through vagina V, through cervix C and into uterus U. An inflatable balloon introducer assembly 150 includes balloon 151 and shaft 150 and is shown having been advanced into the cervix C of a patient and balloon 151 inflated (inflation lumen and inflation port not shown). Inflation of balloon 151 is used to pre-dilate cervix C such that sheath 110 can be advanced into cervix C. Inflation balloon 151 is preferably less than 9 mm in diameter when fully inflated, and more preferably between 2 and 8 mm in diameter. Shaft 155, which is slidingly received by sheath 110, may be pulled back prior to advancement of sheath 110, or balloon 151 may be left in place, although preferably partially deflated prior to advancement. In an alternative embodiment, balloon assembly 150 including shaft 155 and balloon 151 may be configured to be completely removed from sheath 110 such as after sheath 110 is placed to its desired location in the patient's body. After advancement of sheath 110, further dilation of the cervix may be accomplished by subsequent inflation of balloon 151, and/or via inflation of a balloon integral to sheath 110, balloon 116 (inflation lumen and inflation port also not shown). Inflation of either balloon 151 or balloon 116, or both, may be used to anchor sheath 110 in place.

On the proximal end of sheath 110 is device insertion port 120, which provides access to an internal lumen of sheath 110 and is in fluid communication with fluid transfer port 123 configured to introduce and/or remove fluid or other media through sheath 110 and into the patient as has been described hereabove. Port 120 includes a rotating collar 124, which can be rotated to permit devices to pass through port 120 as well as seal around those devices, such as via a diaphragm which seals around inserted devices similar to a Tuohy Borst valve configuration. Port 120 further provides fluid stasis when no device is inserted through it.

Guidewire 131 may be replaced with a different guidewire, such as with a guidewire with different stiffness or lubricious properties. Guidewire 131 may remain in place for a majority of the procedure, or may be removed early on.

Dumbell or Dog Bone Shape Balloon

In certain embodiments, a balloon catheter approximately 40 cm in overall length and having an uninflated cross-section diameter of less than 4 mm but preferably less than 3 mm having two or more lumens, one extending to the distal tip for a fiber optic or guidewire and one extending to and exiting within the balloon itself for inflation and deflation. Both lumens exit at the proximal end of the catheter. The "through-lumen" used for passing the guidewire or fiber optic can be open ended or have a capped end to keep the fiber optic from touching body fluids. The balloon having a length preferably 12 cm is available in several inflated diameters to dilate the cervix to the appropriate size for the desired instrument. The preferred balloon inflation diameters measured at the midpoint of the balloon are 10 mm, 9 mm, 8 mm, 7 mm, 6 mm, 5 mm and 4 mm. The desired inflation pressure may be greater than 25 atm and in some embodiments greater than 40 atm.

The balloon, having been made of a non-compliant material such as polyethylene teraphthalate (PET) is configured with specific attributes that enable the balloon to inflate distally and proximally similar to a dumbbell or dog bone shape as it grows to its fully distended sausage shape. The purpose of the evolving shape from a dumbbell or dogbone shape to a fully distended shape allows the balloon to remain anchored in its intended location throughout the inflation process. If the balloon preferentially inflated proximally first or distally first the balloon would squirt out from the structure it is trying to dilate.

Figure 1B:
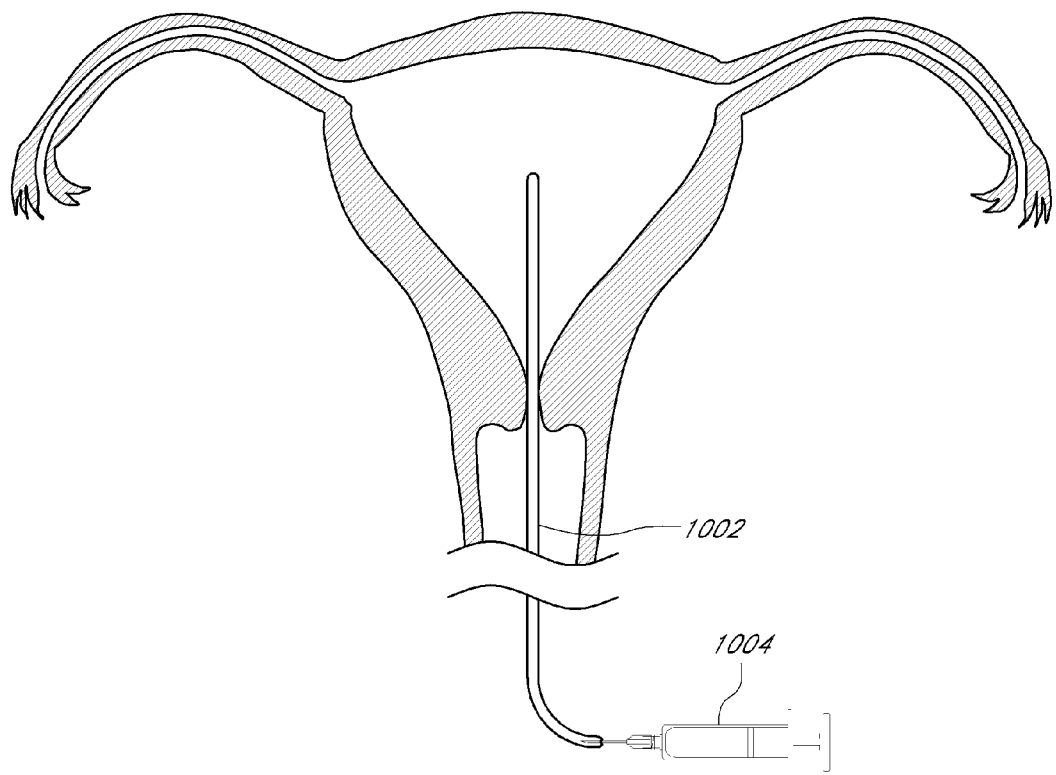
FIGS. 1B, 1C, 1D, 1E, and 1F illustrate embodiments of a balloon catheter.
Figure 1C:
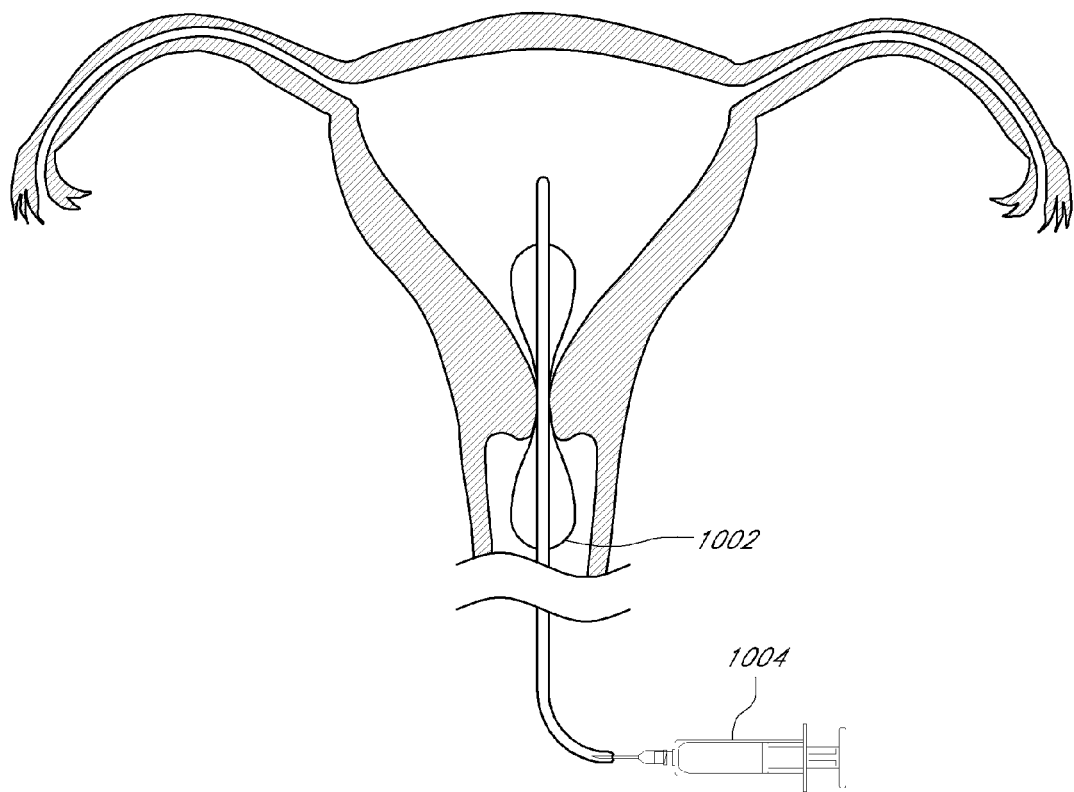
Figure 1D:
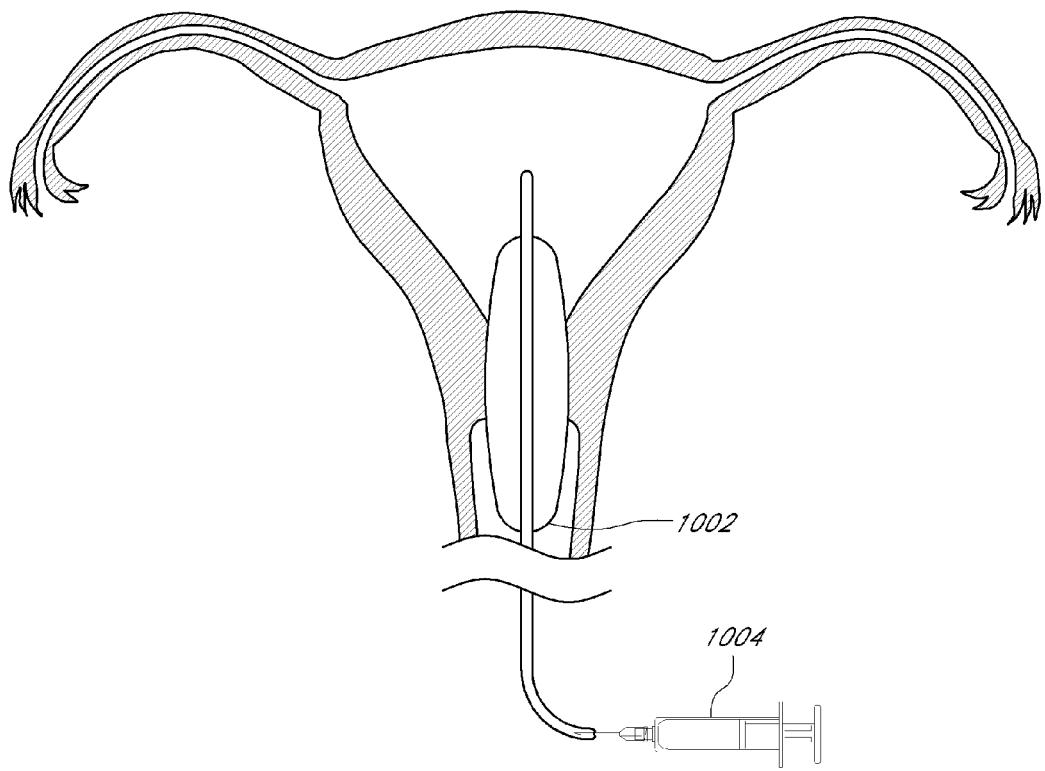

FIG. 1B shows the uninflated balloon across the cervix. The balloon 1002 is affixed to a catheter equipped with an inflation lumen which is connected to a source of inflation media such as a syringe 1004. FIG. 1C shows the balloon 1002 as it is being inflated. The anterior and posterior portions of the balloon are distending first allowing the balloon to remain in position across the cervix. FIG. 1D shows the balloons fully distended and the cervix fully dilated to the same size as the balloon.

Figure 1E:
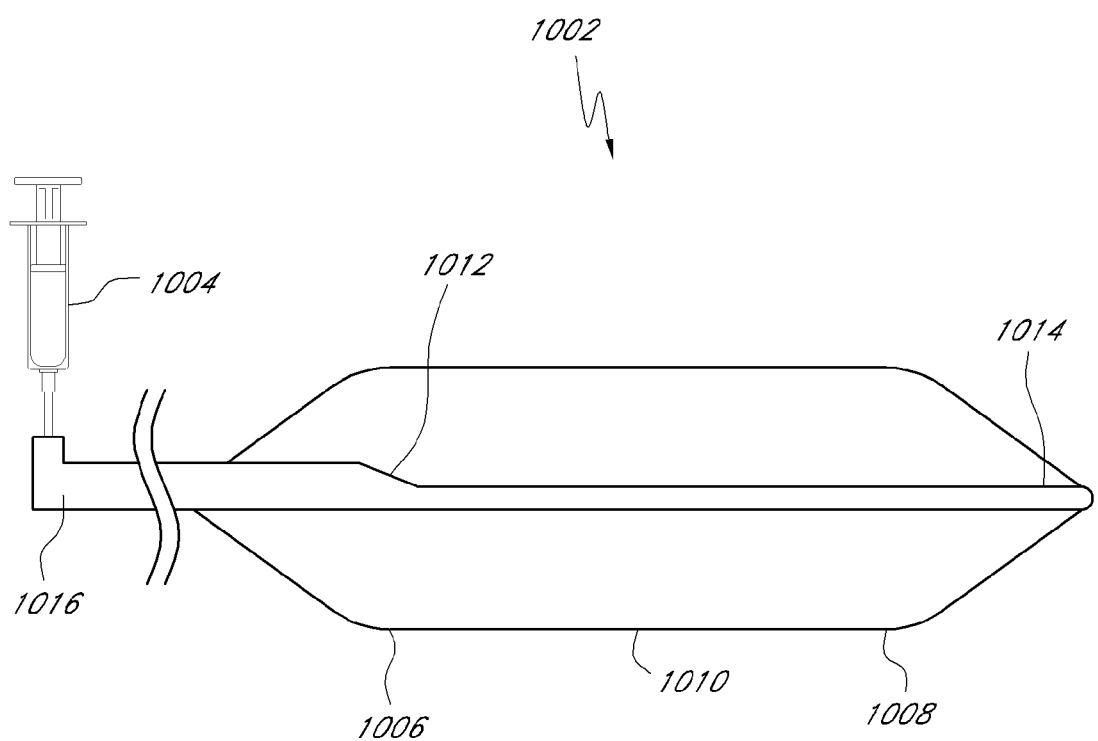

There are several methods to achieving preferential inflation. FIG. 1E shows multiple inflation lumens opening into the balloon. In the illustrated embodiment, the balloon 1002 comprises a proximal zone 1006, a distal zone 1008 and a central zone 1010. When positioned initially for the procedure, the central zone 1010 will be held in compression by the cervix.

A proximal inflation port 1012 is provided for placing the proximal zone 1006 in fluid communication with the inflation media source 1004 by way of an elongated inflation lumen extending through the catheter body 1016. A distal inflation port 1014 places the distal zone 1008 in fluid communication with the source of inflation media 1004 by way of either the first inflation lumen or a second inflation lumen extending throughout the catheter body 1016. Expression of inflation media from the source 1004 will therefore inflate the proximal zone 1006 and the distal zone 1008 under approximately the same inflation pressure, which, in combination with the radially constricted force applied by the cervix in the central zone 1010, will cause the balloon to expand in an initial dog bone configuration.

Alternatively, the balloon 1002 may be configured with an internal baffle (not illustrated) to isolate the proximal section 1006 from the distal section 1008. As a further alternative, each of the proximal section 1006, distal section 1008 and intermediate section 1010 may comprise distinct inflatable balloons. In one implementation of this design, the proximal balloon 1006 and distal balloon 1008 will be coupled to a common inflation lumen enabling simultaneous inflation. The central balloon 1010 is placed in communication with a source of inflation media by way of a unique inflation lumen. In this manner, the inflation of the proximal and distal balloons may be controlled separately from the inflation of the central balloon. One or more additional lumen may be provided in the catheter 1016, depending upon the desired functionality. For example, an elongate central lumen may be provided, extending all the way to the distal tip of the balloon 1002 and further provided with a distal opening. This central lumen may be utilized for any of a variety of purposes, such as for advancing the catheter over a guidewire, and/or for the introduction of fluids and/or tools through the balloon catheter and into the uterus.

Figure 1F:
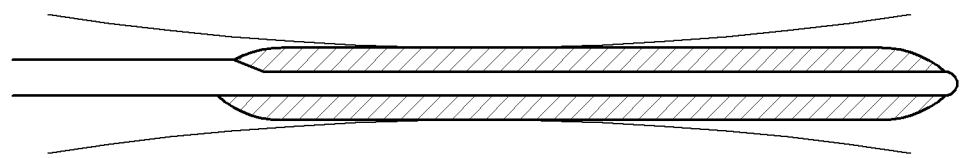

FIG. 1F shows a lower profile of the catheter under where the balloon is mounted to allows the inflation media to travel along the shaft of the balloon to the areas proximal and distal to the structure. These areas are areas of least resistance and will inflate to a maximum pressure beyond which the balloon will not grow. Once this critical pressure is achieved at the unconstrained ends of the balloon, the dilating force will be directed to the anatomical stricture.

Once the balloon is dilated completely, it is left in place for several minutes to stretch the muscles that surround the cervix. Once sufficient stretching is accomplished, the balloon is deflated by drawing back on the plunger of the syringe to remove the inflation media from the balloon.

In an alternative embodiment, the balloon catheter has a third lumen to allow the user to distend the uterus with fluid while the balloon catheter is in place. The balloon catheter thereby provides a stopper function on the uterus to prevent the uterine distension fluid from leaking out. The third lumen can be used for both inflow and outflow of fluid from the uterus.

In yet another embodiment, the balloon can be made of a compliant material such as silicone or latex. In this configuration, the balloon can be used both within the cervix as well as within the uterus to act as a tamponade against uncontrolled bleeding. Using a compliant balloon material allows the balloon to take on the shape of the organ in which it is placed and provides uniform pressure when compared to a non-compliant balloon. This balloon may also have hydrophilic coatings that can carry drugs such as hemostatic agents to aid in the cessation of blood flow or chemotherapeutic agents to treat cancer or ablative agents to sclerose the lining of the uterus.

Figure 1G:
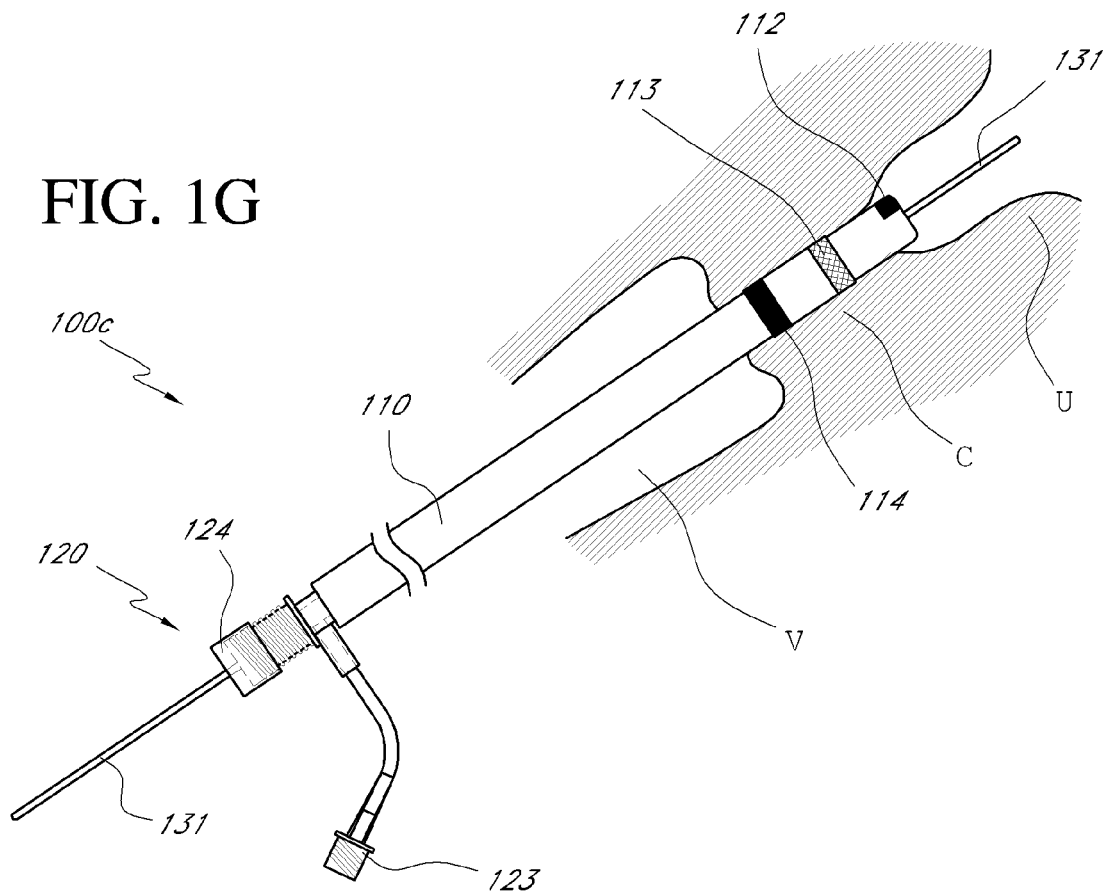
FIG. 1G illustrates a side sectional view of another exemplary embodiment of an introducer consistent with the present invention, wherein the introducer includes a drug delivery element and a strain gauge and is shown deployed in the cervix of a patient.

Referring now to FIG. 1G, another preferred embodiment of a hysteroscopic morcellator consistent with the present invention is illustrated. Hysteroscopic morcellator 100c includes sheath 110 with distal end 111, device insertion port 120 with rotating collar 124 and fluid transfer port 123, all of similar construction to similar components of hysteroscopic morcellator 100a of FIG. 1 and hysteroscopic morcellator 100b of FIG. 2. Hysteroscopic morcellator 100c has been placed over guidewire 141 and advanced such that its distal portion resides within cervix C and its distal end is within uterus U of a patient.

Hysteroscopic morcellator 100c includes a force measuring element, strain gauge 113, which is used to monitor forces exerted on sheath 110 (and the corresponding resultant forces exerted on the neighboring tissue). Wires, not shown but attached to strain gauge 113 and traveling proximally through sheath 110, attach to an electronic module, also not shown, and provide pressure or other force information to the clinician or a system component which processes the information.

Hysteroscopic morcellator 100c further includes drug delivery element 114, such as a drug delivery mechanism. Drug delivery element 114 may be a simple drug coating, or may be a depot that stores a drug such as an anesthetic and delivers the drug via osmosis, iontophoresis or other drug delivery mechanism. In a preferred embodiment, drug delivery element 114 is a pressure releasable sack, such as a sack with a duck bill valve, and when sufficient pressure is applied to the sac, such as via the cervix, a drug, such as lidocaine, is delivered. In another preferred embodiment, drug delivery element 114 includes multiple pressure-driven sacks, such as multiple sacks in different locations and/or multiple sacks with different delivery pressure properties.

Hysteroscopic morcellator 100c further includes a visualization apparatus, visualization element 112 preferably a forward looking visualization tool such as forward looking ultrasound, or a lens that provides an image to a camera, not shown, but preferably a camera system that receives an image from a fiber optic in optical communication with the lens. A display, not shown but preferably integrated into a laptop computer via a USB or video connection, provides the camera image to the clinician and/or patient.

Figure 2:
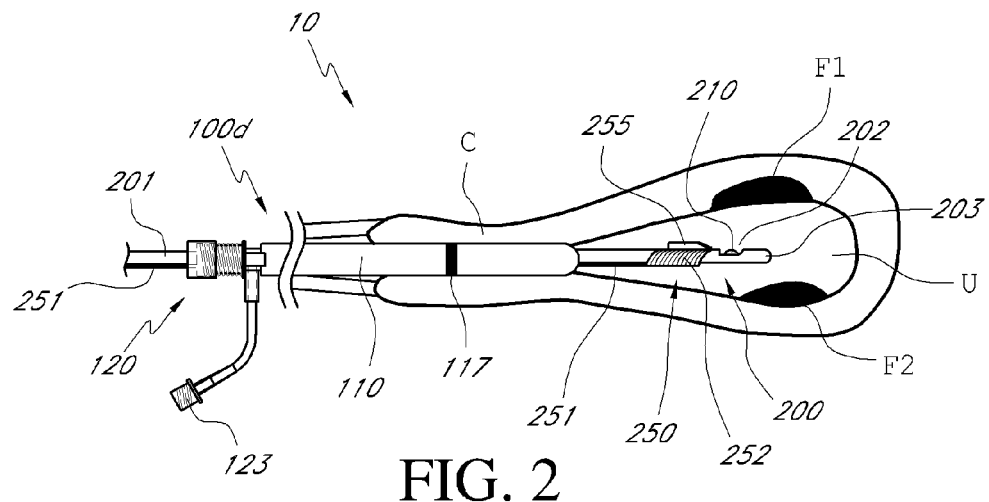
FIG. 2 illustrates a side sectional view of an exemplary embodiment of a system of the present invention, wherein an introducer includes a radiopaque ring and is shown deployed in the cervix, and a tissue removal device with a side-saddle camera has been advanced through the introducer and into the uterus of a patient.

Referring now to FIG. 2, a preferred embodiment of a system 10 consistent with the present invention is illustrated. System 10 includes hysteroscopic morcellator 100d and tissue removal device 200 which includes an integral visualization apparatus, camera 256 mounted to side-saddle catheter 250. Hysteroscopic morcellator 100d includes sheath 110, device insertion port 120 and fluid transfer port 123, all of similar construction to similar components of hysteroscopic morcellators 100a, 100b and 100c hereabove. Hysteroscopic morcellator 100d has been placed and advanced such that its distal portion resides within cervix C and its distal end provides access within uterus U of a patient. Sheath 110 includes a marker, radiopaque ring 117 which can be used by the clinician to determine and/or confirm with fluoroscopy the diameter (e.g. the inside diameter) of sheath 110 at the location of ring 117, such as to confirm or rule out the condition where the cervix may be undesirably compressing sheath 110. In an alternative embodiment, ring 117 is an ultrasonically reflective marker enabling the condition to determine the associated diameter by using ultrasound, such as via an ultrasound device commonly located in a gynecologist office.

Figure 2A:
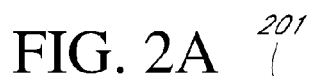
FIG. 2A illustrates a side sectional view of the distal end of a tissue removal device consistent with the present invention, wherein the device includes an oscillating cutter.
Figure 2B:
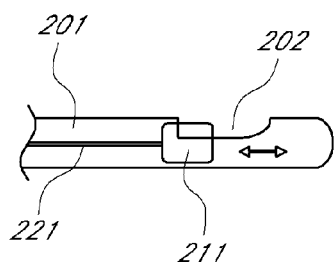
FIG. 2B illustrates a side sectional view of the distal end of another tissue removal device consistent with the present invention, wherein the device includes a rotating cutter.
Figure 2B:
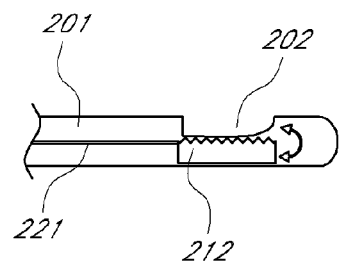

Tissue removal device 200, a morcellating device, has been advanced through port 120, through a lumen of sheath 110, and into the uterus U of a patient. Tissue removal device 200 includes an elongate shaft, tube 201, which includes on its distal end 203 a cutout, window 202. A cutting element 210 is present within window 202 such that as the distal end of tube 201 is manipulated near tissue, cutting element 210 will cut that tissue. Vacuum means, not shown put in fluid communication with a lumen of tube 201 and window 202, evacuate the pulverized, cut or otherwise detached particles to a location outside of the patient. In a preferred embodiment, vacuum and evacuation means are integral to a handle of device 200. In another preferred embodiment, vacuum and evacuation means are connected to a port which is integral to a handle of device 200. Cutting element 210, of one or more configurations such as the configurations described below in reference to FIGS. 2A and 2B, is preferably attached to a speed control mechanism, not shown. The speed control mechanism is simplified for use by including one or more feedback means (e.g. electromotive feedback, rotation or other speed feedback, vibrational feedback, physiologic feedback such as EKG or blood pressure, or other feedback), wherein the feedback means can be used to automatically control the speed, greatly simplifying use for the clinician. In a preferred embodiment, the clinician available feedback is limited to a small number of finite settings, such as less than 10 settings. In another preferred embodiment, a kill-switch is included on a handle of the device, which is readily accessible to the clinician and upon activation removes power and/or applies a breaking function to instantaneously stop the cutting motion.

Figure 2C:
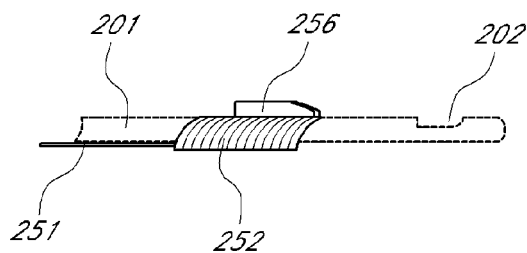
FIG. 2C illustrates a side sectional view of the distal end of a tissue removal device and side-saddle camera, consistent with the present invention.

Referring additionally to FIG. 2C, also included in the system 10 of FIG. 2 is a side-saddle catheter 250 which includes sleeve 252 (e.g. a Teflon sleeve) which slidingly surrounds tube 201. Advancement and retraction of an elongate shaft, shaft 205 causes a visualization apparatus, camera 255 to be correspondingly advanced and retracted relative to tube 201. The image received from camera 255, such as an image displayed on a laptop computer display as has been described hereabove, is used by the clinician to position the window 202 of tissue removal device 200 near one or more fibroids, such as fibroid F1 located within the wall of uterus U and fibroid F2 attached to the wall of uterus U. Camera 225 may utilize CCD and/or MEMS mirror control technology to produce and/or transfer an image. In a preferred embodiment, camera 225 includes one or more motion sensing elements, such as miniaturized accelerometers or gyros which can be fed back to an image processing system, not shown but preferably external to the patient, such that the image provided to the clinician does not move as the camera is moved. Alternatively or additionally, side saddle catheter 250 includes one or more functional elements, not shown but preferably selected from the list of functional elements provided hereabove. The functional element may be a fluid delivery port, such as a port configured to deliver saline or other clear fluid to clear the pathway of the camera view or to clean off a contaminated lens.

Referring now to FIG. 2A, a preferred embodiment of the cutting element 210 of FIG. 2 is shown. The distal end of tube 201 and window 202 is shown with an oscillating cutter 211 attached to an elongate control linkage, shaft 221, which is attached at its proximal end to a reciprocating motor assembly, not shown, but preferably a simplified, precision speed controlled assembly as has been described hereabove. In a preferred embodiment, the speed assembly utilizes feedback, also as has been described hereabove. Referring now to FIG. 2B, another preferred embodiment of the cutting element of FIG. 2 is shown. The distal end of tube 201 and window 202 is shown with an spinning or rotational cutter 212 attached to an elongate control linkage, shaft 221, which is attached at its proximal end to a rotational motor assembly, not shown, but preferably a simplified, precision speed controlled assembly as has been described hereabove. In a preferred embodiment, the speed assembly utilizes feedback, also as has been described hereabove.

System 10 of FIG. 2 is configured such that the outer diameter of sheath 110 of hysteroscopic morcellator 100d is minimized. Inserted devices such as tissue removal device 200 (including camera 256) and other inserted devices are also minimized in the cross sectional profiles of their distal portions, such that the inner diameter (and thus the outer diameter) of sheath 110 can be reduced. In a first embodiment, sheath 110 of hysteroscopic morcellator 100 is typically less than 9 mm in diameter and preferably less than 8 mm diameter. In another embodiment, sheath 110 is less than 7 mm in diameter. In another embodiment, sheath 110 is less than 6 mm in diameter. In another embodiment, sheath 110 is less than 5 mm in diameter. In another embodiment, sheath 110 is less than 4 mm in diameter. In another embodiment, sheath 110 is less than 3 mm in diameter. In another embodiment, sheath 110 is less than 2 mm in diameter. Sheath 110 is configured in size and rigidity to prevent painful and potentially destructive dilation of the cervix.

Referring now to FIG. 3, another preferred embodiment of a system 10 consistent with the present invention is illustrated. System 10 includes hysteroscopic morcellator 100 and subsonic treatment device 300. Hysteroscopic morcellator 100 includes sheath 110, device insertion port 120 and fluid transfer port 123, all of similar construction to similar components of hysteroscopic morcellators 100a, 100b, 100c and 100d hereabove. Hysteroscopic morcellator 100d has been placed and advanced such that its distal portion resides within cervix C and its distal end provides access within uterus U of a patient. A treatment catheter of the present invention, acoustic generator device 300 has been inserted through port 120, down a lumen of sheath 110 and into the uterus of the patient.

Referring additionally to FIG. 3A, acoustic generator device 300 includes acoustic transducer 310 which comprises housing 302, preferably a metal can with a lumen 304, and a sound crystal 303, configured to deliver subsonic sound waves. System 10 preferably includes specialized fluid medium, which is injected into uterus U via port 123 and sheath 110. The fluid medium is configured to adequately conduct the emitted sound waves and provide an impedance mismatch between it and the targeted tissue (e.g. endometrium), such that large amounts of energy (sufficient to destroy or otherwise denature the tissue cells) is transferred to the tissue when the subsonic waves arrive at the interface.

Vibration Device to Cover Tissue, Vessels, and Mucous

Figure 3B:
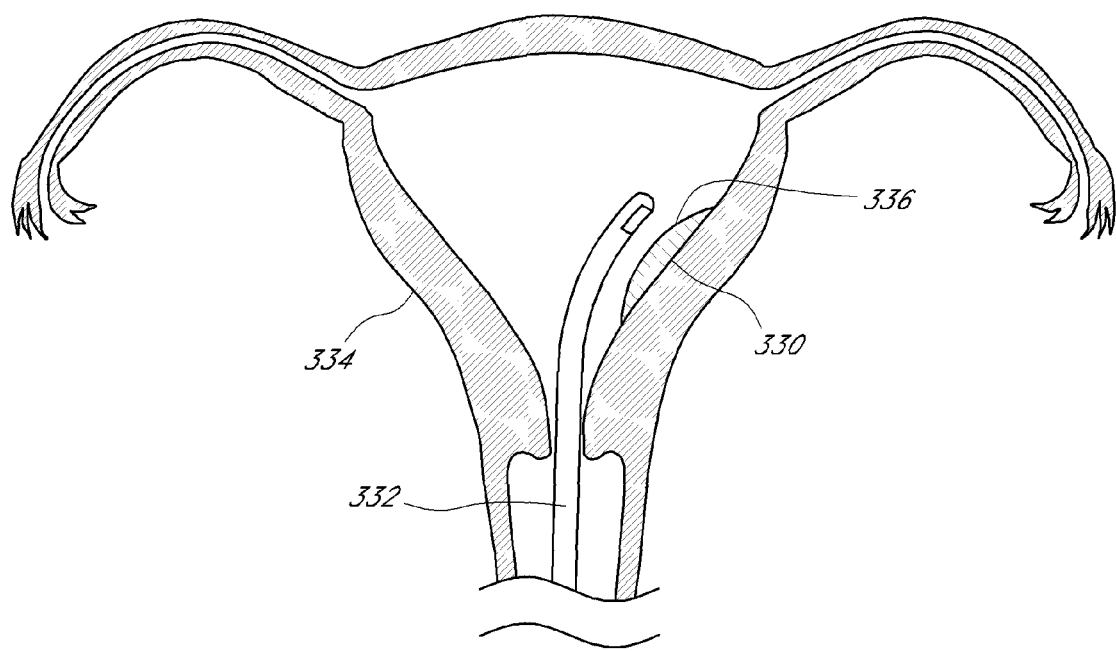
FIGS. 3B, 3C, 3D, and 3E illustrate an embodiment of a vibration device to sever tissue, vessels, and mucous.
Figure 3C:
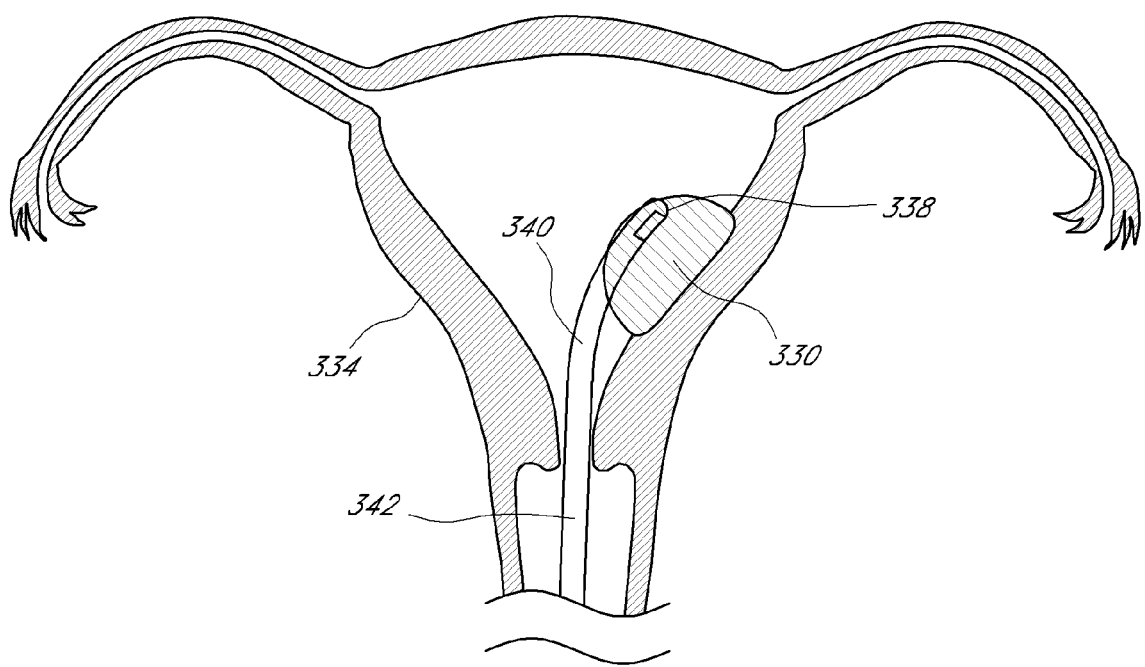

In one embodiment, a device 332 for dislodging a fibroid 330 from the wall of the uterus 334 is illustrated in FIG. 3B and FIG. 3C, which shows a cutting mechanism used to expose the fibroid by dissecting or cutting open the myometrium 336 over the fibroid.

Once the fibroid is exposed, the distension media (saline) would be drained from the uterine cavity allowing the fibroid to become avulsed from the wall of the uterus (FIG. 3B). Once avulsed, the uterus would once again be distended with gas or fluid. The anchoring end 338 of a vibrational wire or catheter 340 would be passed through the vagina and cervix 342 until it engaged the fibroid 330. The catheter or wire would be attached to the fibroid using struts, a corkscrew or similar type tip.

Figure 3D:
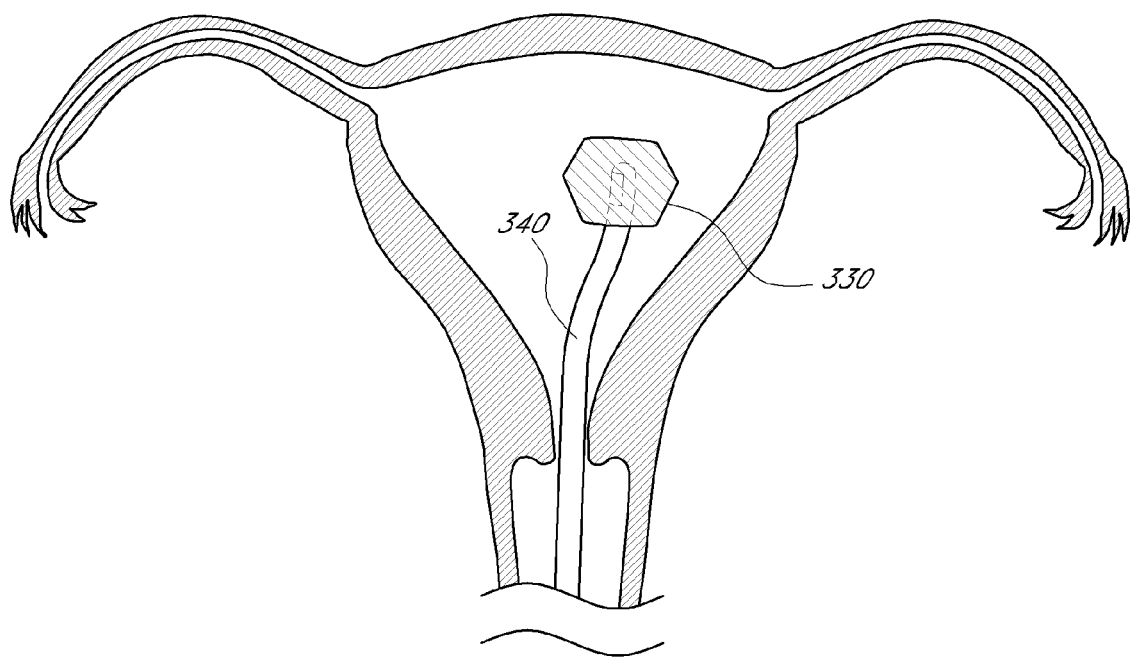

Once sufficiently coupled, the vibrational catheter 340 or wire would be vibrated at a frequency that places the fibroid 330 in opposite (or dissimilar) motion to the surrounding tissue similar to a sine wave. The specific frequency of the vibrational device could be set manually or through a feedback mechanism which measures the energy needed to keep the target tissue in a motion offset from the surrounding tissue. The vibrational frequency could be high or low and could be adjusted using the distension pressure within the uterus. Referring to FIG. 3D, the resulting motion from such vibration would cause the tissue, vessels or mucous to sever, releasing the fibroid 330 from the surrounding tissues causing it to ultimately become freed of the uterine wall.

Figure 3E:
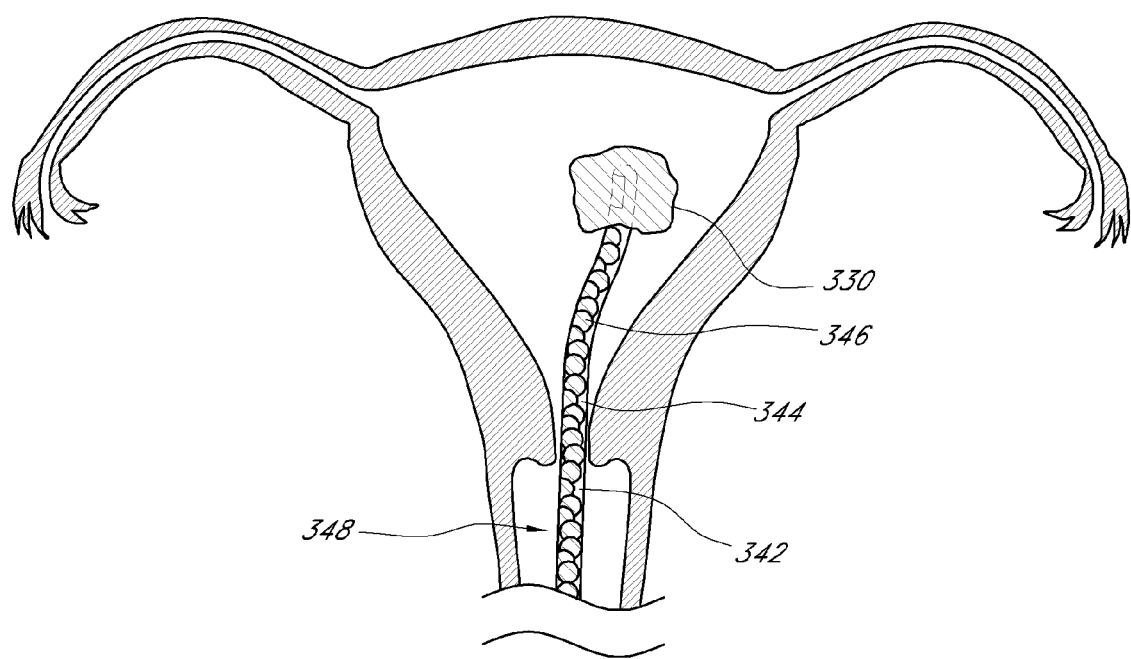

Once free of the uterine wall the fibroid 330 can be removed similar to other tissue freed or excised during laparoscopic surgery. Referring to FIG. 3E, in one embodiment, this is done via a morcellating device 342 comprising a powered helical wire or blade 344 that rotates within an aspiration lumen 346 extending throughout an outer tubular body 348.

In an alternate embodiment, the vibrational catheter 340 or wire is used coaxially within another catheter (not illustrated). The inner device is coupled to the fibroid as stated above but the outer catheter has extendable tines, feet or a cone shaped tip that can couple with the uterine wall such that the outer catheter maintains stability while the inner vibrational member oscillates at a frequency in opposition to that of the outer stabilizing catheter. The shear stress caused by the opposing motion of the two devices will cause the fibroid to detach from the uterus along the outer capsule of the fibroid.

Figure 4:
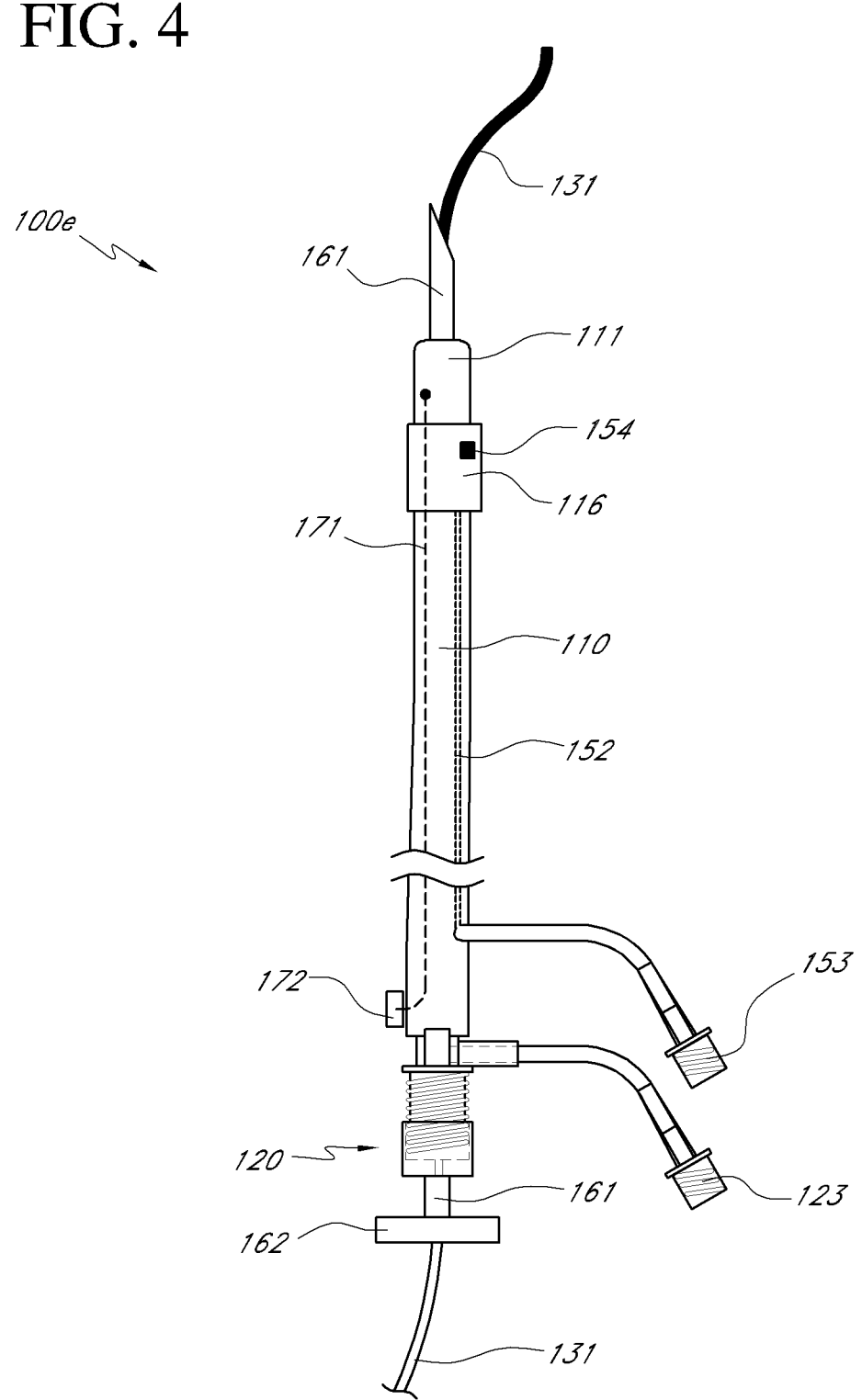
FIG. 4 illustrates a side view of another exemplary embodiment of an introducer consistent with the present invention, wherein the introducer includes a removable needle assembly and an inflatable balloon near its distal end.

Referring now to FIG. 4, another preferred embodiment of a hysteroscopic morcellator consistent with the present invention is illustrated. Hysteroscopic morcellator 100*e* is configured to puncture through tissue, such as the vaginal wall to perform a trans-vaginal-wall procedure. Hysteroscopic morcellator 100*e* includes sheath 110 with balloon 116 and distal end 111, device insertion port 120 and fluid transfer port 123, all of similar construction to similar components of hysteroscopic morcellator 100*a*, 100*b*, 100*c* and 100*d* hereabove.

Balloon 116, which can be configured to perform one or more functions such as to dilate tissue, to anchor sheath 110 in place and to maintain one or more lumens of sheath 110 in an open state under high loading conditions. Balloon 116 is in fluid communication with inflation lumen 152 and injection port 153 such that a syringe or endoflator attached to the luer of port 153 can be used to inflate balloon 116. Balloon 116 includes a miniaturized, integral pressure sensor 154, which is preferably attached to one or more wires, not shown but traveling proximally and attaching to an electronic module which processes the received signal and provides pressure information to the clinician and/or utilizes the information in one or more ways such as to reduce patient pain such as via the "smart" dilation system and method described in detail in reference to FIG. 13 herebelow. Additional balloons and/or pressure sensors may be integrated into sheath 110.

Pull wire 171 is fixedly attached at its distal end to a distal portion of sheath 110, and it is operably attached at its proximal end to knob 172, such that rotation of knob 172 causes sheath 170 to deflect. As shown in FIG. 4, rotation of knob 172 that causes pull wire 172 to retract causes the distal end of sheath 110 to deflect to the left and rotation of knob 172 that causes pull wire 172 to advance causes sheath 110 to deflect to the right. In an alternative embodiment, additional one or more pull wires are included to allow a clinician to deflect sheath 110 in multiple directions at multiple points along the length of sheath 110. Deflection of sheath 110 allows for directional orientation, positioning and advancement of the one or more treatment or other devices that can be inserted into sheath 110 via port 120 (inserted devices not shown).

Hysteroscopic morcellator 100*e* includes a tissue penetrating assembly comprising needle 161, an elongate hollow needle preferably constructed of stainless steel or Nitinol, which has fixedly attached on its proximal end, knob 162. Needle 161 resides within a lumen of sheath 110, and is in place when hysteroscopic morcellator 100*e* is advanced through tissue. Needle 161 has an internal lumen sized to slidingly receive guidewire 131. Guidewire 131 can be placed trough needle 161 after needle 161 has been advanced through tissue (guidewire loaded from proximal end of needle 161). Alternatively, guidewire 131 can be placed to a target location, such as through the vaginal wall of a patient via another needle device, and then passed through needle 161 (guidewire loaded from distal end of needle 161). In a preferred embodiment, needle 161 can be used to deliver anesthetic to tissue prior to needle 161 and/or sheath 110 advancement.

Hysteroscopic morcellator 100*e* may have one ore more functional elements, such as a functional element described hereabove and integrated into sheath 110. In a preferred embodiment, a functional element comprising a visualization apparatus or a portion of a visualization apparatus, such as a camera lens and fiber optic or an ultrasound crystal and associated wiring are contained within sheath 110. Advancement of sheath 110*e*, such as through the vaginal wall to a location neighboring the outside of a patient's uterus, may require dissection of tissue. In a preferred embodiment, hysteroscopic morcellator 100*e* includes a functional element such as a blunt dissector, a fluid jet, or other dissection element. In another preferred embodiment, a blunt dissection device, such as a blunt tipped probe, electrocautery probe, or fluid-jet probe, is advanced through a lumen of sheath 110 prior to and/or during advancement of sheath 110 through tissue. Once inserted into the body of the patient, the distal portion of sheath 110 may need to be tracked, such as it is advanced through the vaginal wall at the preferred location of the anterior or posterior culdesac of the vagina, to a location outside the uterus. Tracking means, such as visualization systems and navigation systems of the present invention, may be used such as by incorporating one or more visualization or navigation elements in hysteroscopic morcellator 100*e* and/or by using separate devices to navigate and/or visualize. In a preferred embodiment, a visible light source is placed in a fallopian tube and a camera integral to hysteroscopic morcellator 100*e* or a device inserted through sheath 110 is used to locate the visible light source and access the associated fallopian tube. In another preferred embodiment, an electromagnetic transmitting antenna is placed in a fallopian tube and a receiving antenna is integral to hysteroscopic morcellator 100e or a device inserted through sheath 110 and is used to locate the transmitting source and access the associated fallopian tube.

Figure 5:
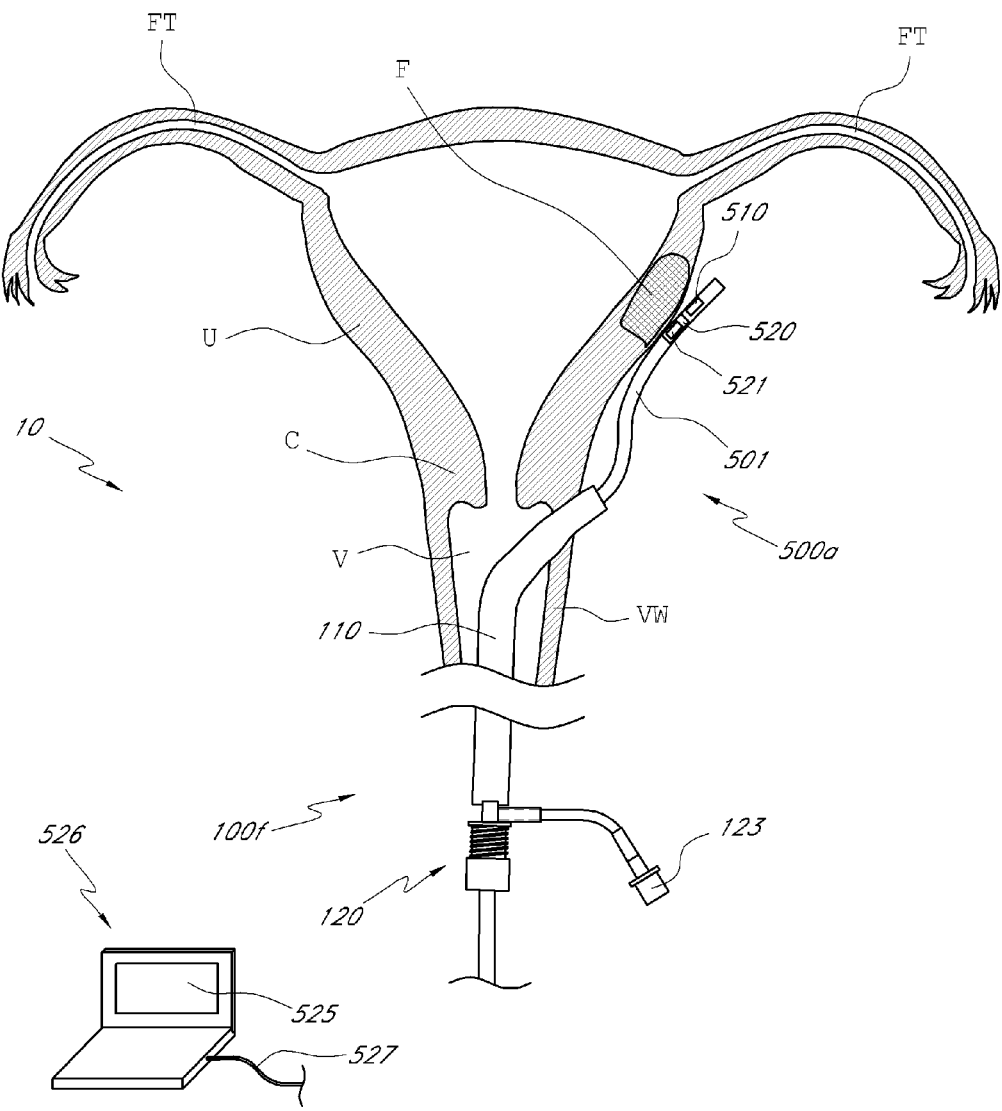
FIG. 5 illustrates a side sectional view of another exemplary embodiment of a system consistent with the present invention, wherein an introducer is shown deployed through the vaginal wall of a patient and a treatment device has been advanced through the introducer to a location outside the uterus and proximate a fibroid in the uteral wall.

Referring now to FIG. 5, another preferred embodiment of a system 10 consistent with the present invention is illustrated. System 10 includes hysteroscopic morcellator 100f and treatment catheter 500a which includes visualization element 520 and orientation apparatus 521. Hysteroscopic morcellator 100f includes sheath 110, device insertion port 120 and fluid transfer port 123, all of similar construction to similar components of hysteroscopic morcellators 100a, 100b, 100c, 100d and 100e hereabove. Hysteroscopic morcellator 100f has been advanced through the vaginal opening into the vagina V of a patient, to a distal location of the vaginal canal, proximate the cervix C. Sheath 110 has exited through the vaginal wall, as was described hereabove in reference to FIG. 4. A treatment or diagnostic device, as have been described in detail hereabove, treatment catheter 500a, has been advanced through a lumen of sheath 110, and further advanced, such as with manipulation via pull wires integral to hysteroscopic morcellator 100f and/or treatment catheter 500a, neither pull wires shown, such that the distal end of treatment catheter 500a is proximate a fibroid F located in the wall of uterus U.

Treatment catheter 500a includes shaft 501, which includes near its distal end treatment element 510, such as a morcellating assembly, a subsonic generator, an excisor, a cutter, an ablation element, or other tissue removal or denaturing element as has been described in detail hereabove. Also located near the distal end of shaft 101 is visualization element 520 which is preferably a camera lens connected to a fiber optic cable and configured to produce an image on display 525 of laptop 526 via a cable, wire bundle 527. Alternatively, visualization element 520 is an ultrasound crystal or crystals such as a rotating crystal or phased array of crystals, configured to produce an image on display 525 of laptop 526 via cable 527. Visualization element 520 further includes orientation apparatus 521, a nanoscale mechanism, such as a MEMS gyroscope, accelerometer or series of mercury switches, that is configured to provide movement information to an image processing unit such that the image provided to the clinician does not move as the visualization element moves. The image processing unit may be integral to laptop 526 and/or another component of system 10.

Shaft 501, which extends beyond the proximal end of hysteroscopic morcellator 100f and exits port 120, preferably includes on its proximal end a handle with one or more clinician controls (e.g. on-off buttons, pull wire rotational knobs, etc) and/or connections such as electrical connections to laptop computer 526, or mechanical connections such as to motor assemblies which provide motion to visualization element 520 (e.g. to a rotating ultrasound crystal) or treatment element 510 (e.g. to a spinning or reciprocating cutting blade).

Anesthetics, such as lidocaine, may be administered peri-procedurally (prior to, during and post procedure), via a separate device, or via one or more functional elements of hysteroscopic morcellator 100f. Numerous gynecological procedures are applicable to the system 10 and method of FIG. 5, including but not limited to: intra-uteral procedures (re-entering uterus thus avoiding cervical crossing); uteral wall procedures (e.g. the fibroid F treatment shown); fallopian tube procedures (e.g. tubal ligation); ovary procedures (e.g. egg harvesting); cancer treatment procedures; pain treatment procedures; other tissue treatment or removal procedures, and intra-abdominal procedures. As described in reference to FIG. 4, one or more blunt dissection procedures may be performed in the placement of hysteroscopic morcellator 100f and/or the advancement of one or more devices (e.g. treatment catheter 500a) through sheath 110 and to the target procedure location. Also as described in FIG. 4, one or more navigation or visualization procedures or devices may be used to navigate hysteroscopic morcellator 100f and/or treatment catheter 500a.

In an alternative embodiment, an additional device is inserted through port 120 and sheath 110, either sequentially or simultaneously with treatment catheter 500a. The additional device may perform one or more functions such as that of a treatment device, navigation device, stabilizing device, visualization device or other device as has been described as performing a function related to the intended gynecologic and urologic procedures described throughout this application. In another alternative embodiment, treatment catheter 500a includes a second treatment element, of similar or dissimilar functionality to treatment element 510.

Figure 5A:
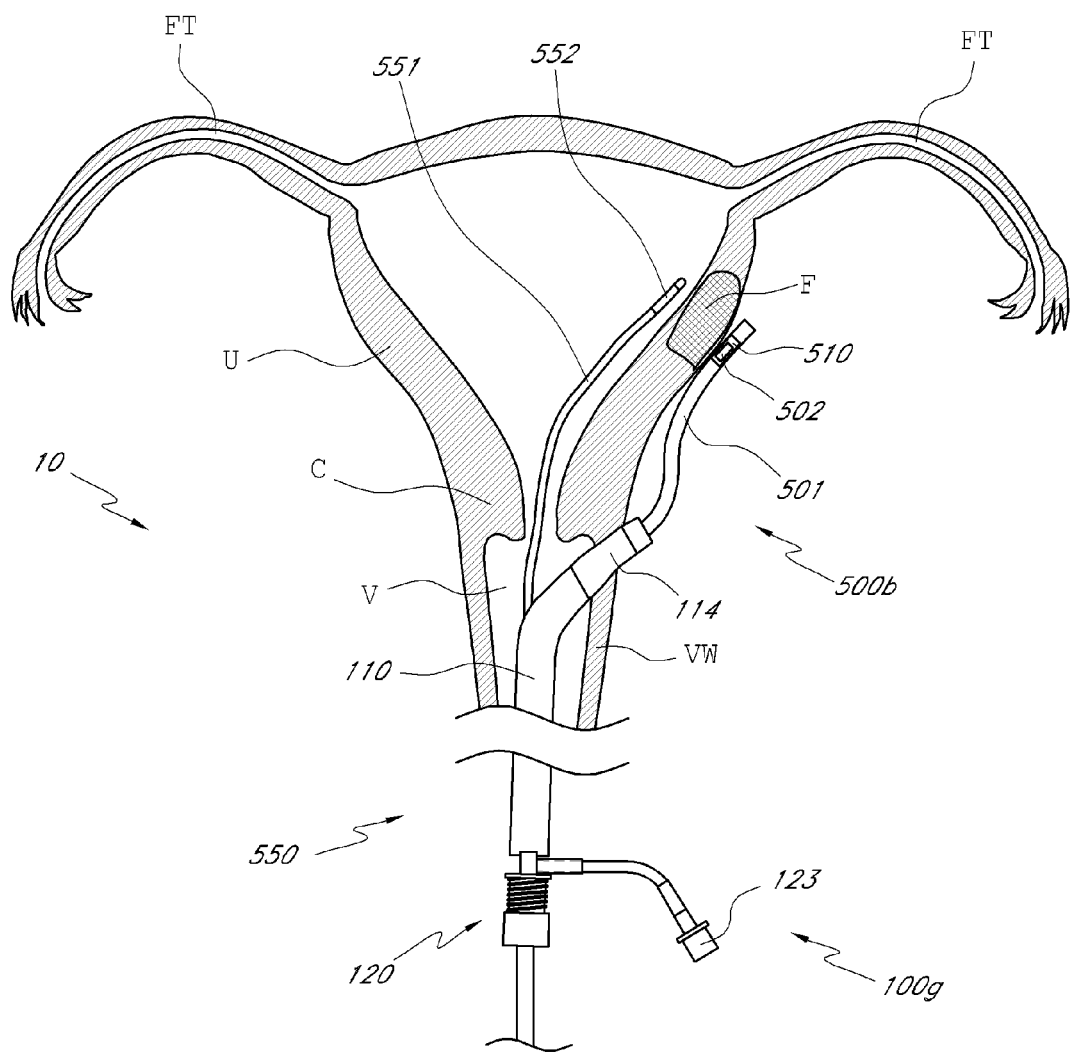
FIG. 5A illustrates a side sectional view of another exemplary embodiment of a system consistent with the present invention, wherein an introducer is shown deployed through the vaginal wall of a patient, a treatment device including a magnet in its distal portion has been advanced through the introducer to a location outside the uterus and a stabilizing magnetic device has been advanced into the uterus proximate a fibroid.

Referring now to FIG. 5A, another preferred embodiment of a system 10 consistent with the present invention is illustrated. System 10 includes hysteroscopic morcellator 100g, treatment catheter 500b and stabilizing device 550. Hysteroscopic morcellator 100g includes sheath 110, device insertion port 120 and fluid transfer port 123, all of similar construction to similar components of hysteroscopic morcellators 100a, 100b, 100c, 100d, 100e and 100f hereabove. Hysteroscopic morcellator 100g has been advanced through the vaginal opening into the vagina V of a patient, to a distal location of the vaginal canal, proximate the cervix C. Sheath 110 has exited through the vaginal wall, as was described hereabove in reference to FIG. 4. Sheath 110 includes drug delivery element 114, located along sheath 110 at a location proximate the intended vaginal wall crossing, such that one or more drugs, preferably an anesthetic such as lidocaine, can be delivered to reduce pain. Drug delivery element 114 may deliver a drug via simple infusion means such as osmosis or a weak-bonded coating transitioning into solution, or more sophisticated means such as pressure-regulated delivery or iontophoresis as has been described in detail hereabove.

A treatment or diagnostic device, as have been described in detail hereabove, treatment catheter 500b, has been advanced through a lumen of sheath 110, and further advanced, such as with manipulation via pull wires integral to hysteroscopic morcellator 100f and/or treatment catheter 500b, neither pull wires shown, such that the distal end of treatment catheter 500b is proximate a fibroid F located in the wall of uterus U. Treatment catheter 500b includes shaft 501, which includes near its distal end treatment element 510, such as a morcellating assembly, a subsonic generator, an excisor, a cutter, an ablation element, or other tissue removal or denaturing element as has been described in detail hereabove. Also located near the distal end of shaft 101 is magnet 502, such as a rare earth magnet or clinician activatable electromagnet configured to allow the distal portion of shaft 501 of catheter 502 to be manipulated by one or more clinician-controllable magnetic fields. System 10 further includes stabilizing device 550, inserted into the uterus through the vagina V and cervix C of the patient (outside of hysteroscopic morcellator 100g). At the distal end of shaft 551 of stabilizing device 500 is a second magnet, magnet 552, preferably a rare earth magnet or clinician activatable electromagnet similar or dissimilar (such as a difference in size and/or magnetic field strength) to magnet 502 of treatment catheter 550b. Manipulation of the distal ends of either or both stabilizing device 550 or treatment catheter 500b such that magnet 552 is in relative proximity to magnet 502 will enable the magnetic force to pull the two magnets and associated distal ends together. In a preferred embodiment, either or both magnet 552 and magnet 502 are electromagnets such that one or both magnetic fields can be deactivated for initial manipulation(s), and activated to achieve final position, such as at a location where treatment element 510 is in close proximity to uteral fibroid F, as shown in FIG. 5A. In a preferred embodiment, the magnetically guided system 10 of FIG. 5a can perform one or more procedures without the need for a camera or other visualization apparatus. In an alternative embodiment, a camera or other visualization apparatus is used, such as with a visualization element incorporated into sheath 100g, treatment catheter 500b or stabilizing device 550.

Shaft 501, which extends beyond the proximal end of hysteroscopic morcellator 100g and exits port 120, and shaft 551 both preferably include on their proximal end a handle with one or more clinician controls (e.g. on-off buttons, pull wire rotational knobs, etc) and/or connections such as electrical connections to a laptop computer (not shown but similar to laptop computer 526 of FIG. 5), or mechanical connections such as to motor assemblies which provide motion to treatment element 510 (e.g. to a spinning or reciprocating cutting blade) or to manipulate one or more internal pull wires such as to create a robotically manipulated system.

Figure 6:
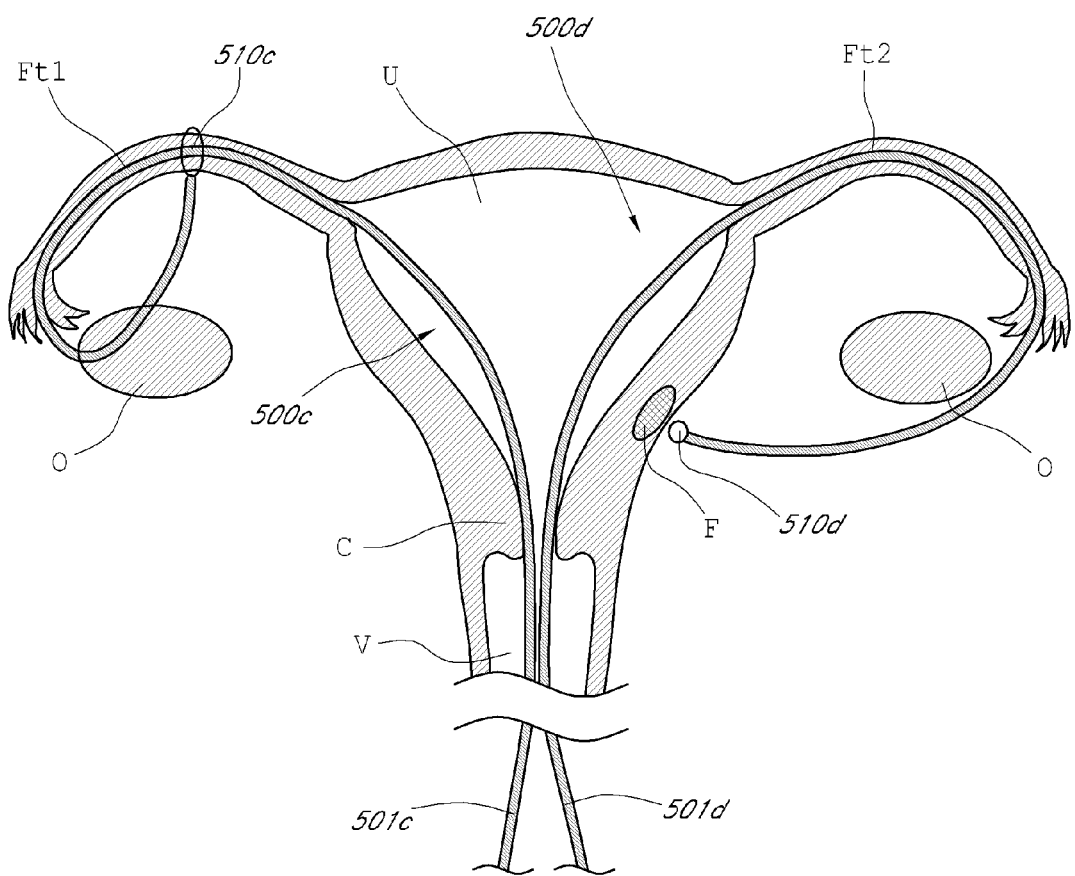
FIG. 6 illustrates a side sectional view of an exemplary method consistent with the present invention, wherein a first treatment device has been advanced through the cervix and a fallopian tube and is accessing the outside of a fallopian tube, and a second treatment device has been advanced through the cervix and a fallopian tube and is accessing the outside of the uterus proximate a fibroid.

Referring now to FIG. 6, a preferred embodiment of a trans-fallopian method for performing a gynecologic procedure is illustrated. A first treatment device 500c is inserted through the vaginal canal of the vagina V, through the cervix C, through the uterus U and through a fallopian tube FT1 to a location outside the fallopian tube FT1. First treatment device 500c includes an elongate shaft, shaft 501c which includes on its distal end occluding assembly 510c, shown as a snaring assembly but alternatively an occluding clip placement assembly or an occlusive drug delivery assembly. Shaft 501c preferably includes one or more pull wires, for manipulation, and alternatively or additionally may be advancable over a previously placed guidewire. Shaft 501c preferably includes a handle on its proximal end, not shown but preferably including one or more controls such as pull wire controls and a control to synch up the snare of treatment element 510c. Treatment element 510c is shown having snared a portion of fallopian tube FT1 such as to occlude fallopian tube FT1 in a sterilization procedure.

A second treatment device 500d is inserted through the vaginal canal of the vagina V, through the cervix C, through the uterus U and through a fallopian tube FT2 to a location outside the fallopian tube FT2 and proximate subserosal fibroid F. In an alternative embodiment, the hysteroscopic morcellator of the present invention is placed into the cervix C, and first treatment device 500c and/or second treatment device 500d are passed into the uterus U via the hysteroscopic morcellator. In another alternative embodiment, one or more of the previous devices resides outside of the hysteroscopic morcellator, such as to stabilize that device in the uterus. Second treatment device 500d includes an elongate shaft, shaft 501d which includes on its distal end treatment element 510d, a fibroid treating element such as a morcellator, an ablative element, a lysing or excising element, or another device used to remove or denature fibroid tissue. Shaft 501d preferably includes one or more pull wires, for manipulation, and alternatively or additionally may be advancable over a previously placed guidewire. Shaft 501d preferably includes a handle on its proximal end, not shown but preferably including one or more controls such as pull wire controls and a control to activate fibroid treating element 510d.

Treatment catheter 500c and/or treatment catheter 500d may include one or more functional elements as has been described in detail hereabove. Preferably, a navigation and/or visualization element is employed to introduce the ends of the devices, especially to the target location once exiting the fallopian tube. Preferably treatment catheter 500c and/or treatment catheter 500d include one or more visualization markers, such as visible and non-visible markers; radiopaque markers; magnetic markers; ultrasonically reflective markers; and combinations thereof. Similar to the trans-vaginal-wall methods of FIGS. 5 and 5A, the trans-fallopian tube approach of FIG. 6 may be used to perform numerous procedures including but not limited to: uteral wall procedures (e.g. the fibroid F treatment shown); fallopian tube procedures (e.g. the tubal ligation shown); ovary procedures (e.g. egg harvesting); cancer treatment procedures; pain treatment procedures; other tissue treatment or removal procedures, and intra-abdominal procedures.

Figure 7:
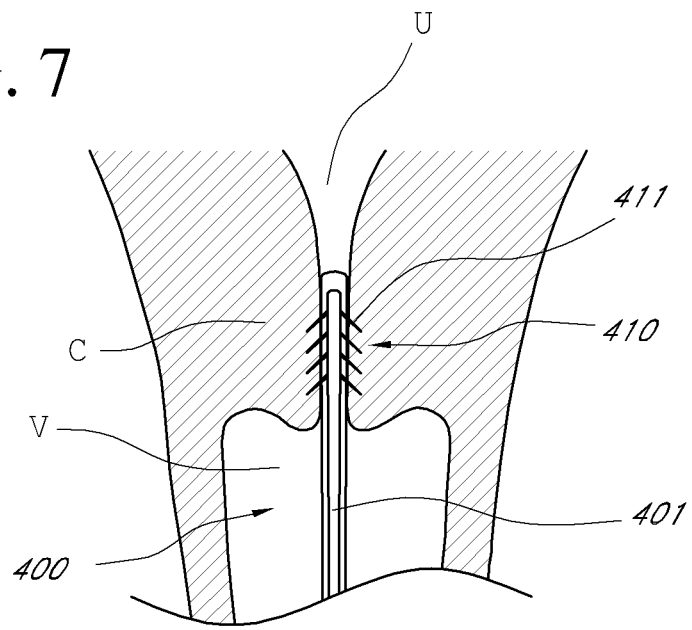
FIG. 7 illustrates a side sectional view of an exemplary drug delivery device consistent with the present invention, wherein the device is deployed in the cervix of the patient and integral needles are deployed into the cervical wall.

Referring now to FIG. 7, a preferred embodiment of a drug delivery device of the present invention is illustrated. Drug delivery device 400 is shown having been inserted into through the vagina V and into the cervix C of a patient. Device 400 includes an elongate shaft 401 with, near its distal end, drug delivery assembly 410. Drug delivery assembly 410 includes needles 411 (e.g. Nitinol or stainless steel needles), shown deployed into the cervix C such as to deliver a drug to the cervix. Applicable drugs include anesthetics such as lidocaine, muscle relaxing drugs, and other drugs. Shaft 401 may include one or more lumens, such as a fluid delivery lumen to deliver a drug to needles 411 and a guidewire lumen for preferably advancing shaft 401 into the cervix C over a guidewire.

Figure 7A:
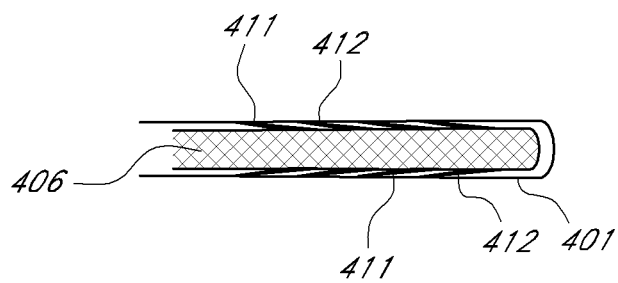
FIG. 7A illustrates a side sectional view of the drug delivery device of FIG. 7, wherein the needles are in the retracted position.
Figure 7B:
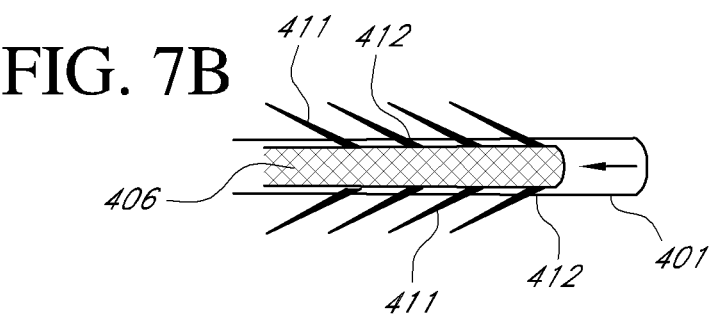
FIG. 7B illustrates a side sectional view of the drug delivery device of FIG. 7, wherein the needles are in an deployed position.
Figure 7C:
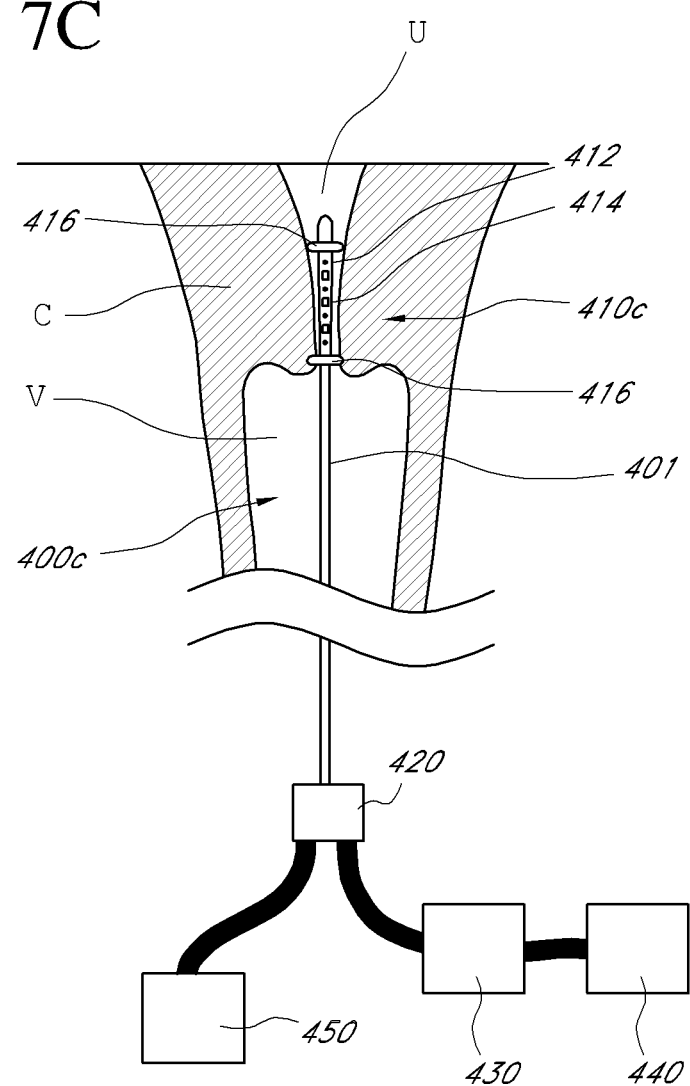
FIG. 7C illustrates a side sectional view of another exemplary drug delivery device consistent with the present invention, wherein the device includes a vacuum source and suction ports for attracting tissue toward a drug delivery element.

Referring now to FIG. 7A, the distal end of shaft 401 is shown. Shaft 401 surrounds inner shaft 406, which can be controllable advanced and retracted by the clinician such as via one or more controls on a proximal handle of drug delivery device 400, handle and controls not shown. Needles 411 are undeployed, contained within the wall of shaft 401 with their distal tips oriented toward and proximate to exit holes 412. Referring now to FIG. 7B, inner shaft 406 has been retracted, causing needles 411 to deploy, passing through exit holes 412. Such retraction would cause needles 411 to penetrate into neighboring tissue, such as cervical tissue when shaft 401 is placed in the cervix when inner shaft 406 is retracted. In order to support the intended motion, needles 411 may be flexible or may be connected to a flexible hinge.

Referring now to FIG. 7D, a preferred embodiment of a drug delivery device of the present invention is illustrated. Drug delivery device 400c is shown having been inserted into through the vagina V and into the cervix C of a patient. Device 400c includes an elongate shaft 401 with, near its distal end, drug delivery assembly 410d. Shaft 401 includes occluding rings 416 on either end of drug delivery assembly 410c. Occluding rings 416 and drug delivery assembly 410c have been positioned in the cervix C such that drug delivered through one or more exit holes 412 of drug delivery assembly 410c will contact cervical tissue. Applicable drugs include anesthetics such as lidocaine, muscle relaxing drugs, and other drugs.

Occluding rings 416 are sized to form a seal in the cervix, such as to allow elevated pressure delivery of drugs and/or to provide a vacuum seal in the area surrounding drug delivery element 410c. In an alternative embodiment, shaft 401 includes a single occluding ring 201, such as at a location of the proximal occlusion ring shown. In another alternative embodiment, occluding rings 201 may have a controllable diameter, such as rings comprising an inflatable balloon, balloon inflation lumen and inflation port not shown.

Drug delivery element 410c further includes one or more suction ports 414. Suction ports 414 and occluding rings 416 are configured such that when a vacuum is applied to suction ports 414, the cervical (or other neighboring) tissue is pulled toward the exit holes 412 of drug delivery element 410c, such that the efficacy of drug delivered through exit holes 412 is enhanced. Exit holes 412 and suction ports 414 are connected to independent hollow conduits that travel from drug delivery element 410c to port 420 on the proximal end of drug delivery device 400c. Port 420 fluidly connects to drug reservoir 430, which in turn is pressurized by pressure reservoir 440 (such as a $CO_2$ pressure source) such that fluid can flow through shaft 401 to exit holes 412. Port 420 is also fluidly connected to vacuum generator 450 such that suction can be transferred through shaft 401 (in a separate conduit than is connected to drug reservoir 430) to suction ports 414.

In an alternative embodiment, drug delivery element further includes an iontophoretic element, not shown but configured to enhance drug delivery into the tissue surrounding drug delivery element 410c. In another alternative embodiment, shaft 401 includes a lumen to support over-the-wire delivery.

Figure 8:
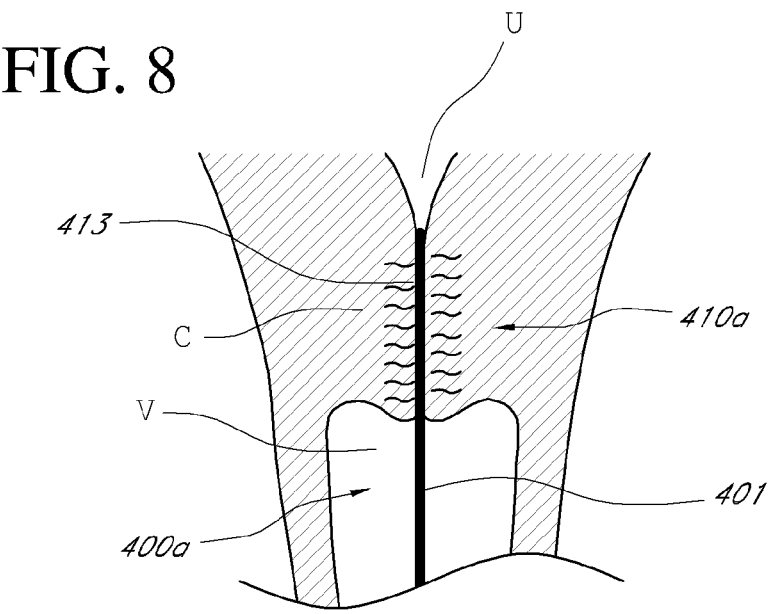
FIG. 8 illustrates a side sectional view of another exemplary drug delivery device consistent with the present invention, wherein the device is deployed in the cervix of the patient and integral exit holes allow fluid to pass into the cervical wall.

Referring now to FIG. 8, another preferred embodiment of a drug delivery device of the present invention is illustrated. Drug delivery device 400a is shown having been inserted into through the vagina V and into the cervix C of a patient. Device 400a includes an elongate shaft 401 which includes drug delivery assembly 410a near its distal end. Drug delivery assembly 410a includes exit holes needles 413, sized and configured to deliver a drug to the cervix. Applicable drugs include anesthetics such as lidocaine, muscle relaxing drugs, and other drugs. Shaft 401 may include one or more lumens, such as a fluid delivery lumen to deliver a drug to exit holes 413 and a guidewire lumen for preferably advancing shaft 401 into the cervix C over a guidewire.

Figure 8A:
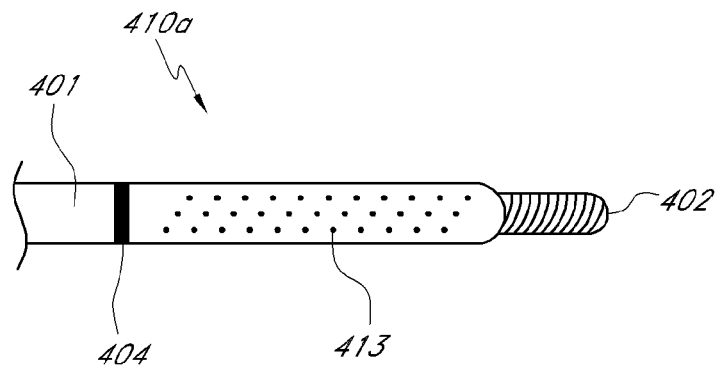
FIG. 8A illustrates a side view of the distal end of the drug delivery device of FIG. 8, wherein the device is deployed over an occluding guidewire.
Figure 8B:
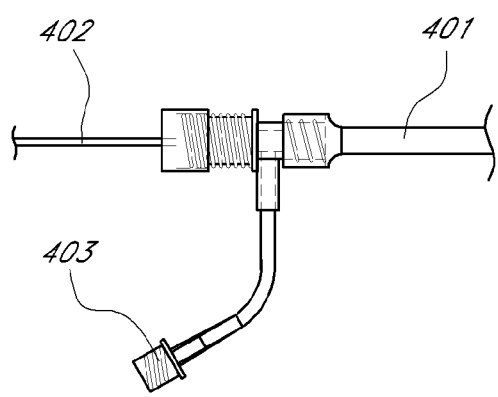
FIG. 8B illustrates a side view of the proximal end of the drug delivery device of FIG. 8A.

Referring now to FIG. 8A, the distal end of shaft 401 is shown. Shaft 401 surrounds an occluding guidewire 402. Shaft 401 can be controllably advanced and retracted by the clinician over guidewire 402. Proximal to exit holes 413 is marker 404, preferably a radiopaque or ultrasonically reflective marker used to position the exit holes 413 in the cervix C. Referring now to FIG. 8B, the proximal end of inner shaft 406 is shown wherein guidewire 402 exits the proximal end of the device. Infusion port 403 provides fluid access to the exit holes 413 such that drugs can be delivered via a syringe, infusion pump, or gravity feed system.

Figure 9:
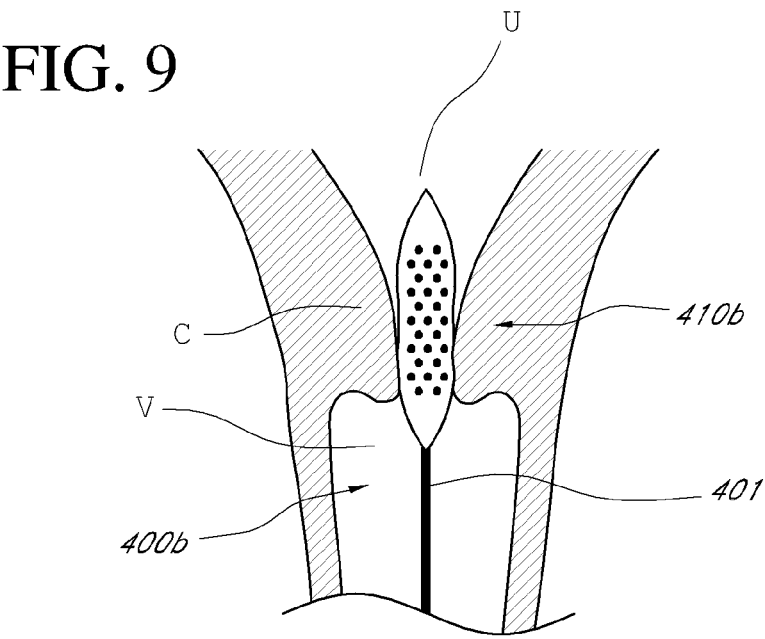
FIG. 9 illustrates a side sectional view of another exemplary drug delivery device consistent with the present invention, wherein the device is deployed in the cervix of the patient, an integral balloon has been inflated and integral exit holes in the balloon allow fluid to pass into the cervical wall.

Referring now to FIG. 9, another preferred embodiment of a drug delivery device of the present invention is illustrated. Drug delivery device 400b is shown having been inserted into through the vagina V and into the cervix C of a patient. Device 400a includes an elongate shaft 401 with, near its distal end, drug delivery assembly 410b comprising a balloon with multiple exit holes which are sized and configured to deliver a drug to the cervix. Applicable drugs include anesthetics such as lidocaine, muscle relaxing drugs, and other drugs. Shaft 401 may include one or more lumens, such as a fluid delivery lumen to deliver a drug to exit holes 413 and a guidewire lumen for preferably advancing shaft 401 into the cervix C over a guidewire.

Figure 9A:
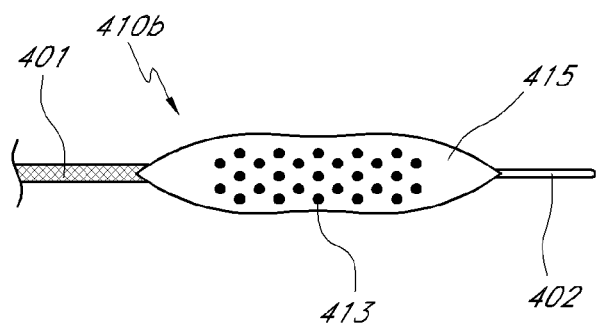
FIG. 9A illustrates a side view of the distal end of the drug delivery device of FIG. 9, wherein the device is deployed over a guidewire and the balloon is inflated.
Figure 9B:
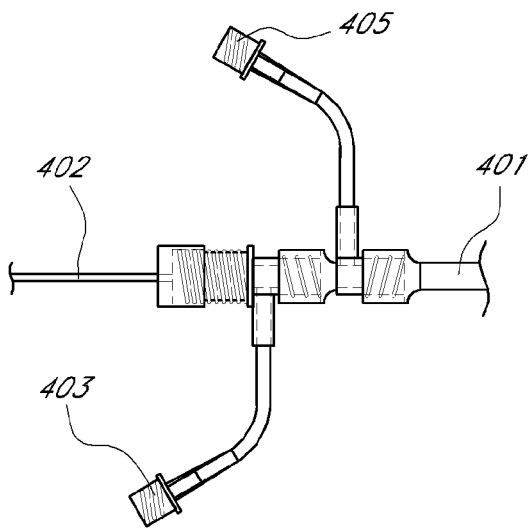
FIG. 9B illustrates a side view of the proximal end of the drug delivery device of FIG. 9A.

Referring now to FIG. 9A, the distal end of shaft 401 is shown having been inserted over guidewire 402. Shaft 401 can be controllably advanced and retracted by the clinician over guidewire 402. Drug delivery assembly 410b includes an inflatable balloon 415, preferably a dual balloon construction with exit holes 413 in the outer balloon. Referring now to FIG. 9B, the proximal end of inner shaft 406 is shown wherein guidewire 402 exits the proximal end of the device. Infusion port 403 provides fluid access to the exit holes 413 such that drugs can be delivered via a syringe, infusion pump, or gravity feed system. Inflation port 406 provides inflation access to balloon 415, such as to an inner balloon portion of balloon 415. In an alternative embodiment, an enhanced drug delivery element is integral to balloon 415, such as an iontophoretic element for precision controlled drug delivery. In another alternative or additional embodiment, balloon 415 is inflated to dilate or partially dilate the cervix C of the patient.

Figure 10:
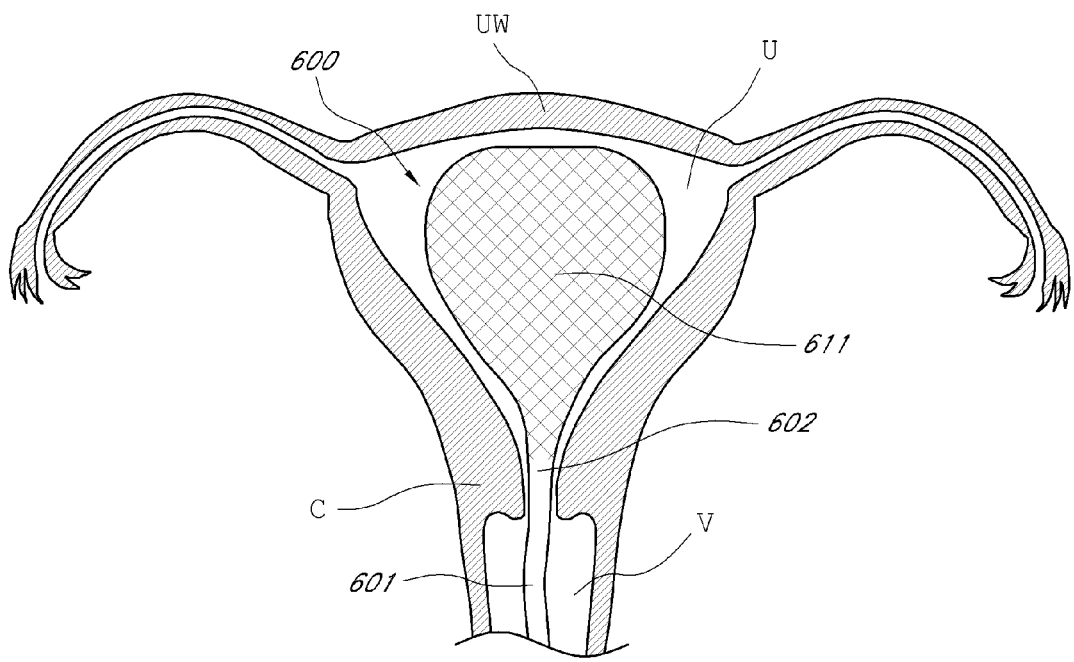
FIG. 10 illustrates a side sectional view of an exemplary scaffolding device consistent with the present invention, wherein the device has been deployed in the uterus of a patient.

Referring now to FIG. 10, a preferred embodiment of a scaffolding device of the present invention is illustrated. Scaffolding device 600, and the other distension devices of the present invention, are preferably inserted into the uterus of a patient such that the scaffolding assembly preferably distends the uteral cavity to a volume equivalent to that which would be attained via a liquid distention media at a pressure of at least 40 mm of HG but not greater than 100 mm HG and preferably approximating 70 mm Hg. Scaffolding device 600 is shown having been inserted into through the vagina V, through the Cervix C and into the uterus U of a patient. In an alternative embodiment, the hysteroscopic morcellator of the present invention is placed into the cervix C, and scaffolding device 600 is passed into the uterus U via the hysteroscopic morcellator. Scaffolding device 600 includes elongate shaft 601. Extending beyond the distal tip 602 of shaft 601 is deployable basket 611. Basket 611, shown in its fully expanded state, is preferably a resiliently biased foldable weave of filaments made of Nitinol. Manipulation of shaft 601 (e.g. via pull-wires not shown) and/or basket 611 can be performed by the clinician to exert forces against one or more portions of the uteral wall UW such as to distend or scaffold the uteral wall, to apply tamponade to a bleed, and combinations thereof. Basket 611 can be arranged in numerous shapes, such as to mimic the shape of the uterus or a portion of the uterus. The weaved filaments may be sized (e.g. diameter, length or width) to effectively cover a small proportional area (e.g. large "windows" between filaments) or they may be configured to cover a large proportion of the area (e.g. with a large profile and/or a covering).

Basket 611 may include a covering, on the inside or the outside of the resiliently biased structure, and the covering may be a partial covering. In a preferred embodiment, a clinician places a tamponade force on a bleeding tissue location with a covered portion of basket 611. In another preferred embodiment, a clinician reduces the amount of fluid used in a procedure by inserting a scaffolding device 600 that includes a covering of basket 611 (i.e. the basket occupies space in the uterus and/or limits fluid transfer from the portion of the uteral wall in contact with the balloon). Basket 611 and any associated coverings may be coated, impregnated or otherwise include one or more drugs, such as clotting agents and anesthetics. In a preferred embodiment, the drug may be "released" by the clinician on demand, such as by an integral iontophoretic delivery element (e.g. integral to basket 611), or by applying a force to an integral pressure activated drug depot (e.g. integral to basket 611). Basket 611 and any associated coverings may be coated or treated with one or more compounds to change a property such as lubricity and radiopacity. Avoiding or reducing the need for distension with fluid subsequently reduces the risk factors (e.g. intravasation) associated with that fluid delivery.

Figure 10A:
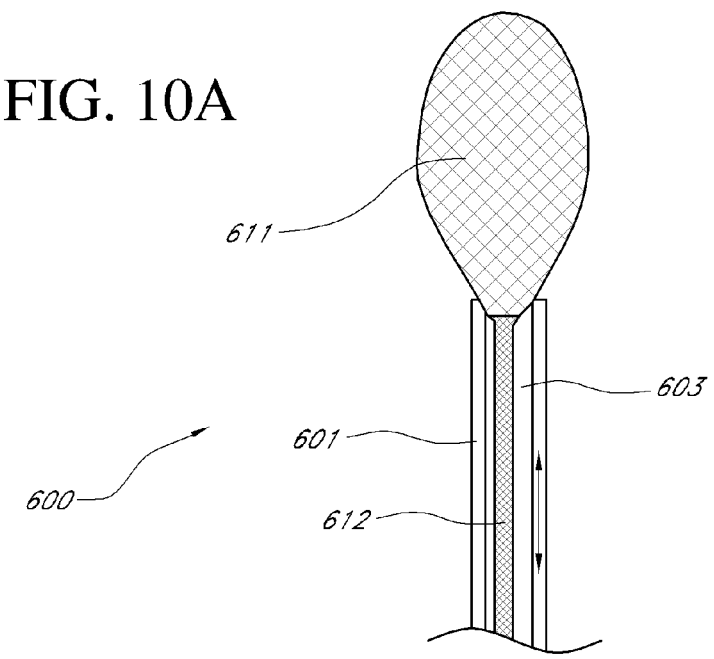
FIG. 10A illustrates a side sectional view of the scaffolding device of FIG. 10, wherein a control shaft has been near fully extended and a scaffold is partially deployed.

Referring now to FIG. 10A, a cross section of the distal portion of scaffolding device 600 is shown with basket 611 in a near-fully deployed state. Basket 611 is fixedly attached to control shaft 612 which is slidingly received by outer shaft 601 via lumen 603. The proximal end of shaft 601 is preferably attached to a handle, not shown, which includes one or more controls, also not shown but preferably including a control knob or lever that can precisely advance and retract control shaft 612. Retraction of control shaft 612 causes basket 611 to withdraw into the lumen 603 of shaft 601 and transition to a radially compact state. Subsequent advancement of control shaft 612 causes bases 611 to exit lumen 603 and resiliently expand into the deployed state shown if FIG. 10. In an alternative embodiment, basket 611 includes mechanical expansion means to assist in radial expansion, such mechanical expansion means including an inflatable balloon inside or outside of basket 611, advancable push rods which exert radial forces upon different portions of basket 611 and/or other mechanical means. In this alternative embodiment, basket 611 may or may not be resiliently biased.

In a preferred embodiment, basket 611 can be expanded in the uterus (or other body cavity), and a procedure such as a tissue removal or denaturing procedure be performed "through" the weave of basket 611. Numerous one or more treatment or other devices, can be used by the clinician while scaffolding device 600 is in place in the uterus. In particular, tissue treatment devices (e.g. morcellators; radiofrequency, laser and cryogenic ablaters; and subsonic treatment devices) and drug delivery devices can perform their intended function, such as to treat tissue present in between the filaments (tissue in "window) of basket 611. In another preferred embodiment, scaffolding device 600 is used to treat uteral prolapse. In yet another preferred embodiment, a separate balloon catheter is inserted within balloon 611, such as to occupy space and/or apply additional force to the uteral wall. In yet another alternative embodiment, one or more portions of basket 611 can be energized (e.g. deliver RF energy to tissue) in order to treat tissue, which may avoid the need for a second device.

Figure 10B:
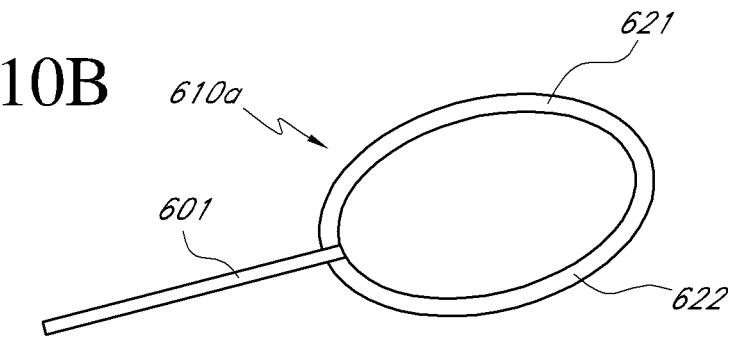
FIG. 10B illustrates a perspective view of an exemplary scaffolding device consistent with the present invention, wherein the scaffolding assembly comprises two resiliently biased arms.

Referring now to FIG. 10B, another preferred embodiment of a scaffolding device of the present invention is illustrated. Located on the distal end of elongate shaft 601 is a deployable scaffolding assembly 610a. Scaffolding assembly 610a is configured to scaffold open a body cavity such as the uterus, while also providing an operating space to perform one or more procedures such as tissue removal. Scaffolding assembly 610a make be arranged in one or more shapes, such as to conform to specific body areas such as the contour of uteral wall. Scaffolding assembly 610a comprises two resiliently biased arms, first arm 621 and second arm 622. These arms, preferably constructed of Nitinol, are configured to be radially compressed when drawn into the distal end of a tube, such as the lumen of the hysteroscopic morcellator of the present invention (see FIG. 10D). Shaft 601 preferably includes one or more lumens, such as a lumen to slidingly receive a guidewire for over-the-wire delivery. In an alternative embodiment, first arm 621 and/or second arm 622 include light source means, such as light provided through a window optically connected to a fiber optic cable, light provided by one or more LEDs and/or light provided via a chemoluminescent solution.

Figure 10C:
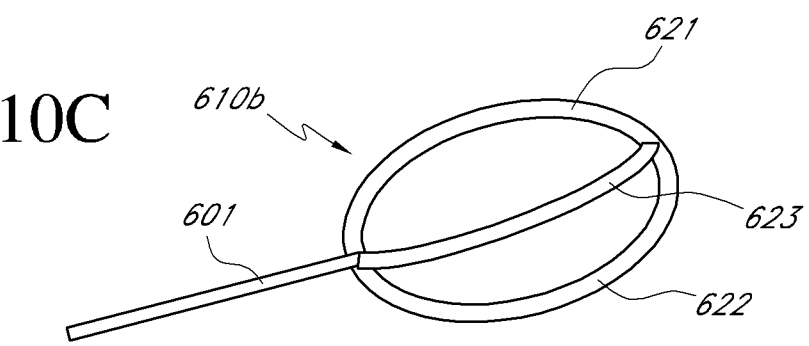
FIG. 10C illustrates a perspective view of an exemplary scaffolding device consistent with the present invention, wherein the scaffolding assembly includes three resiliently biased arms.

Referring now to FIG. 10C, another preferred embodiment of a scaffolding device of the present invention is illustrated. Located on the distal end of elongate shaft 601 is a deployable scaffolding assembly 610b. Scaffolding assembly 610b (similar to is configured to scaffold open a body cavity such as the uterus, while also providing an operating space to perform one or more procedures such as tissue removal. Scaffolding assembly 610b make be arranged in one or more shapes, such as to conform to specific body areas such as the contour of uteral wall. Scaffolding assembly 610b comprises three resiliently biased arms, first arm 621, second arm 622 and third arm 623. In an alternative embodiment, four or more arms may be included. These arms, preferably constructed of Nitinol, are configured to be radially compressed when drawn into the distal end of a tube, such as the lumen of the hysteroscopic morcellator of the present invention (see FIG. 10D). Shaft 601 preferably includes one or more lumens, such as a lumen to slidingly receive a guidewire for over-the-wire delivery. In an alternative embodiment, first arm 621, second arm 622 and/or third arm 623 include light source means, such as light provided through a window optically connected to a fiber optic cable, light provided by one or more LEDs and/or light provided via a chemoluminescent solution.

Figure 10D:
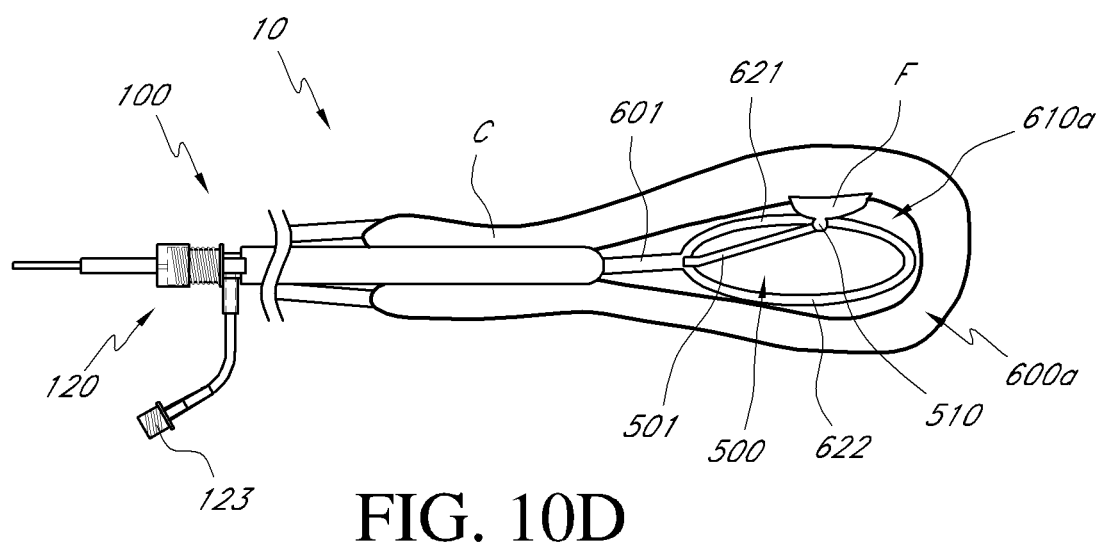
FIG. 10D illustrates a side sectional view of the scaffolding device of FIG. 10B, wherein the scaffolding device has been inserted through an introducer of the present invention and has its distal portion in the uterus of a patient.

Referring now to FIG. 10D, a preferred embodiment of a system 10 consistent with the present invention is illustrated. System 10 includes hysteroscopic morcellator 100, scaffolding device 600a and treatment device 500. Hysteroscopic morcellator 100d includes sheath 110, device insertion port 120 and fluid transfer port 123, all of similar construction to similar components of hysteroscopic morcellators 100a, 100b and 100c, 100d, 100e, 100f and 100g hereabove. Hysteroscopic morcellator 100 has been placed and advanced such that its distal portion resides within cervix C and its distal end provides access within uterus U of a patient.

Scaffolding device 600a, of similar construction to the scaffolding device of FIG. 10B, has been advanced through a lumen of hysteroscopic morcellator 100 such that the distal end of shaft 601 and scaffold assembly 610a (fully expanded) reside within the uterus U such that a scaffolding force is applied to the uteral wall along a plane relatively perpendicular to the cross section shown in FIG. 10D. First arm 621 and second arm 622 have been positioned at locations away from uteral fibroid F as shown in FIG. 10D. Treatment device 500 has been coaxially advanced through a lumen of shaft 601 of scaffolding device 600a such that the distal portion of shaft 501 resides with uterus U. At the distal end of shaft 501 is treatment element 510, such as a morcellator or other tissue treatment element. Via deflection means, not shown but preferably a pull-wire internal to shaft 501, treatment element 510 has been brought in close proximity to fibroid F, also as shown in FIG. 10D.

In an alternative embodiment, treatment catheter 500, scaffolding device 600a and/or hysteroscopic morcellator 100 include a visualization apparatus such as a camera to visualize inside uterus U, such as when clear fluid is introduced into uterus U via port 123. Light may be provided, as has been described in detail hereabove, from a functional element integral to the distal portions of treatment catheter 500 (e.g. proximate a camera which is proximate treatment element 510), scaffolding device 600a (e.g. in one or more of arms 621 and 622) and/or hysteroscopic morcellator 100 (e.g. a forward beam light source) such as to improve the image provided to the clinician via the integral camera. In one embodiment, the camera is an infrared camera and heated and/or cooled solutions are utilized to increase the contrast in the infrared image (tissue temperature differences) and reduce or eliminate the need for an external light source.

In the performance of one or more gynecologic and urologic procedures, such as a tissue removal or other treatment procedure, scaffolding device 600a and treatment device 500 are repositioned, such as to scaffold a different part of the uterus or to access a different portion of tissue, respectively. In a preferred embodiment, a second scaffolding device is inserted through hysteroscopic morcellator 100, simultaneous with or at a different time than scaffolding device 600a resides within hysteroscopic morcellator 100. In another preferred embodiment, a second treatment device is inserted through hysteroscopic morcellator 100, simultaneous with or at a different time than treatment device 500 resides within hysteroscopic morcellator 100.

Figure 11:
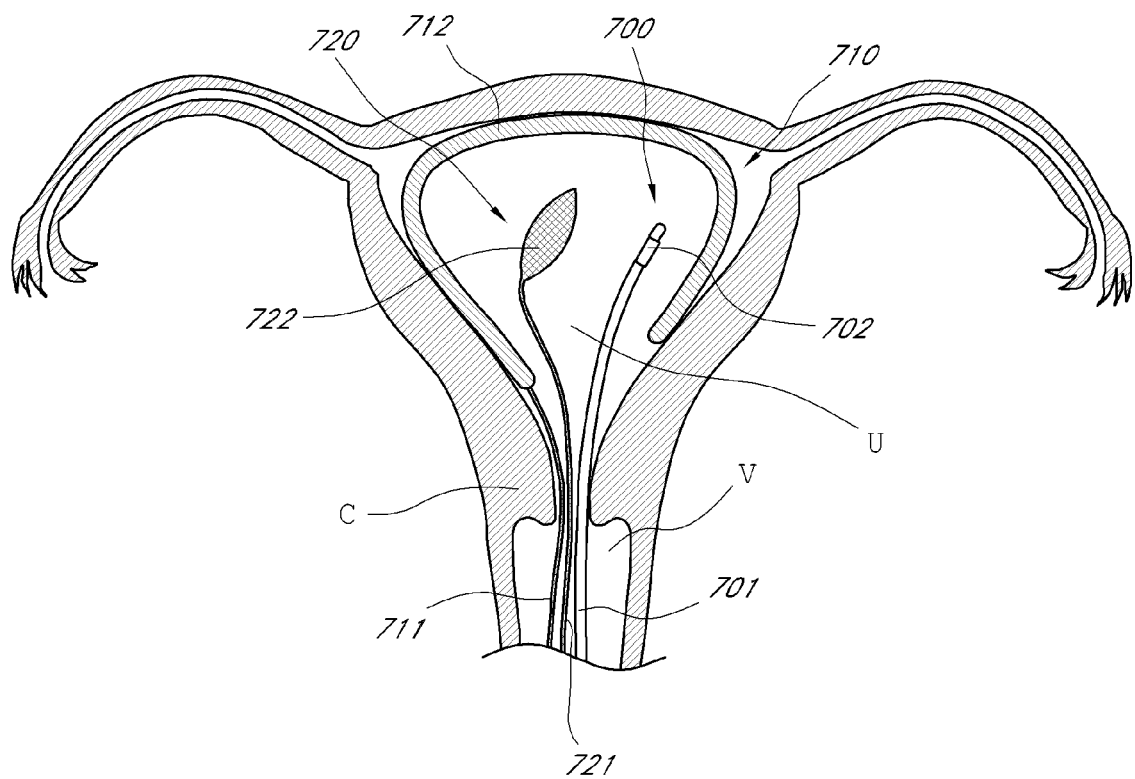
FIG. 11 illustrates a side sectional view of an exemplary visualization apparatus consistent with the present invention, wherein a camera device, a first light source and a second light source have been advanced into the uterus of a patient.

Referring now to FIG. 11, a preferred embodiment of a visualization apparatus of the present invention is illustrated. Camera device 700 consists of shaft 701, preferably an elongate shaft with a deflectable tip, which includes camera assembly 702 in its distal end portion. Camera assembly 702, which preferably includes a sealed lens or window on its outer portion, includes one or more configurations as has been described hereabove, including one or more components or assemblies selected from the group consisting of: lenses including filtering lenses, wide angle lenses, gradient lenses and focusing lenses; mirrors; image sensors such as a CCD module; MEMS gyroscopes (such as to detect and accommodate for motion); MEMS mirrors; light sources such as LEDs; strain gauges (such as to detect and accommodate for motion); accelerometers (such as to detect and accommodate for motion); fiber optic cable for image transfer; other optical or image processing components and combinations thereof. Camera assembly 702 may be arranged as an endoscope, and/or may involve different technologies such as MEMS actuators, CCD modules and motion detectors which are configured to provide a stabile image to a clinician despite camera movement. In an alternative embodiment, an output port, not shown, is located proximate to camera assembly 702 such that saline or other biocompatible liquid media in fluid communication with the output port can be flushed by camera assembly 702 such as to clear debris and improve image quality. Camera device 700 provides an image to a display, not shown but preferably a laptop screen as has been described in reference to FIG. 5, such as through an electrical and/or optical connection on a handle of camera device 700.

The visualization apparatus of FIG. 11 further includes a first light source 710 which is independent (e.g. independently maneuverable) from camera device 700. First light source 710 includes shaft 711, preferably an elongate shaft with a deflectable tip, which includes light emitting element 712 at its distal end. Light emitting element 712 is a tubular structure which can be shaped, via pull wire technology described above and/or via plastic deformation (e.g. plastically deformable wire included within light emitting element 712) such as to wrap around the uterus as shown in FIG. 11. Light emitting element 712 is preferably a self-contained light source, such as an array of light emitting diodes that are surrounded by a window such as a diffracting or light-scattering lens. In an alternative embodiment, light emitting element 712 does not include a light source, but rather consists of a viewing window in optical communication with one or more fiber optic cables which in turn connect to a light source, the light source being integral to first light source 710 (such as in a handle of the device) or external and optically connected to first light source 710. Light emitting element 712, or a separate light source that supplies light emitting element 712, is connected to a source of electrical power such as a battery (e.g. a battery in a handle of the device). In an alternative embodiment, light emitting element 712 emits light from a chemoluminescent solution (e.g. a chemoluminescent solution that is mixed on demand by the clinician, such as by one or more controls on the handle of the device). This light generating solution, as in found in commercially available "lightsticks", may be contained (sealed compartment) within light emitting element 720, or be optically connected to element 720 via a fiber optic cable. In an alternative embodiment, the chemoluminescent solution is introduced into light emitting element 720 via an infusion lumen. In another alternative embodiment, both a chemoluminescent solution and another source of light (e.g. LED light) are provided by light emitting element 720.

The visualization apparatus of FIG. 11 further includes a second light source 720 which is also independent (e.g. independently maneuverable) from camera device 700. Second light source 720 includes shaft 721, preferably an elongate shaft with a deflectable tip, which includes light emitting element 722 at its distal end. Light emitting element 722 is a balloon structure which can be inflated and deflated by the clinician, shown in the inflated or partially inflated state in FIG. 11. Light emitting element 722 is preferably a self-contained light source, such as a vessel into which chemoluminescent solution is delivered, as has been described hereabove. Alternatively, one or more light emitting diodes that are surrounded by a covering (the balloon) which is configured as a diffracting or light-scattering lens. In an alternative embodiment, light emitting element 722 does not include a light source, but rather consists of a viewing window (the balloon) in optical communication with one or more fiber optic cables which in turn connect to a light source, the light source being integral to second light source 720 (such as in a handle of the device) or external and optically connected to second light source 720. Light emitting element 722, or a separate light source that supplies light emitting element 722, may be connected to a source of electrical power such as a battery. In the preferred embodiment, light emitting element 722 emits light from a chemoluminescent solution (e.g. a chemoluminescent solution that is mixed on demand by the clinician and injected into the balloon of light emitting element 722, such as by one or more controls on the handle of the device) and does not require the source of electrical power. In an alternative embodiment, both a chemoluminescent solution and another source of light (e.g. LED light) are provided by light emitting element 722.

Camera device 700, first light source 710 and second light source 720 have had their distal ends placed through the cervix C and into the uterus C of a patient. In an alternative embodiment, the hysteroscopic morcellator of the present invention is placed into the cervix C, and camera device 700, first light source 710 and/or second light source 720 are passed into the uterus U via the hysteroscopic morcellator. In another alternative embodiment, one or more of the previous devices resides outside of the hysteroscopic morcellator, such as to stabilize that device in the uterus. Each device preferably includes a handle on their proximal end, not shown but preferably including one or more controls including but not limited to: knobs or levers to manipulate one or more pull wires configured to manipulate the distal portions of the associated device; a control to zoom in or zoom out an image; a control to focus an image; a control to stabilize an image; a control to energize a light source; a control to change the light intensity of a light source (e.g. via change to energy supplied); a control to deliver a drug; a control to change the speed of a tissue removal assembly; a "Kill-switch" control to stop motion of a component immediately; other controls and combinations thereof.

In addition to the above controls, each handle may include one or more ports, such as ports selected from the group consisting of: a valved port such as a cracking pressure valved port, a two-way valved port and a duckbill valved port; a Tuohy-Borst valve; a fluid stasis valve; a device insertion port such as a port configured to accept a treatment device of the present invention; an infusion lumen access port such as an infusion lumen in fluid communication with a drug reservoir, exit port or other component of a drug delivery element; a balloon inflation lumen access port; other ports and combinations thereof. In a preferred embodiment, camera device 700, first light source 710 and/or second light source 720 include one or more integral functional elements such as a drug delivery element or other functional element as have been described hereabove. In a preferred embodiment, the functional element is an integral inflatable balloon, not shown but preferably in a distal portion of the device and configured to: occupy space in the uterus, deflect the distal end of the associated device by applying a force to the uteral wall; apply tamponade force to the uteral wall, or distend the uterus.

The distal portions of camera device 700, first light source 710 and second light source 720 may be manipulated in the uterus U such as to perform a secondary function including but not limited to: applying a tamponade force to a portion of the uteral wall (e.g. a perforation or bleed); to distend the uterus; and combinations thereof. The distal portions of camera device 700, first light source 710 and second light source 720 have an "effective" outer diameter (e.g. the ID of an appropriate sheath 110 of the present invention) less than 9 mm, preferably between 5 and 8 mm, and more preferably less than 6 mm.

Figure 12:
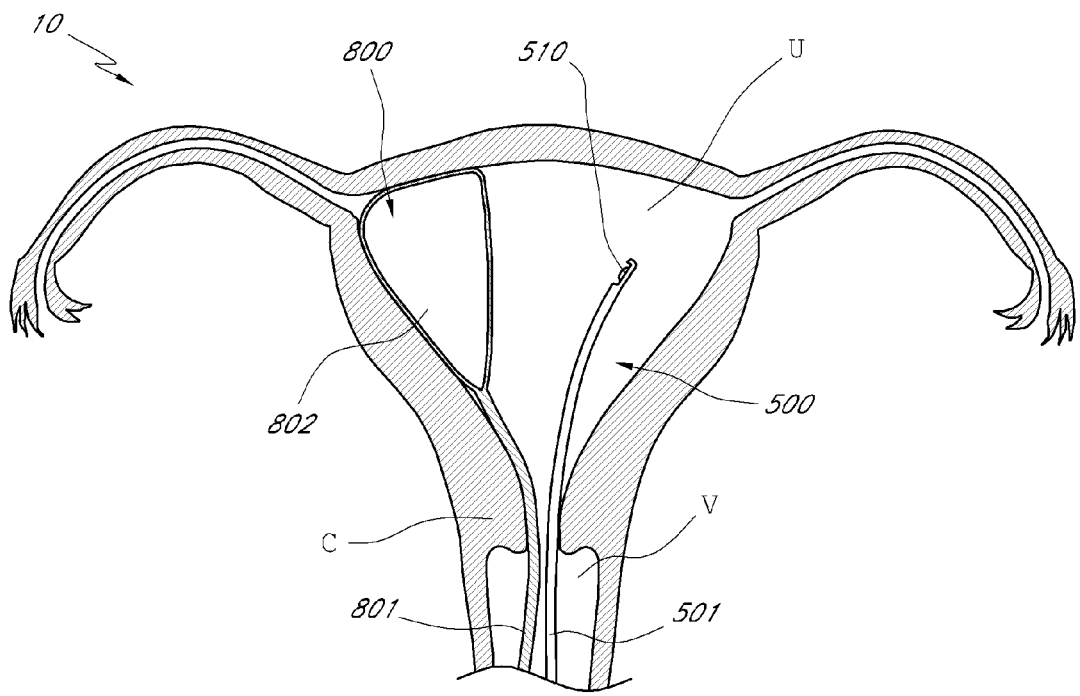
FIG. 12 illustrates a side sectional view of an embodiment of a system consistent with the present invention, wherein a uteral volume occupying device and a treatment device have each been advanced into the uterus of a patient.

Referring now to FIG. 12, a preferred embodiment of a volume occupying device of the present invention is illustrated. Volume occupying device 800 consists of shaft 801, preferably an elongate shaft with a deflectable tip, which includes volume occupying balloon 802 in its distal end portion. Inflation of balloon 802 is accomplished by administering fluid such as saline from an inflation port, not shown but preferably on a handle on the proximal end of device 800. Balloon 802 may be a compliant balloon such expands to variable volumes based on the fluid pressure, or a non-compliant balloon configured to expand to a fixed volume, relatively independent of fluid pressure. Balloon 802 is preferable includes nylon and/or PET materials. Balloon 802 is configured to assume a shape when inflated that approximated the shape of the uterus or a portion of the space of the uterus, as shown in FIG. 12. Inflation of balloon 802 is performed to accomplish one or more of the following functions: distend uterus U; effectively "cover" a portion of tissue surface area of uterus U such that fluids internal to uterus U will not be absorbed by or otherwise pass through that covered portion of tissue; apply a tamponade force to a portion of the uteral wall (e.g. a bleed or puncture site); occupy space of the uterus to reduce injected fluid volume; and other functions. In a preferred embodiment, device 800 performs at least two functions listed immediately hereabove. In another preferred embodiment, device 800 performs the function of distending tissue (e.g. the uteral wall) as well as limiting the transfer of fluids into or through that tissue.

Also shown in FIG. 12 is treatment catheter 500, including an elongate shaft 501 and a treatment element 510 near the distal end of shaft 501. Treatment catheter 500, for example a tissue removal or denaturing device or a drug delivery device, is being advanced such as to a location to the right and above balloon 802 of volume occupying device 800. Advantages of placement of volume occupying device 800 include the functions in the paragraph above, as well as creating a small "work area" for the clinician to navigate with treatment catheter 500.

In an alternative embodiment, the hysteroscopic morcellator of the present invention is placed into the cervix C, and volume occupying device 800 and/or treatment catheter 400 are passed into the uterus U via the hysteroscopic morcellator. In another alternative embodiment, one or more of the previous devices resides outside of the hysteroscopic morcellator, such as to stabilize that device in the uterus.

Figure 12A:
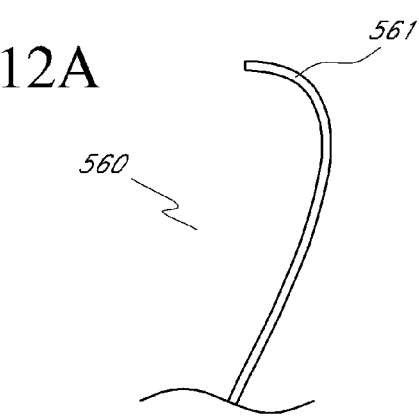
FIG. 12A illustrates a side view of an example of a wire shaping device consistent with the present invention.

Referring additionally to FIG. 12A, a shaping wire 560 including shape 561 near its distal end is shown. Shaping wire 560, preferably a heat-set shaped Nitinol wire, is configured to be inserted into a lumen of a device, such as a lumen of volume occupying device 800 or treatment catheter 500, lumens not shown. Clinician insertion of shaping wire 560 causes the distal portion of the device in which wire 560 is inserted, to change shape in a pre-determined manner. This shape-changing function allows the clinician to position one or more components of the devices (e.g. balloon 802 or treatment element 510), at a specific location within uterus U. In a preferred embodiment, shaping wire 560 is configured to be inserted into a lumen of one or more of the hysteroscopic morcellators, treatment catheters, distension devices, volume occupying devices, visualization apparatus, navigating apparatus or other devices of the present invention such as to modify the shape of a distal portion of the device.

Figure 13:
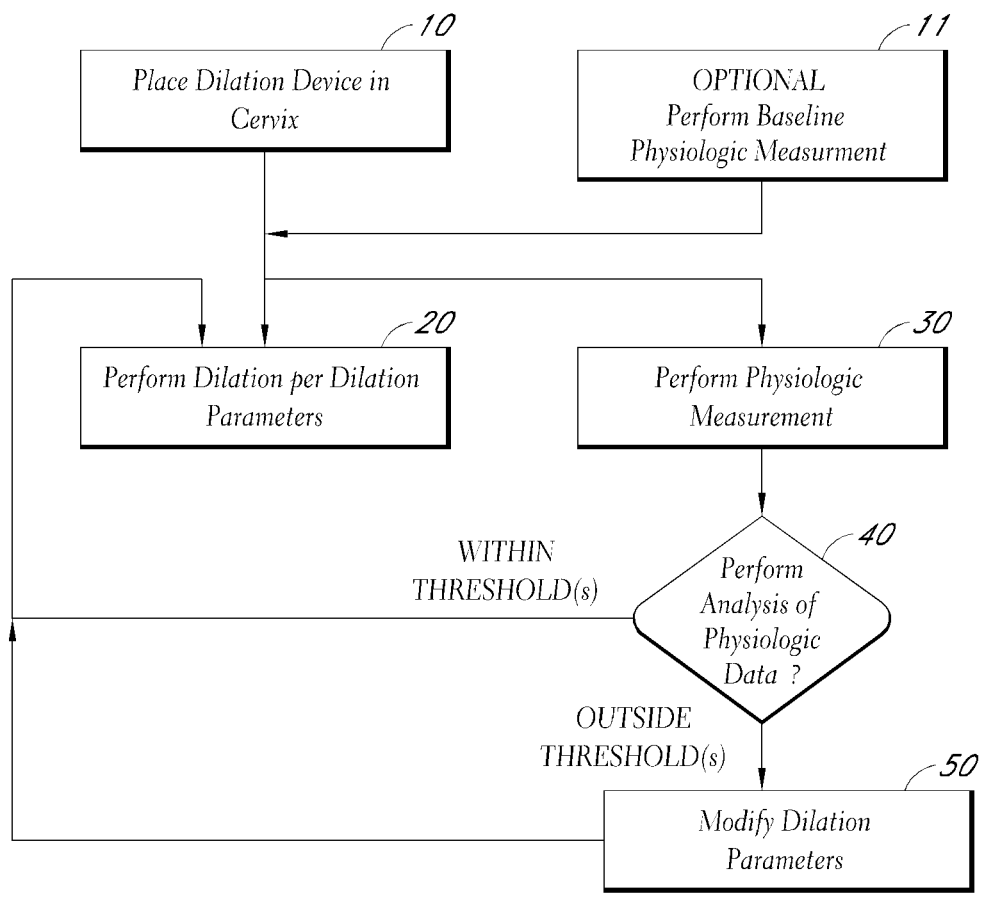
FIG. 13 illustrates a flow chart of an embodiment of a method of dilation, consistent with the present invention.

Referring now to FIG. 13, a preferred method and associated system of the present invention is disclosed. Numerous procedural steps listed below in reference to FIG. 13 have been described in detail throughout this specification. For brevity, the details of each step will not be repeated below but should be considered within the scope of the method and system of FIG. 13 as has been described hereabove.

Step 10 involves placing one or more devices to dilate the cervix of a patient. Prior to, during and/or shortly after the dilation of Step 10, Step 11 may be performed which is the measurement of one or more patient parameters, such as patient physiologic parameters. Patient physiologic parameters include but are not limited to: force exerted by or on tissue such as force exerted by or on the cervix as measured by a transducer integral to a cervical dilator; EKG; EEG; blood and blood gas parameters such as cell counts and $O_2$ saturation levels; glucose parameters; pH; blood pressure; respiration; and combinations thereof.

Subsequent to Step 10, Step 20 involves the dilation of the patient's cervix. The dilation is performed per a set of dilation parameters, such parameters including but not limited to: pressure of dilation such as balloon pressure; amount of dilation per unit time; pressure increase per unit time; rate of change of dilation per unit time; rate of change of pressure increase per unit time; duty cycle of discontinuous dilation (e.g. on and off times if dilation performed in discrete time segments); frequency of discontinuous dilation; other dilation parameters and combinations thereof.

Simultaneous with the performance of the dilation of Step 20, Step 30 is performed in which one or more patient parameters, as have been listed above in reference to Step 11, are taken. Step 40 is performed, in which the one or more parameters are analyzed and the results of the analysis is compared to a threshold. If a threshold is exceeded, that information is fed to the parameter modifying algorithm of Step 50, which in turn modifies one or more of the dilation of parameters of Step 20 (such as to decrease dilation pressure or stop dilation entirely). If the threshold is not exceeded, that information is fed back to the dilation control of Step 20 and no change is made.

For example, if one of the patient parameters collected in Step 30 is blood pressure, which may be an acceptable surrogate for pain level, when a previously determined blood pressure threshold is reached, dilation is reduced or stopped. The parameter analysis may be more sophisticated that comparing the physiologic measurement to a direct threshold, other analysis made additionally or alternatively be performed such as to look at rate of change of the parameter, or to analyze two or more parameters in combination: such as two or more of EKG, blood pressure and respiration.

In a preferred embodiment, a system is provided to automatically perform the parameter analysis of Step 40 and automatically modify the dilation parameters of Steps 50 and 20. In an alternative embodiment, the clinician may perform one or more steps, or perform a portion of one or more steps manually. In another preferred embodiment, one or more thresholds involved with the analysis are programmable by the clinician. In another preferred embodiment, the mathematical formulas of the analysis are programmable by the clinician.

The dilation performed in Step 20 may be accomplished with continuous application of pressure or discontinuously in discrete time segments. These discrete dilation time segments may be fractions of seconds, multiple seconds or even minutes. In a preferred embodiment, the analysis of the physiologic measurement is performed between dilation time segments, such that the subsequent dilation time segment is potentially modified (Step 50) due to the analysis performed in the previous "off" or no-dilation period.

The "smart" dilation system and method of FIG. 13 is preferably accomplished using a hysteroscopic morcellator of the present invention, such as hysteroscopic morcellator 100c of FIG. 1B which includes strain gauge 113 (output of strain gauge 113 is the measured physiologic parameter); or hysteroscopic morcellator 100e of FIG. 4 which includes pressure sensor 154 integral to dilating balloon 116 (output of sensor 154 is the measured physiologic parameter). Other devices of the present invention may include a functional element such as a pressure or other force sensor which provides an output signal that includes the physiologic data analyzed in Step 40.

In an alternative embodiment, the "smart" dilation system and method of FIG. 13 may deliver a drug based on the physiologic data analysis of Step 40, in addition to or alternative to modifying the dilation parameters in Step 50. In a preferred embodiment, a threshold for one analysis (based on one or more physiologic data) causes a drug to be delivered, and the threshold for a second analysis (based on similar or dissimilar physiologic data analysis used in the first analysis) causes a dilation parameter to be changed (including cessation of dilation).

It should be understood that numerous other configurations of the systems, devices and methods described herein could be employed without departing from the spirit or scope of this application. While the procedures described above have been described in terms of gynecological procedures, other applicable procedures can be incorporated without departing from the spirit and scope of the invention, particularly procedures applicable to both male and female patients.

The scaffolds and volume occupying element of the present invention comprise shapes and sizes that preferably allow both visualization (such as via an internal camera) and treatment (the performance of the intended clinical procedures, such as a tissue treatment procedure). Preferred shapes of these devices include but are not limited to: spherical; conical; trapezoidal; hemispherical; scallop-shaped; and combinations of the above such as a scaffolding device with a spherical portion and a conical portion. The size of the volume occupying elements of the present invention should be more than 5% of the volume of the cavity into which it is inserted (e.g. the uterus) and up to 100% of that space (e.g. to allow maximum viewing and working area without damaging tissue such as uteral wall or neighboring tissue).

The devices of the present invention may be provide in kits, such as kits that offer various size and shape scaffolding and volume occupying devices.

Each device (e.g. treatment device) could be used in various areas—not just Uterus Each device (e.g. treatment device) could be used in various procedure types such as: percutaneous, laparoscopic, MIS, open surgery The foregoing embodiments can be used in combination with any type of morcellator tip embodiment (with or without a vacuum), tissue removing devices, fibroid treating elements, tissue treatment devices, or tissue treatment elements, morcellator systems, morcellation means, denaturing devices, or other morcellating or other treatment devices.

Figure 14A:
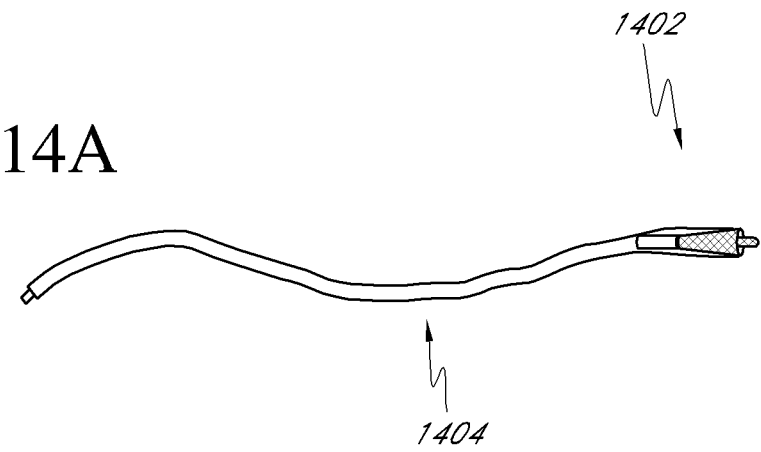
FIGS. 14A and 14B illustrate side views of an embodiment of a tubal sterilization device.
Figure 14B:
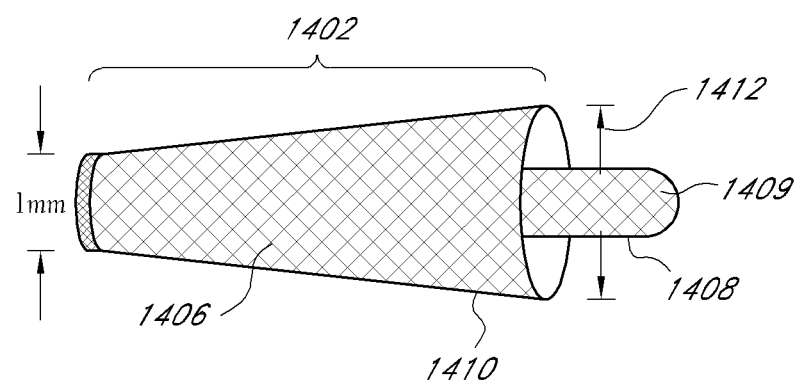

Referring to FIGS. 14A and 14B, according to another aspect of the invention, a tubal sterilization device 1402 (that can be attached and/or delivered using a catheter 1404) for occluding the fallopian tubes is disclosed that comprises expandable members 1406 whose construction may comprise either a coated element(s) and/or an integral component 1408 that uses a sclerosing agent to induce scarring within the lumen of the fallopian tube and an anchor such as a plurality of anchoring pins 1410. The integral component 1408 can have a bullet tip 1409 to enable easy insertion. The anchor 1410 can take advantage of the peristaltic contractions of the fallopian tube to drive the anchoring members into the intima of the fallopian tube. Thus, as the peristalsis tries to expel the plug, the anchoring pins 1410 will be driven into the intima anchoring it deeper and deeper. The plug and coated elements having an OD 1412 typically less than 3 mm, and preferably less than 2 mm, and preferably less than 1 mm, such as to prevent painful insertion and placement within the fallopian tube.

Referring to FIGS. 15A, 15B, 15C, 15D, and 15E, according to another aspect of the invention, a tubal sterilization device 1502 and method for occluding the fallopian tubes is disclosed that includes an anchored plug whose construction includes either a sclerosing agent coated element 1504 or an integral component 1506 made with a material impregnated with a sclerosing agent. In either embodiment, the sclerosing agent will cause a tissue reaction that will occlude the tube with the ingrowths of tissue. The device will occlude the fallopian tubes along a segment 1508 of at least 30 mm in length but preferably less than 20 mm and preferably less than 10 mm. Potential sclerosing agents include quinacrine, talc and doxycycline. The plug 1502 and coated elements having an OD 1510 typically less than 3 mm, and preferably less than 2 mm, and preferably less than 1 mm, such as to prevent painful insertion and placement within the fallopian tube.

The anchoring system is illustrated in FIGS. 15A, 15B, 15C, 15D, and 15E, and uses a combination of vacuum tissue manipulation via port 1512 that pulls tissue into a tissue gap such as an annular recess 1514 wherein mechanical pressure is applied via a clamping mechanism 1516. The clamping mechanism 1516 can permanently lock the movable member 1506 to the body 1518 for permanent fixation within the tube.

Figure 15A:
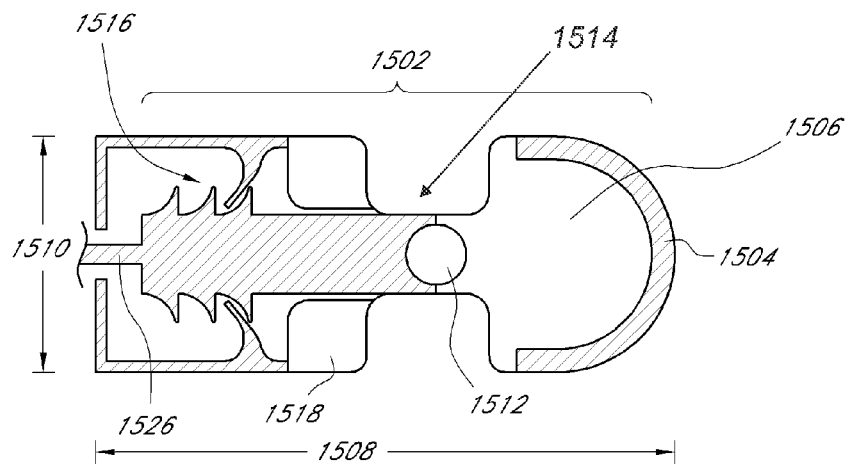
FIGS. 15A, 15B, 15C, 15D, and 15E illustrate side views of an embodiment of a tubal sterilization device.
Figure 15B:
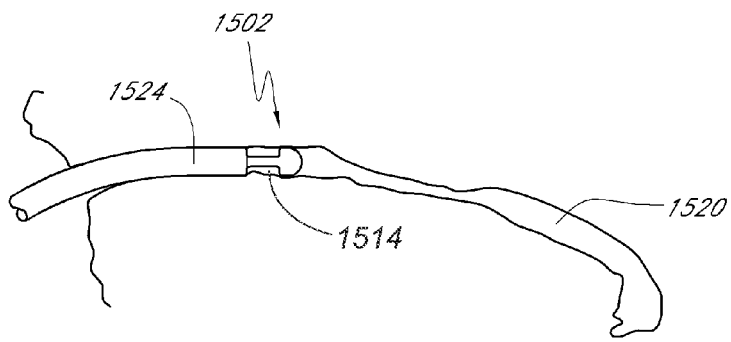
Figure 15C:
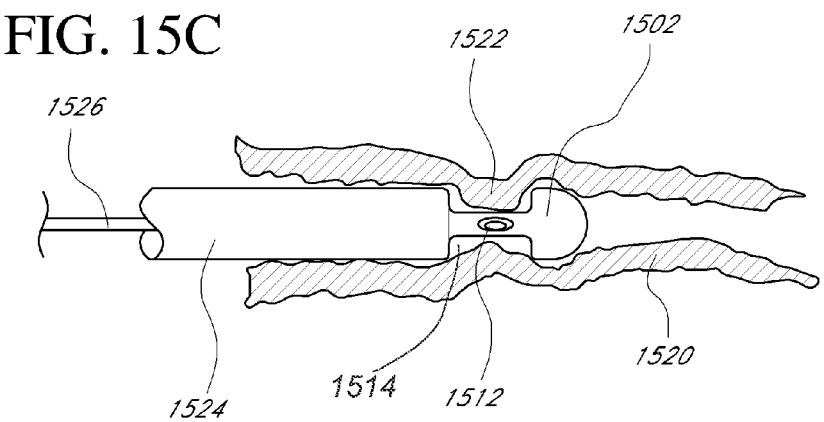
Figure 15D:
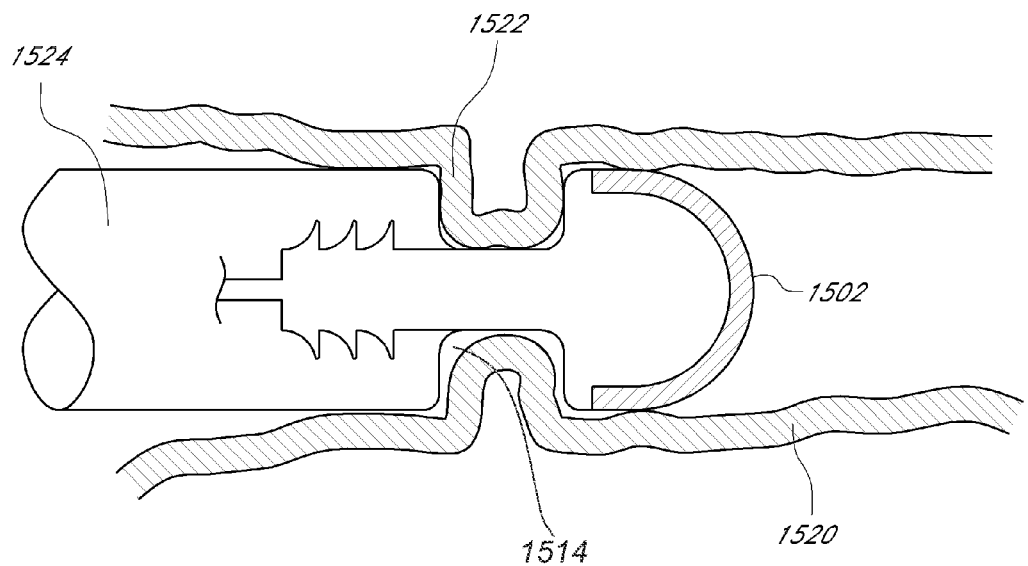
Figure 15E:
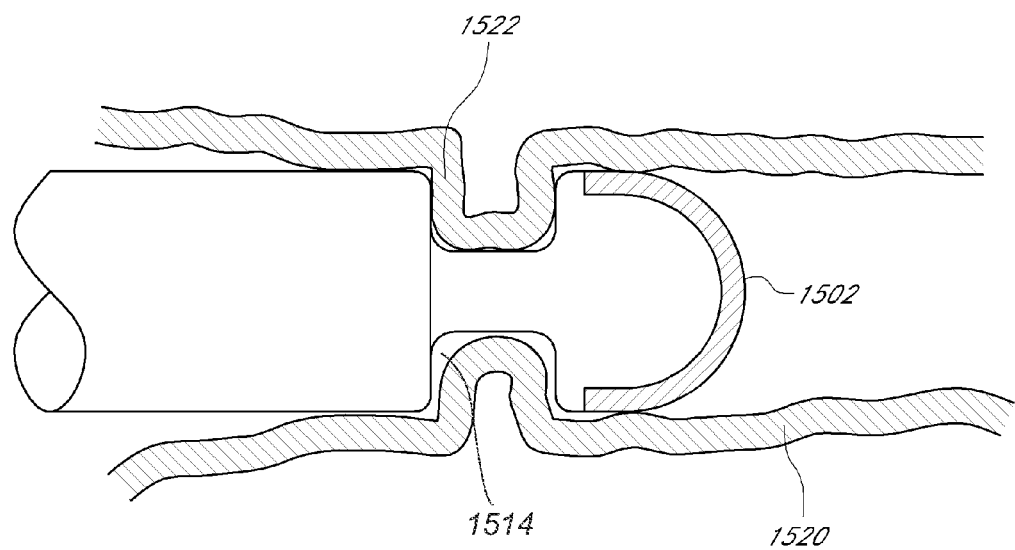

Referring to FIG. 15B, the sterilization device 1502 is advanced translumenally through a fallopian tube 1520, removably carried on the distal end of a deployment catheter 1524. Once positioned at the desired deployment site (see FIG. 15C), vacuum is applied to port 1512 by way of an elongate vacuum lumen extending throughout the length of the catheter 1524. An annular or semi-annular ring of tissue 1522 is drawn into the recess 1514.

The axial length of the tissue gap 1514 is shortened, such as by proximal traction on a pull wire 1526 (see FIG. 15A) which extends proximally throughout the length of the catheter 1524 to a proximal control (not illustrated). See FIG. 15D. Once compression has been applied to the plicated tissue 1522, the device 1502 is released from the distal end of the catheter 1524. See FIG. 15E. The catheter 1524 may thereafter be withdrawn.

Any of a variety of features may be added, to enhance the integrity of the connection between the device 1502 and the fallopian tube 1520. For example, opposing surfaces of the tissue gap 1514 may be provided with any of a variety of tissue engagement structures such as hooks or barbs. Alternatively, a tissue adhesive may be expressed via vacuum port 1512 after activation of the clamping mechanism 1516.

In reference to FIGS. 16A, 16B, 16C, 16D, 16E, 16F, 16G, and 16F, another embodiment of the tubal sterilization device and method is illustrated where an elastic band(s) 1602 are deployed (using a guidewire, catheter, introducer, or the like 1603) over an inverted tubal outer surface 1604 to ligate the fallopian tube. See FIG. 16H.

Figure 16A:
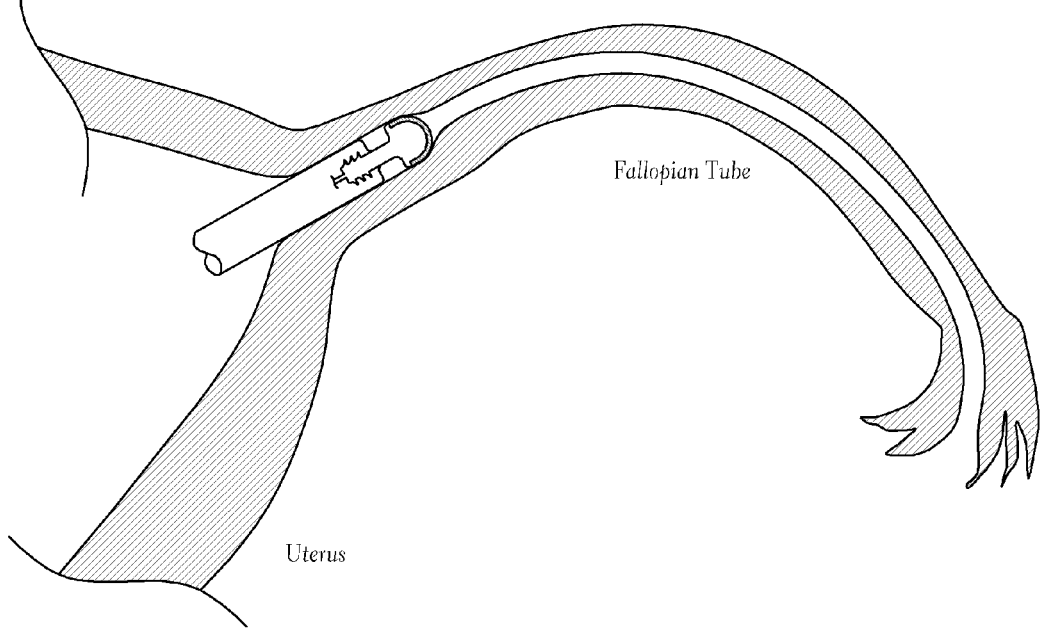
FIGS. 16A, 16B, 16C, 16D, 16E, 16F, 16G, and 16H illustrate side views of an embodiment of a tubal sterilization device.
Figure 16B:
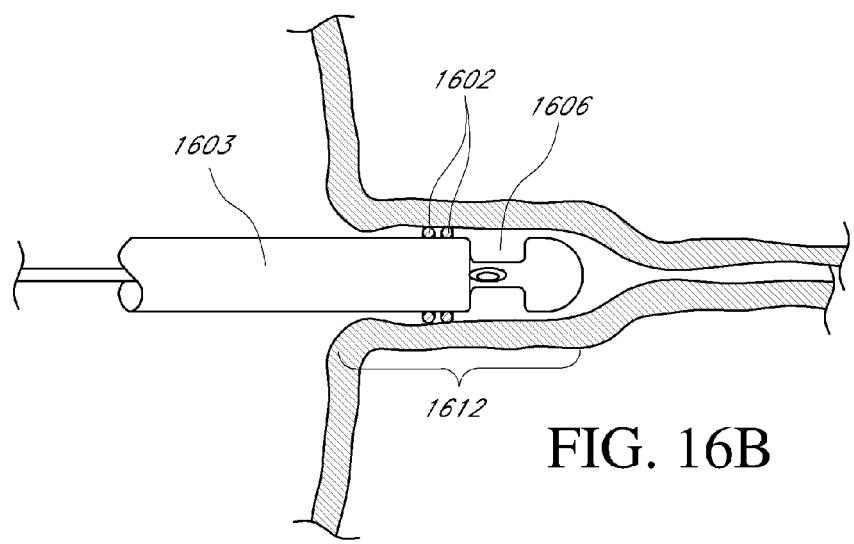
Figure 16C:
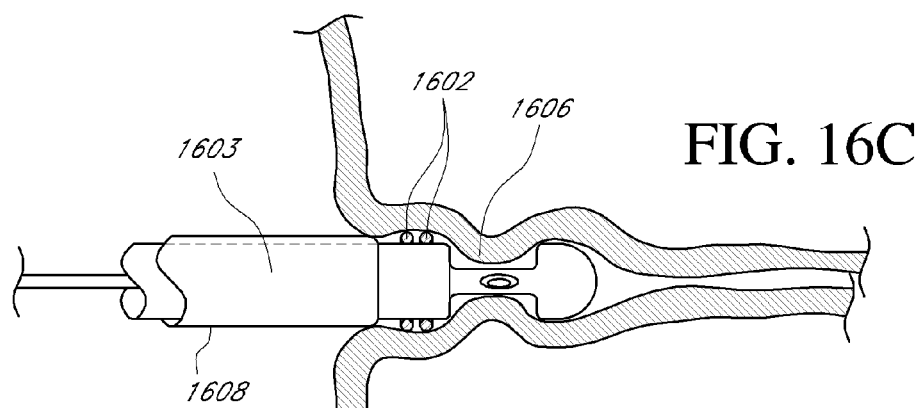
Figure 16D:
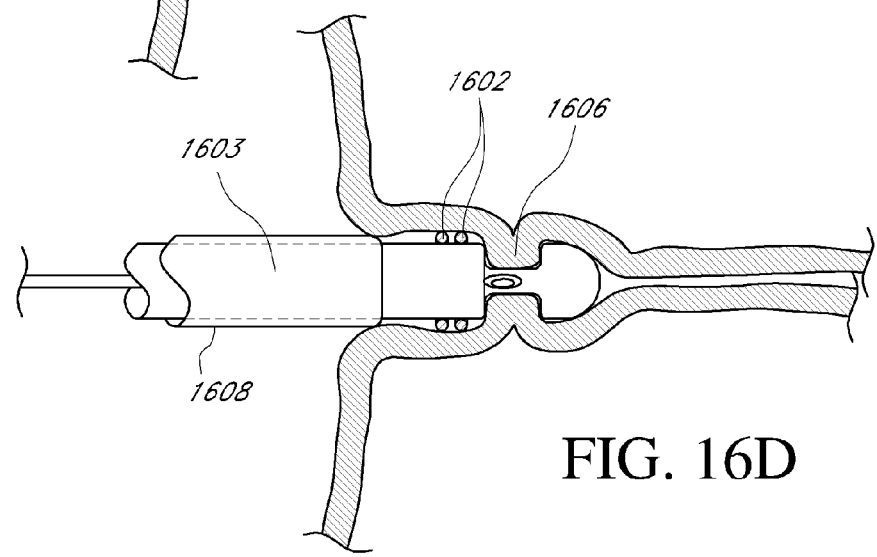
Figure 16E:
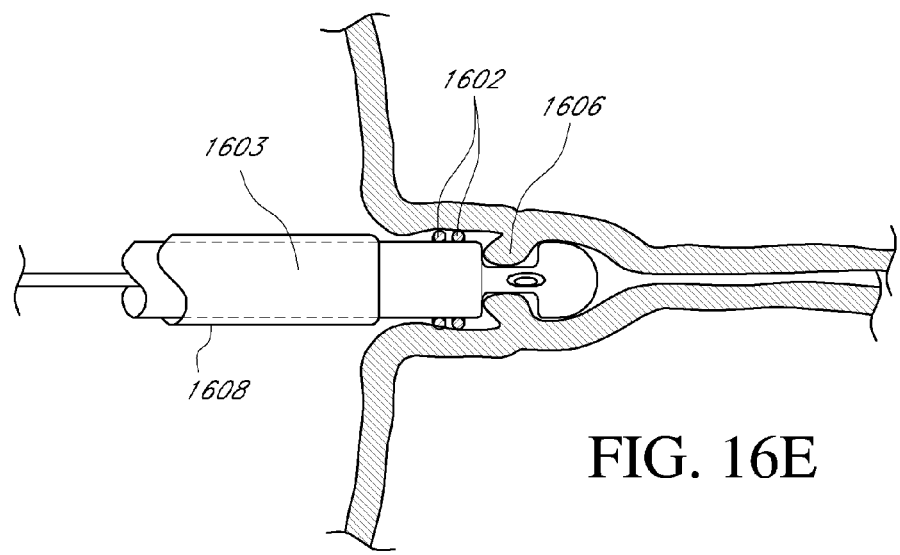
Figure 16F:
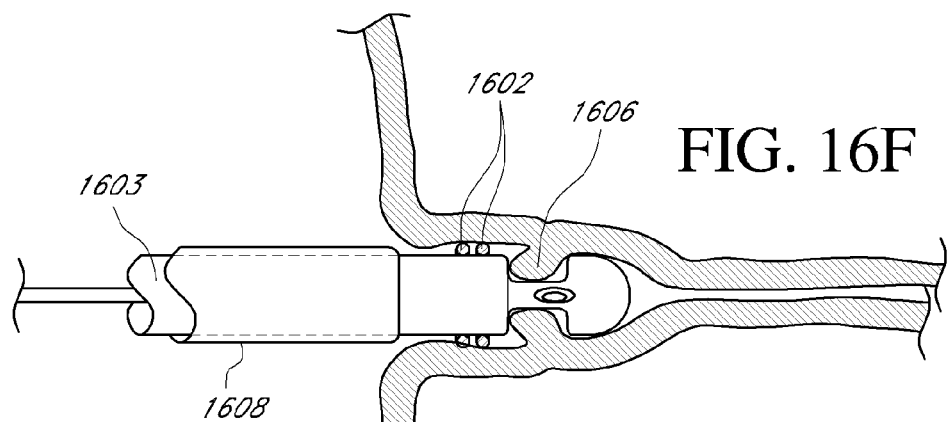
Figure 16G:
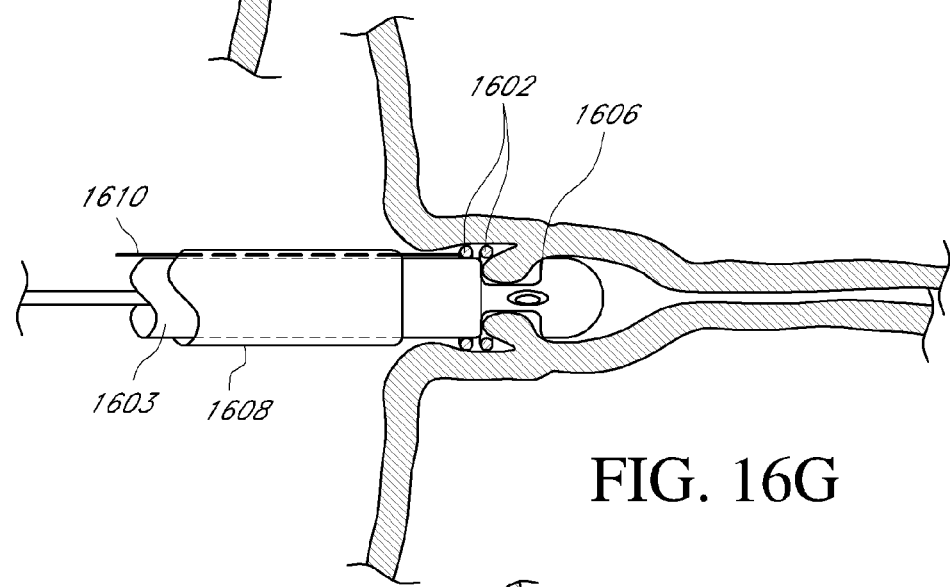
Figure 16H:
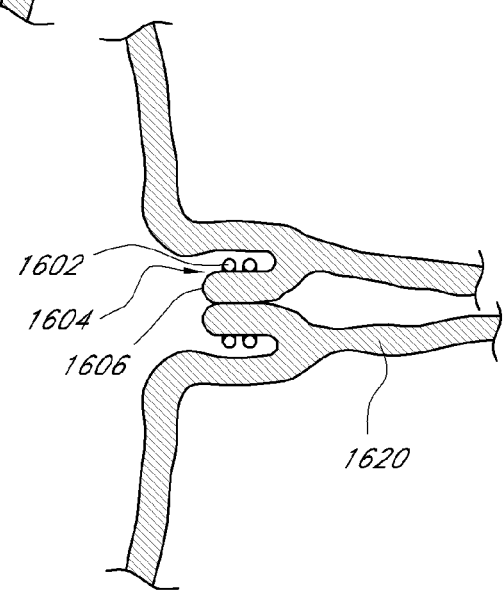

The tissue manipulation is completed with a suction grasping means 1606 such as an annular recess in communication with a vacuum lumen extending through the catheter as described herein. Once the tissue grasping is completed, the catheter 1603 is proximally retracted to draw the tissue plication into an inverted or prolapsed configuration as seen in FIG. 16H.

An outer tubular sleeve 1608 is concentrically slideably carried by the catheter 1103. The bands 1602 are releasably carried on the outside surface of the sleeve 1608. The sleeve 1608 is distally advanced over the plicated tissue 1606 and the bands 1602 are released onto the inverted tubal outer surface 1604.

The bands 1602 may be deployed using a string arrangement 1610 whereby the bands are rolled off the edge of the sleeve 1608. The banding device 1612 is then removed from the patient.

The ligation bands 1602 are made from a durable elastic material such as those utilized in the laparoscopic tubal ligation devices or the esophageal varices banding devices. The elastic bands 1602 will have a fully deployed inside diameter of less than 3 mm, and preferably less than 2 mm, and in some embodiments less than 1 mm in size, such as to cause complete occlusion of the fallopian tube. The banding device 1612 and method have the advantage of minimizing the efforts necessary to advance a device into the fallopian tube and undertake the deployment of an occluding member.

Figure 17A:
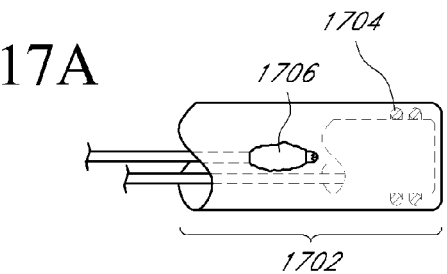
FIGS. 17A, 17B, 17C, 17D, 17E, 17F, and 17G, illustrate side views of an embodiment of a tubal sterilization device.
Figure 17B:
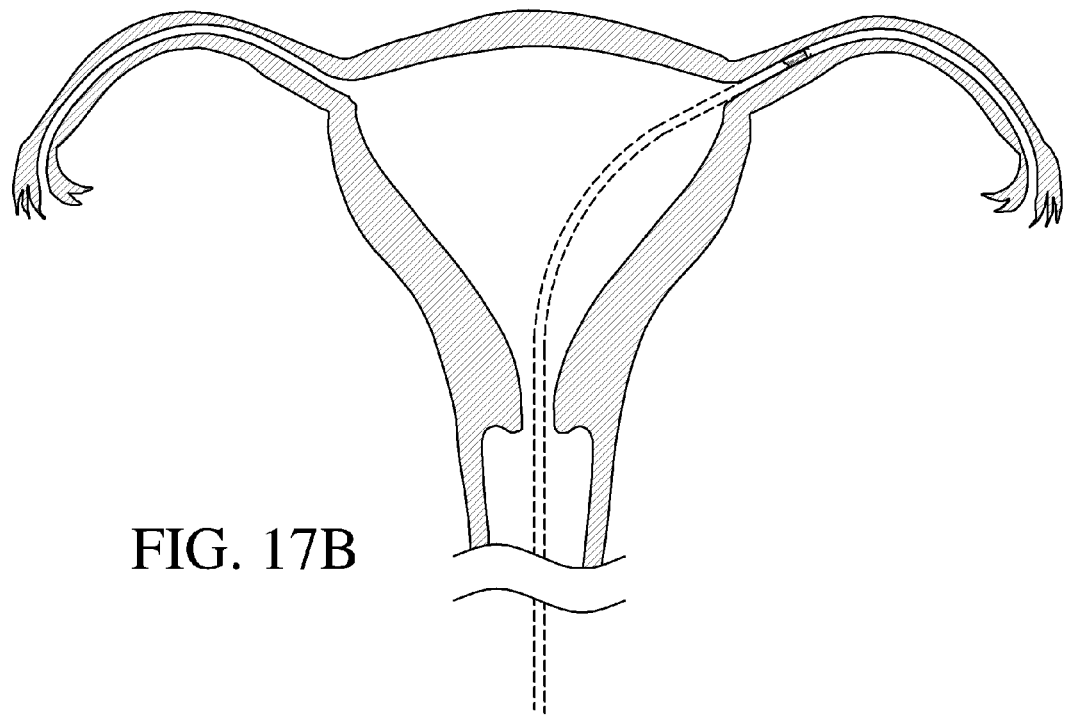
Figure 17C:
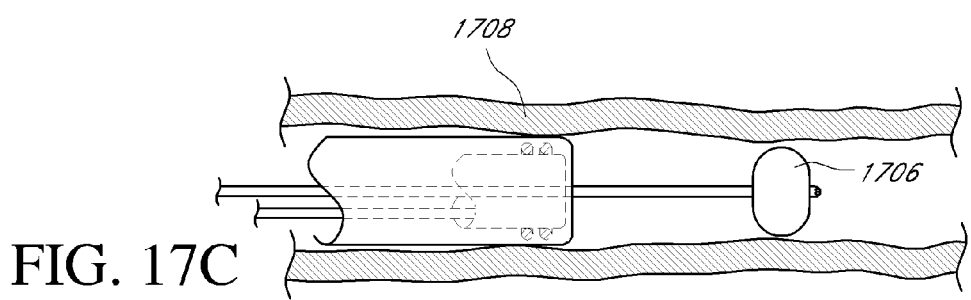
Figure 17D:
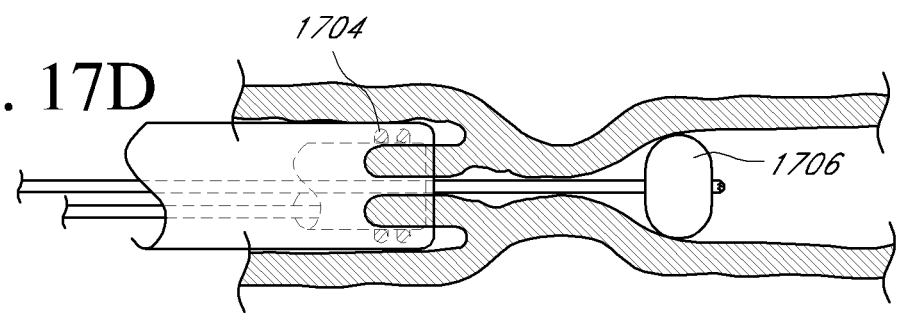
Figure 17E:
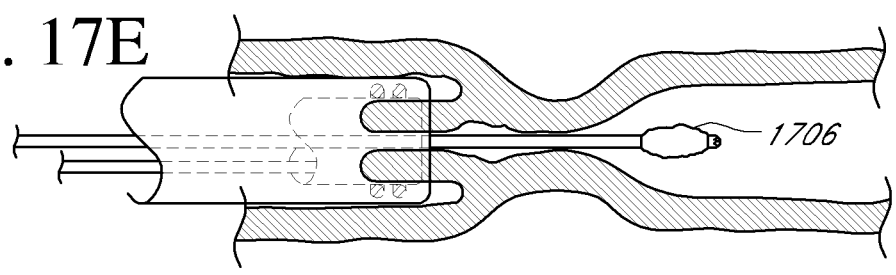
Figure 17F:
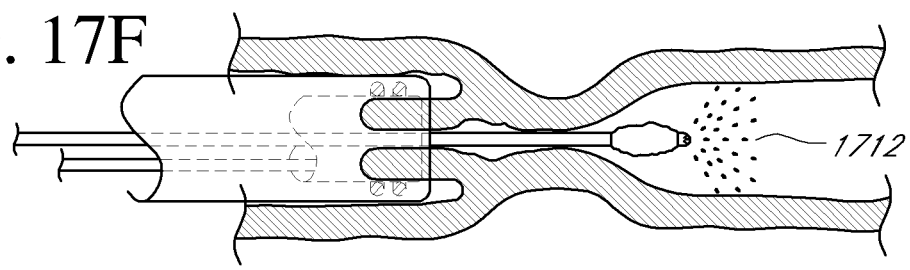
Figure 17G:
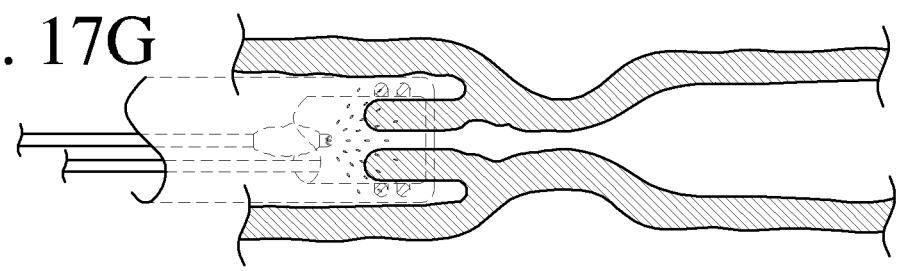

With regard to FIGS. 17A, 17B, 17C, 17D, 17E, 17F, and 17G, there is illustrated an embodiment of a tubal sterilization device 1702 and method where elastic band(s) 1704 are deployed over an inverted fallopian tube 1705 to ligate it. The tissue manipulation is completed with an occlusion balloon 1706 positioned within the fallopian tube 1708 as noted in FIG. 17C. Once the fallopian tube 1708 is occluded by the balloon 1706, suction is used to invaginate the fallopian tube 1708 into the tissue chamber 1710 as shown in FIG. 17D. Once the tissue has been invaginated into a plication 1705, the bands are released onto the inverted fallopian tube using a deployment means as described earlier with FIGS. 17A and 17B. The balloon is thereafter deflated. As a further insurance that the fallopian tube will be occluded, a light spray of sclerosing agent 1712 may be employed both distally and proximally, through a central lumen extending through the balloon catheter. The ligation bands 1704 are made from a durable elastic material such as those utilized in the laparoscopic tubal ligation devices or the esophageal varices banding devices. The elastic bands 1704 will have a fully deployed inside diameter of less than 3 mm, and preferably less than 2 mm, and in some embodiments less than 1 mm in size, such as to cause complete occlusion of the fallopian tube. The banding device 1702 and method 17A & 17B have the advantage of occluding the fallopian tube in a manner proven effective with open or laparoscopic approaches with a less invasive assess route of the cervix and uterus. Additionally, the use of the bands will provide an immediate closure of the fallopian tube lumen such that an acute assessment of tubal patency can be undertaken without the necessity of a 90 day birth control regime common with coiled occlusion devices.

Figure 18D:
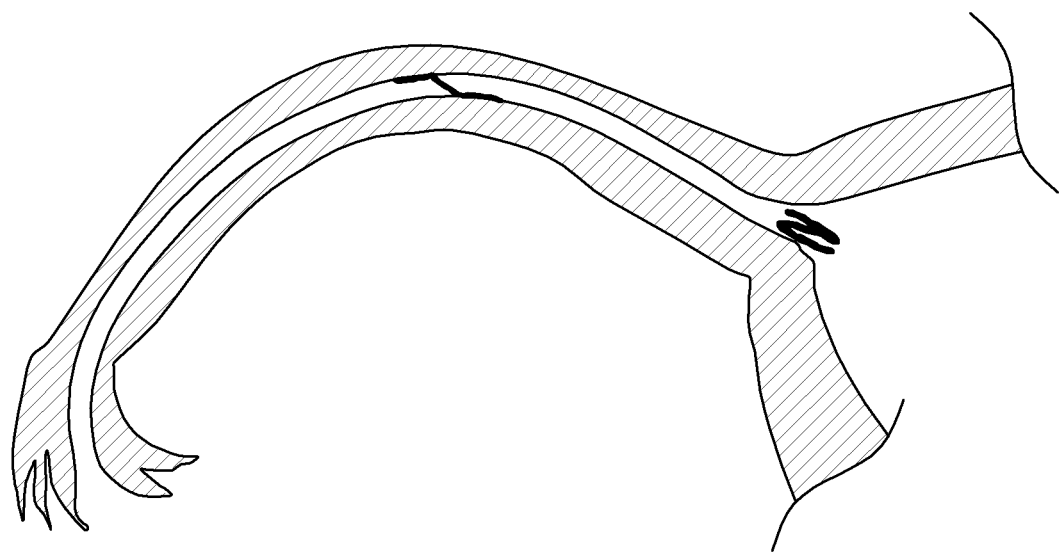

Referring to FIGS. 18-18F, there is illustrated a tubal sterilization device for occluding the fallopian tubes is disclosed that includes expandable members whose construction may include either a coated element or an integral component that uses a sclerosing agent to induce scarring within the lumen of the tube. The plug and coated elements having an OD typically less than 3 mm, and preferably less than 2 mm, and preferably less than 1 mm, such as to prevent painful insertion and placement within the fallopian tube.

Figure 19A:
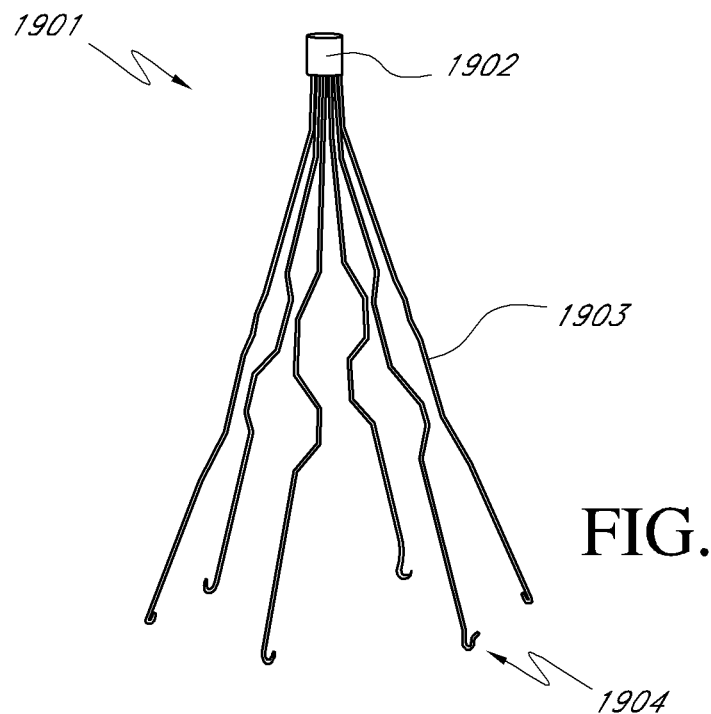
FIGS. 19A, 19B, and 20 illustrate an embodiment of an implant configured for placement in fallopian tubes to prevent pregnancy.
Figure 19B:
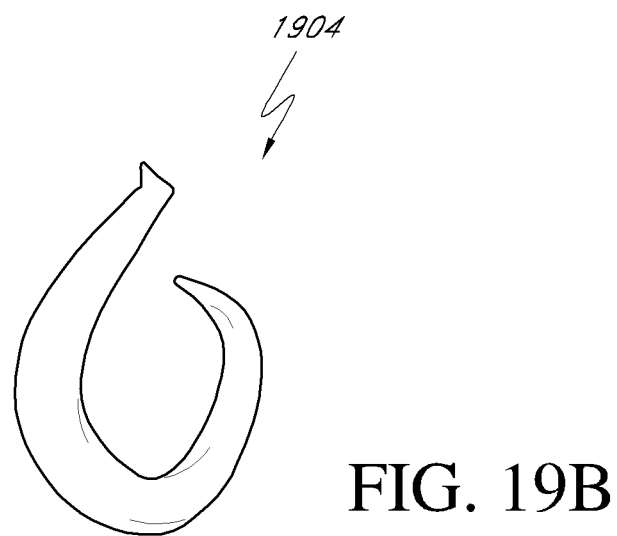

In one embodiment, an alternative device comprises an implant that when placed into the fallopian tubes, prevents pregnancy. FIG. 19A describes a 6-legged device 1901 with the legs terminating at an apical hub 1902. Two or three or more legs may be used. The legs can be corrugated 1903 or straight and can be made of metal or plastic, preferably metal preferably copper which is known to create an inhospitable environment for fertilization to occur. One or more, and preferably each of the legs has a hook at the end for fixation into the wall of the tube. Additional hooks may be provided spaced apart from the free end. FIG. 19B describes a recurved base to the hook 1904 to prevent complete perforation of the leg to minimize puncturing adjacent structures.

Figure 20:
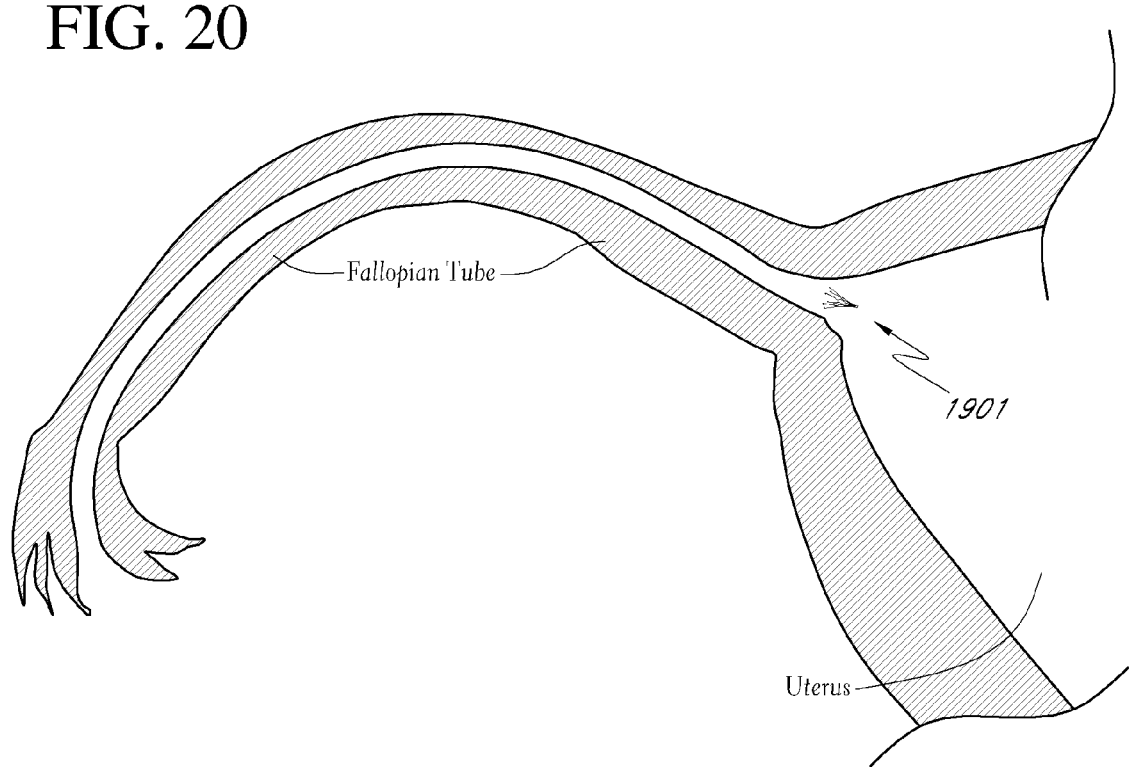

FIG. 20 illustrates one location of placement and a preferred orientation of device 1901. The device should work in any location within the tube and in any orientation. The device is delivered through a catheter preferably less than 3 mm, and preferably less than 2 mm in size. The implant can be left in place permanently or removed via a loop snare or other retrieval mechanism. If the device is to be removed, a hook or loop snare is passed through an open ended catheter to the location of the implant. Once engaged securely with the loop snare or hook, the catheter is pushed over the top of the implant to gather the legs of the device and to protect the walls of the fallopian tubes and uterus from becoming punctured by the sharp hooks at the distal tips of the legs.

To prevent the egg from progressing into the uterus and to prevent sperm from entering the fallopian tube the device can be covered with a microporous membrane. This membrane can be Dacron or other biocompatible materials.

Figure 21:
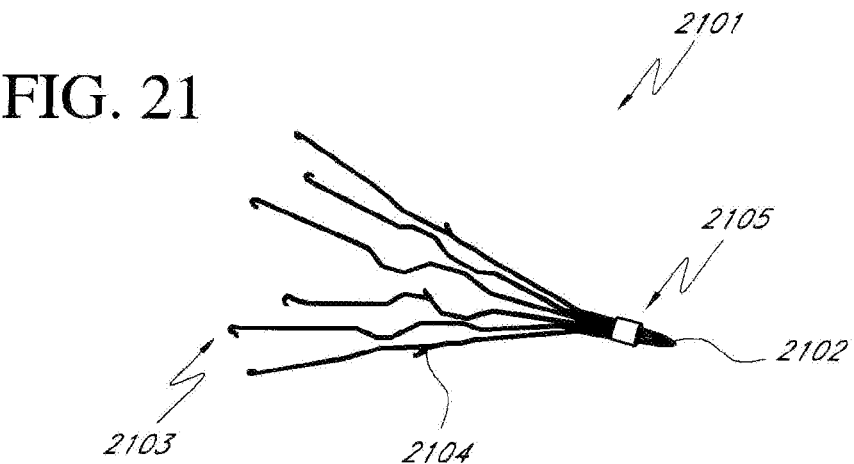
FIGS. 21, 22, and 23 illustrate another embodiment of an implant configured for placement in fallopian tubes to prevent pregnancy.

In one embodiment, an implant is placed in the fallopian tube to prevent pregnancy. FIG. 21 describes a 6-legged device 2101 with legs terminating at an apical hub 2102. Each leg has hooks 2103 for engaging the wall of the fallopian tube. These hooks 2103 alternate both up and down on every other leg. Three of the legs have locking barbs 2104 for engaging the containing ring 2105 when it is advanced over the barbs 2104.

Figure 22:
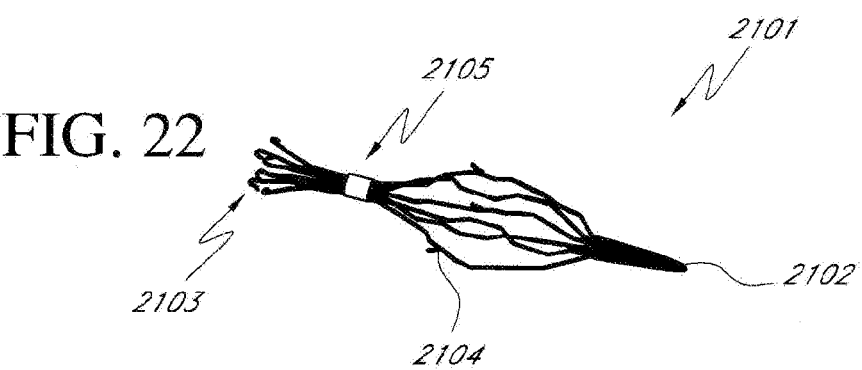
Figure 23:
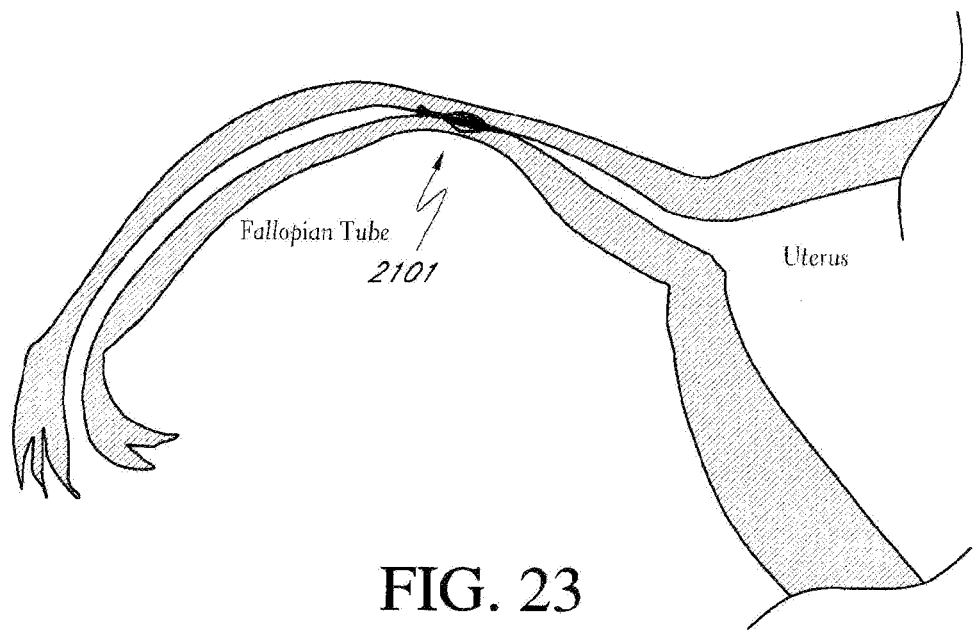

The device is placed through a catheter via the vagina and cervix. The catheter diameter is preferably less than 6 mm, preferably less than 5 mm, preferably less than 4 mm and preferably less than 3 mm. The length of the catheter is preferably greater than 30 cm. Under hysteroscopic or fluoroscopic guidance the catheter is placed into the fallopian tube. Once placed into the fallopian tube, the device is deployed preferably via a coaxial catheter/pusher mechanism such that the pusher is held firm while the catheter is retracted thereby uncovering the occlusion device. With reference to FIG. 22 and FIG. 23, in one embodiment, once the hooks 2103 are firmly engaged into the walls of the fallopian tube the containment ring 2105 is advanced down the legs beyond the locking barb 2104. In one embodiment, the containment ring is attached to a stiffening rod that is housed within the pusher while the implant is temporarily attached to the pusher rod at the apical hub. The pusher rod is held firmly in place while the inner rod connected to the ring is advanced, pushing the ring towards the legs. As the device's legs become gathered within the locking ring the hooks 2103 pull the fallopian wall inward such that the tube occludes immediately or becomes occluded over time. Once deployed, the pusher is detached from the apex of the implant and the inner stiffening rod is detached from the ring. FIG. 23 illustrates the device post deployment within the tube.

Figure 24:
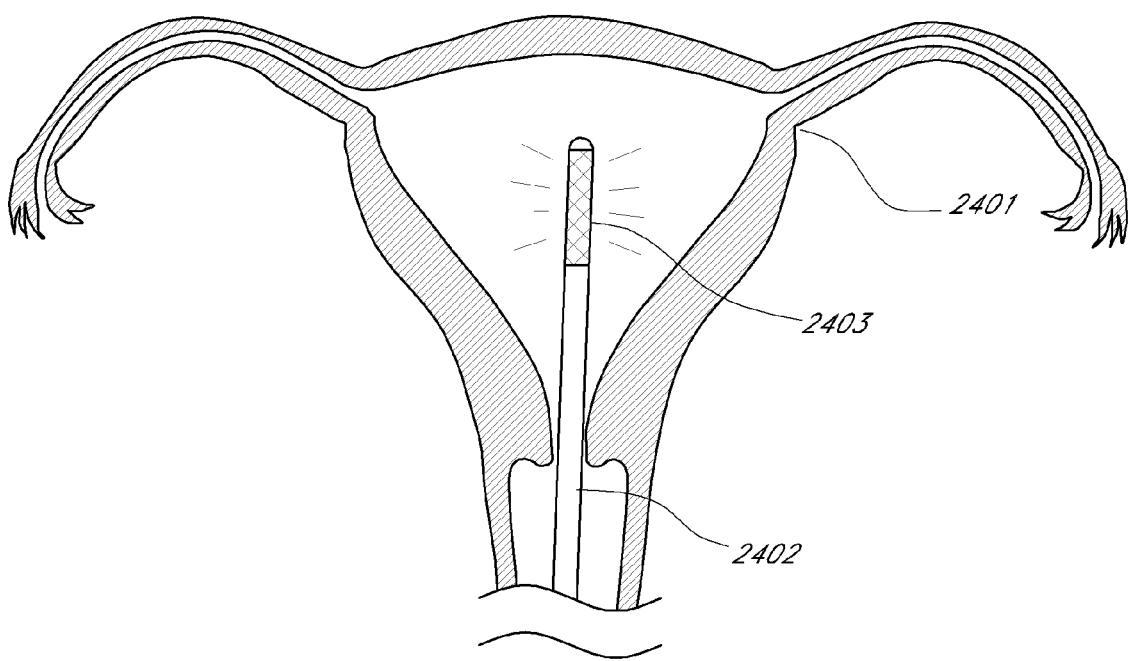
FIG. 24 illustrates an embodiment of an apparatus and method for using a photodynamic drug to prevent abnormal bleeding in the uterus.

With reference to FIG. 24, there is disclosed a method of scarring or inactivating the uterine endometrium by the localized administration of light activated drug therapy. The method of action is to flood the vascular and/or tissue bed of the uterus with an ablation chemical. This chemical is benign until activated by light, preferably UV or infrared. The drug is imbedded into the tissue through an arterial or venous injection either systemically or locally. Systemic injection can be done via any major vessel accessible by the clinician. Localized infusion of the drug can be achieved via direct injection into a vessel adjacent to the uterus, preferably the uterine artery which can be accessed through the cervix. The drug can also be administered topically to the lining of the uterus by flushing the uterine cavity with a carrier fluid or the distension fluid carrying the drug or combining the photodynamic drug with an agent that is easily absorbed such as DMSO.

Once the drug has been placed into the target tissue, the uterus is distended by means of fluid or gas or balloon containing a fluid or gas. A catheter preferably less than 10 mm, preferably less than 8 mm, preferably less than 6 mm, preferably less than 4 mm preferably less than 3 mm containing a light source is placed into the uterine cavity preferably through the vagina and cervix although it could be done percutaneously, through the bowel or bladder, or laproscopically. Once in place the light is activated for a period of time activating the photodynamic drug which ultimately caused a tissue response that prevents abnormal bleeding within the uterus. Such a device could also be used to control abnormal bleeding of the cervix and vagina. FIG. 24 describes a drug in the lining of the uterus 2401. The drug is activated by an intrauterine light source 2403 on a transcervical catheter 2402.

In an alternative embodiment, the distension and light source are housed together in a balloon catheter. This catheter may have more than one lumen such as an inflation lumen to inflate the balloon with a fluid or gas and a second lumen to house the light source used to activate the drug. The balloon material must be of sufficient material that it does not block the light waves emanating from the light source and interacting with the drug. The catheter diameter would be preferably less than 10 mm, preferably less than 8 mm, preferably less than 6 mm, preferably less than 4 mm and preferably less than 3 mm.

In an alternative embodiment the catheter would have yet another lumen extending to and exiting the tip of the catheter to distribute a drug locally before or after the balloon is inflated by gas or fluid. The drug exiting from the tip of the balloon would be forced to the wall of the uterus upon dilation of the balloon and then become activated once the light source within the balloon is activated.

In another embodiment the balloon would contain holes allowing for the weeping of the drug from the balloon so that it could interface with the wall of the uterus before during and after light therapy is administered.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth hereblow not be construed as being order-specific unless such order specificity is expressly stated in the claim.

What is claimed is:

1. A system for occluding a body lumen, comprising:
  an elongate delivery device configured for insertion into a body lumen; and
  a tissue engaging device configured for insertion within a body lumen using the elongate delivery device, the tissue engaging device including a distal element slidably coupled with a proximal element, the distal element having a proximally extending shaft that mates with a locking mechanism of the proximal element,
  a proximal facing outer surface of the distal element, a distal facing outer surface of the proximal element, and an outer surface of the distal element shaft collectively defining an annular recess for receiving wall tissue of a body lumen in which the tissue engaging device has been inserted, the annular recess having an axial length determined by a relative position of the distal element to the proximal element,
  the distal element shaft comprising a vacuum port disposed on an outer surface thereof, the vacuum port in fluid communication with a vacuum supply lumen extending through the elongate delivery device, such that a vacuum source placed in fluid communication with the vacuum supply lumen when the tissue engaging device is inserted in a body lumen would cause plicated wall tissue of the body lumen to be drawn against the outer surface of the distal element shaft within the annular recess, and wherein movement of the distal element towards the proximal element to thereby shorten the axial length of the annular recess would apply compression to plicated wall tissue drawn into the annular recess to thereby form an occlusion of the body lumen.

2. The system of claim 1, wherein the locking mechanism is configured to prevent relative movement between the first element and the second element that would increase the axial length.

3. The system of claim 2, wherein the locking mechanism has a ratchet structure.

4. The system of claim 1, further comprising a pull wire coupled to a proximal end of the distal element shaft so that movement of the pullwire is a proximal direction relative to the proximal element of the tissue engaging device would cause movement of the distal element towards the proximal element.

5. The system of claim 1, wherein the distal element comprises a tissue adhesive.

6. The system of claim 1, wherein the distal element comprises a sclerosing agent.

7. The system of claim 1, wherein the tissue engaging device has a length less than approximately 30 mm.

8. The system of claim 7, wherein the tissue engaging device has a length less than approximately 20 mm.

9. The system of claim 8, wherein the tissue engaging device has a length less than approximately 10 mm.

10. The system of claim 1, wherein the tissue engaging device has an outer diameter less than approximately 3 mm.

11. The system of claim 10, wherein the tissue engaging device has an outer diameter less than approximately 2 mm.

12. The system of claim 1 wherein the tissue engaging element has an outer diameter less than approximately 1 mm.

* * * * *